(12) United States Patent
Wienhues-Thelen et al.

(10) Patent No.: US 10,942,175 B2
(45) Date of Patent: Mar. 9, 2021

(54) USE OF BIOMARKERS IN THE ASSESSMENT OF THE EARLY TRANSITION FROM ARTERIAL HYPERTENSION TO HEART FAILURE

(71) Applicant: Roche Diagnostics Operations, Inc., Indianapolis, IN (US)

(72) Inventors: Ursula-Henrike Wienhues-Thelen, Krailling (DE); Dirk Block, Bichl (DE); Hendrik Huedig, Penzberg (DE); Sabine Vogel-Ziebolz, Munich (DE); Christine Boehm, Huenenberg (CH); Georg Hess, Mainz (DE); Andrea Horsch, Lucerne (CH); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/549,632

(22) Filed: Nov. 21, 2014

(65) Prior Publication Data
US 2015/0079615 A1 Mar. 19, 2015

Related U.S. Application Data

(63) Continuation of application No. 13/776,314, filed on Feb. 25, 2013, now abandoned, which is a continuation of application No. PCT/EP2011/063398, filed on Aug. 3, 2011.

(30) Foreign Application Priority Data

Aug. 26, 2010 (EP) .................................. 10174182
Oct. 6, 2010 (EP) .................................. 10186710

(51) Int. Cl.
*G01N 33/543* (2006.01)
*G01N 33/68* (2006.01)

(52) U.S. Cl.
CPC ... *G01N 33/54306* (2013.01); *G01N 33/6887* (2013.01); *G01N 33/6893* (2013.01); *G01N 2333/4712* (2013.01); *G01N 2333/495* (2013.01); *G01N 2333/58* (2013.01); *G01N 2800/325* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,604,105 A | 2/1997 | Jackowski |
| 5,756,682 A | 5/1998 | Wicks et al. |
| 2009/0221015 A1 | 9/2009 | Spinale et al. |

FOREIGN PATENT DOCUMENTS

| | | |
|---|---|---|
| EP | 0189153 B1 | 10/1991 |
| EP | 1890154 A1 | 2/2008 |
| GB | 2458025 A | 9/2009 |
| WO | 1999/006445 A1 | 2/1999 |
| WO | 2000/070051 A1 | 11/2000 |
| WO | 2005/113585 A3 | 12/2005 |
| WO | 2007/013641 A1 | 2/2007 |
| WO | 2008/015254 A1 | 2/2008 |
| WO | 2008/061978 A3 | 5/2008 |
| WO | 2008/089994 A1 | 7/2008 |
| WO | 2008/140814 A1 | 11/2008 |
| WO | 2009/027514 A1 | 3/2009 |
| WO | 2009/047283 A | 4/2009 |
| WO | 2009/047285 A1 | 4/2009 |
| WO | 2009/111450 A2 | 9/2009 |
| WO | 2009/132815 A1 | 11/2009 |
| WO | 2009/138451 A1 | 11/2009 |
| WO | 2009/150253 A1 | 12/2009 |
| WO | 2009/158451 A1 | 12/2009 |
| WO | 2010/007041 A1 | 1/2010 |
| WO | 2010/012616 A1 | 2/2010 |
| WO | 2010/054016 A1 | 5/2010 |

OTHER PUBLICATIONS

Dispenzieri et al., Survival in patients with primary systemic amyloidosis and raised serum cardiac troponins, The Lancet, 361, (2003), p. 1787-1789) (Year: 2003).*
Kato, Serum Cardiac Troponin T in Cardiac Amyloidosis: Serial Observations in Five Patients, J. Exp. Med., 208, (2006), p. 163-167 (Year: 2006).*
Anderson et al., Molecular basis of human cardiac troponin T isoforms expressed in the developing, adult, and failing heart, Circ. Res. (1995), 76(4), p. 681-684 (abstract, 1 page) (Year: 1995).*
P45379, Uniprot, https://www.uniprot.org/uniprot/P45379. Accessed Nov. 8, 2019 (Year: 2019).*
Welsh et al., Cardiac Troponin T and Troponin I in the General Population, Circulation, 139, (2011), p. 2754-2764 (Year: 2011).*
Aeschbacher, Beat C. et al., "Diastrolic Dysfunction Precedes Myocardial Hypertrophy in the Development of Hypertension," American Journal of Hypertension, 2001, pp. 106-113, vol. 14.
Agewall, S. et al., "Troponin elevation in coronary vs. non-coronary disease," European Heart Journal, 2011, pp. 404-411, vol. 32.
Akaogi, Kotaro et al., "Specific accumulation of tumor-derived adhesion factor in tumor blood vessels and in capillary tube-like structures of cultured vascular endothelial cells," Proceedings of the National Academy of Sciences, Aug. 1996, pp. 8384-8389, vol. 93.
Anderson, Page A. W. et al., "Molecular Basis of Human Cardiac Troponin T Isoforms Expressed in the Developing, Adult, and Failing Heart," Circulation Research, 1995, pp. 681-686, vol. 76 No. 4.
Baek, Seung Joon et al., "Cyclooxyenase Inhibitors Regulate the Expression of a TGF-β Superfamily Member That Has Proapoptotic and Antitumorigenic Activities," Molecular Pharmacology, 2001, pp. 901-908, vol. 59, No. 4.

(Continued)

*Primary Examiner* — Ellen J Marcsisin
(74) *Attorney, Agent, or Firm* — Stinson LLP

(57) ABSTRACT

Methods and systems for diagnosing functional and/or structural abnormalities of the heart preceding heart failure, and for predicting the risk of developing heart failure, in a subject comprising measuring a cardiac troponin in a sample and comparing the measurement to a reference value. Other markers, including GDF15 and IGFBP7 are also measured in some embodiments.

12 Claims, 4 Drawing Sheets

(56) References Cited

OTHER PUBLICATIONS

Bauml, Michael A. and Underwood, Donald A., "Left ventricular hypertrophy: An overlooked cardiovascular risk factor," Cleveland Clinic Journal of Medicine, Jun. 2010, pp. 381-387, vol. 77, No. 6.
Bauskin, Asne R. et al., The propeptide of macrophase inhibitory cytokine (MIC-1), a TGF-β superfamily member, acts as a quality control determinant for correctly folded MIC-1, The EMBO Journal, 2000, pp. 2212-2220, vol. 19, No. 10.
Böttner, Martina et al., "Characterization of the rat, mouse, and human genes of growth/differentiation factor-15/macrophase inhibiting cytokine-1 (GDF-15/MIC-1)," Gene, 1999, pp. 105-111, vol. 237.
Brown, David A. et al., "Concentration in plasma of macrophase inhibitory cytokine-1 and risk of cardiovascular events in women: a nested case-control study," The Lancet, Jun. 2002, pp. 2159-2163, vol. 359.
Burger, Angelika M. et al., "Down-regulation of T1A12/mac25, a novel insulin-like growth factor binding protein related gene, is associated with disease progression in breast carcinomas," Oncogene, 1998, pp. 2459-2467, vol. 16.
Chen, Wei-Chung et al., "Biomarkers in heart failure," Heart, 2010, pp. 314-320, vol. 96.
De Couto, Geoffrey et al., "Early detection of myocardial dysfunction and heart failure," Nature Reviews Cardiology, 2010, pp. 334-344, vol. 7.
DeFilippi, Christopher R. et al., "Association of Serial Measures of Cardiac Troponin T Using a Sensitive Assay With Incident Heart Failure and Cardiovascular Mortality in Older Adults," Journal of the American Medical Association, Dec. 2010, pp. 2494-2502, vol. 304, No. 22.
De Lemos, James A. et al., "Association of Troponin T Detected With a Highly Sensitive Assay and Cardiac Structure and Mortality Risk in the General Population," Journal of the American Medical Association, Dec. 2010, pp. 2503-2512, vol. 304, No. 22.
Dinh, Wilfried et al., "High sensitive troponin T and heart fatty acid binding protein: novel biomarker in heart failure with normal ejection fraction?: A cross-sectional study," BMC Cardiovascular Disorders, 2011, 24 pps. vol. 11, No. 41.
Drazner, Mark H. et al., "Left Ventricular Hypertrophy Is More Prevalent in Blacks Than Whites in the General Population, The Dallas Heart Study," Hypertension, 2005, pp. 124-129, vol. 46.
Ferrieres, Gaelle et al., "Human cardiac troponin I: precise identification of antigenic epitopes and prediction of secondary structure," Clinical Chemistry, 1998, pp. 487-493, vol. 44, No. 3.
Fertin, Marie et al., "Usefulness of Serial Assessment of B-Type Natriuretic Peptide, Troponin I, and C-Reactive Protein to Predict Left Ventricular Remodeling After Acute Myocardial Infarction (from the REVE-2 Study)," American Journal of Cardiology, 2010, pp. 1410-1416, vol. 106.
Giannitsis, Evangelos and Katus, Hugo A., "Troponins and High-Sensitivity Troponins as Markers of Necrosis in CAD and Heart Failure," Herz, 2009, 600-606, vol. 34, No. 8.
Hisano, Tarnao et al., "Crystal Structure of L-2 Haloacid Dehalogenase from *Pseudomonas* sp. YL, "The Journal of Biological Chemistry, Aug. 1996, pp. 20322-20330, vol. 2714, No. 34.
Hromas, Robert et al., "PLAB, a novel placental bone morphogenetic protein," Biochimica et Biophysica Acta, 1997, pp. 40-44, vol. 1354.
Hunt, Sharon Ann et al., "ACC/AHA Guidelines for the Evaluation and Management of Chronic Heart Failure in the Adult: Executive Summary, A Report of the American College of Cardiology/American Heart Association Task Force on Practice Guidelines (Committee to Revise the 1995 Guidelines for the Evaluation and Management of Heart Failure)," Journal of the American College of Cardiology, 2001, pp. 2101-2113, vol. 38, No. 7.
Hunt, Sharon Ann et al., "ACC/AHA 2005 Guideline Update for the Diagnosis and Management of Chronic Heart Failure in the Adult A Report of the American College of Cardiology/American Heart Association Task Force on Practice Guidelines (Writing Committee to Update the 2001 Guidelines for the Evaluation and Management of Heart Failure)," www.acc.org/clinical/guidelines/failure//index.pdf, 2005, 82 pages.
Hwa, Vivian et al., "The Insulin-Like Growth Factor-Binding Protein (IGFBP) Superfamily," Endocrine Reviews, 1999, pp. 761-787, vol. 20, No. 6.
Inomata, Takayuki, "Cardiac-Troponin-Guided Heart Failure Management—Is It Possible in Clinic Practice?," Circulation Journal, Mar. 2011, pp. 542-543, vol. 75.
Jones, John I. and Clemmons, David R., "Insulin-Like Growth Factors and Their Binding Proteins: Biological Actions," Endocrine Reviews, 1995, pp. 3-34, vol. 16, No. 1.
Kawahara, Chiho et al., "Prognostic Role of High-Sensitivity Cardiac Troponin T in Patients With Nonischemic Dilated Cardiomyopathy," Circulation Journal, Mar. 2011, pp. 656-661, vol. 75.
Kelley, Walter E. et al., "Increases of Cardiac Troponin in Conditions other than Acute Coronary Syndrome and Heart Failure," Clinical Chemistry, 2009, pp. 2098-2112, vol. 55, No. 12.
Kempf, Tibor et al., "Circulating Concentrations of Growth-Differentiation Factor 15 in Apparently Healthy Elderly Individuals and Patients with Chronic Heart Failure as Assessed by a New Immunoradiometric Sandwich Assay," Clinical Chemistry, 2007, pp. 284-291, vol. 53, No. 2.
Kempf, Tibor and Wollert, Kai C., "Growth-Differentiation Factor-15 in Heart Failure," Heart Failure Clinics, 2009, pp. 537-547, vol. 5.
Kim, Ho-Seong et al., "Identification of a family of low-affinity insulin-like growth factor binding proteins (IGFBPs): Characterization of connective tissue growth factor as a member of the IGFBP superfamily," Proceedings of the National Academy of Sciences, Nov. 1997, pp. 12981-12986, vol. 94.
Kim, Young-Sin and Greenberg, Barry, "Update on Renin-Angiotension-Aldosterone Blockade in Heart Failure," Current Treatment options in Cardiovascular Medicine, 2009, pp. 455-466, vol. 11.
Kociol, Robb D. et al., "Troponin Elevation in Heart Failure," Journal of the American College of Cardiology, 2010, pp. 1071-1078, vol. 56, No. 14.
Lawton, Lee N. et al., "Identification of a novel member of the TGF-beta superfamily highly expressed in human placenta," Gene, 1997, pp. 17-26, No. 203.
Lindsay, M. Mitchell et al., "TIMP-1 A Marker of Left Ventricular Diastolic Dysfunction and Fibrosis in Hypertension," Hypertension, 2002, pp. 136-141, vol. 40.
López-Bermejo, A. et al., "Characterization of Insulin-Like Growth Factor-Binding Protein-Related Proteins (IGFBP-rPs) 1, 2, and 3 in Human Prostate Epithelial Cells: Potential Roles for IGFBP-rP1 and 2 in Senescence of the Prostatic Epithelium," Endocrinology, 2000, pp. 4072-4080, vol. 141, No. 11.
López-Bermejo, Abel, et al., "Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues," The Journal of Clinical Endocrinology & Metabolism, 2003, pp. 3401-3408, vol. 88.
López-Bermejo, Abel, et al., "Insulin Resistance Is Associated With Increased Serum Concentration of IGF-Binding Protein-Related Protein 1 (IGFBP-rP1/MAC25)," Diabetes, Aug. 2006, pp. 2333-2339, vol. 55.
Mak, George J. et al., "Natural History of Markers of Collagen Turnover in Patients With Early Diastolic Dysfunction and Impact of Eplerenone," Journal of the American College of Cardiology, 2009, pp. 1674-1682, vol. 54, No. 18.
Mancia, Giuseppe et al., "2007 Guidelines for the management of arterial hypertension," European Heart Journal, 2007, pp. 1462-1536, vol. 28.
Masson, Serge et al., "An Update on Cardiac Troponins as Circulating Biomarkers in Heart Failure," Current Heart Failure Reports, 2010, pp. 15-21, vol. 7.
McMurray, John J. V., "Systolic Heart Failure," The New England Journal of Medicine, Jan. 21, 2010, pp. 228-238, vol. 362.
McNamara, Dennis M., "Genomic Variation and Neurohormonal Intervention in Heart Failure," Heart Failure Clinics, 2010, pp. 35-43, vol. 6.

(56) References Cited

OTHER PUBLICATIONS

Morrish, D. W. et al., "Identification by Subtractive Hybridization of a Spectrum of Novel and Unexpected Genes Associated with In Vitro Differentiation of Human Cytotrophoblast Cells," Placenta, 1996, pp. 431-441, vol. 17.
Moses, Marsha A. et al., "Troponin I is present in human cartilage and inhibits angiogenesis," Proceedings of the National Academy of Sciences, Mar. 1999, pp. 2645-2650, vol. 96.
Nelson, Mark et al., "A Systematic Review of Predictors of Maintenance of Normotension After Withdrawal of Antihypertensive Drugs," American Journal of Hypertension, 2001, pp. 98-105, vol. 104.
Oh, Youngman et al., "Synthesis and Characterization of Insulin-like Growth Factor-binding Protein (IGFBP)-7," The Journal of Biological Chemistry, Nov. 1996, pp. 30322-30325, vol. 271, No. 48.
Omland, Jorbjørn et al., "A Sensitive Cardiac Troponin T Assay in Stable Coronary Artery Disease," The New England Journal of Medicine, Dec. 24, 2009, pp. 2538-2547, vol. 361.
Ono, Yasuhiro et al., "Expression of prostacyclin-stimulating factor, a novel protein, in tissues of Wistar rats and in cultured cells," Biochemical and Biophysical Research Communications, Aug. 1994, pp. 1490-1496, vol. 202, No. 3.
Paralkar, Vishwas M. et al., "Cloning and Characterization of a Novel Member of the Transforming Growth Factor-β/Bone Morphogenetic Protein Family," The Journal of Biological Chemistry, May 29, 1998, pp. 13760-13767, vol. 273, No. 22.
Communication of a Notice of Opposition dated Oct. 29, 2015 in Application No. EP 11743231.0, 27 pages.
Dolci, Alberto et al., Biochemical Markers for Prediction of Chemotherapy-Induced Cardiotoxicity, American Journal of Clinical Pathology, 2008, pp. 688-695, vol. 130.
Gahlmann, Reinhold et al., Differential Expression of Slow and Fast Skeletal Muscle Troponin C, Journal of Molecular Biology, 1988, pp. 379-391, vol. 201.
Mallamaci, Francesca et al., Troponin Is Related to Left Ventricular Mass and Predicts All-Cause and Cardiovascular Mortality in Hemodialysis Patients, American Journal of Kidney Diseases, 2002, pp. 68-75, vol. 40, No. 1.
Shave, Rob et al., Exercise-Induced Cardiac Troponin Elevation, Journal of the American College of Cardiology, 2010, pp. 169-176, vol. 56, No. 3.
Zethelius, Bjorn et al., Troponin I as a Predictor of Coronary Heart Disease and Mortality in 70-Year-Old Men, Circulation, 2006, pp. 1071-1078, vol. 113.
Beckman Coulter product insert for AccuTnI assay published in Jul. 2010, 18 pages.
Roche Diagnstics GmbH product insert for Elecsys 2010 Troponin T high-sensitivity assay, 6 pages.
Petrovic, Dejanet al., "Cardiac Troponins and Left Ventricular Hypertrophy in Hemodialysis Patients," Clinical Laboratory Journal, 2008, pp. 145-152, vol. 54.
Roche Diagnostics, Troponin T product description, 2007, 5 pages (web: www.jlscmail.ac.uk/cgl-bin/sebadmin. Retrieved May 14, 2014).
Roumen, Luc et al., Synthesis, Biological Evaluation, and Molecular Modeling of 1-Benzyl-1H-imidazoles as Selective Inhibitors of Aldosterone Synthase (CYP11B2), Journal of Medicinal Chemistry, 2010, pp. 1712-1725, vol. 53.
Sato, Yukihito et al., "In patients with heart failure and non-ischemic heart disease, cardiac troponin T is a reliable predictor of long-term echocardiographic changes and adverse cardiac events," Journal of Cardiology, 2009, pp. 221-230, vol. 54.
Siciliano, Massimo et al., "Troponin I serum concentration: a new marker of left ventricular hypertrophy in patients with essential hypertension," Italian Heart Journal, Aug. 2000, pp. 532-535, vol. 1, No. 8.
Sprenger, Cynthia C. et al., "Insulin-like Growth Factor Binding Protein-related Protein 1 (IGFBP-rP1) Is a Potential Tumor Suppressor Protein for Prostate Cancer," Cancer Research, May 1999, pp. 2370-2375, vol. 59.
St. Croix, Brad et al., "Genes Expressed in Human Tumor Endothelium," Science, Aug. 2000, pp. 1197-1202, vol. 289.
"Summary of the 2007 European Society of Hypertension (ESH) and European Society of Cardiology (ESC) Guidelines for the Management of Arterial Hypertension," Vascular Hearth and Risk Management, 2007, pp. 783-795, vol. 3, No. 6.
Sundström, Johan et al., "Cardiac troponin-I and risk of heart failure: a community-based cohort study," European Heart Journal, 2009, pp. 773-781, vol. 30.
Sundström, Johan, "Troponin and heart failure: an early warning system worth listening to?," Future Cardiology, 2009, pp. 321-324, vol. 5, No. 4.
Tate, Jillian R. et al., "Standardisation of cardiac troponin I measurement; past and present," Pathology, 2010, pp. 402-409, vol. 42, No. 5.
Verma, Anil and Solomon, Scott D., "Diastrolic Dysfunction as a Link Between Hypertension and Heart Failure," Hypertensive Disease: Current Challenges, New Concepts, and Management, May 2009, pp. 647-664, vol. 93, No. 3.
Wallace, Thomas W. et al., "Prevalence and Determinants of Troponin T Elevation in the General Population," Circulation, 2006, pp. 1958-1965, vol. 113.
Yamauchi, Teruaki et al., "Purification and molecular cloning of prostacyclin-stimulating factor from serum-free conditioned medium of human diploid fibroblast cells," Biochemical Journal, 1994, pp. 591-598, vol. 303.
Yokoyama-Kobayashi, Midori et al.,"Human cDNA Encoding a Novel TGF-β Superfamily Protein Highly Expressed in Placenta," Journal of Biochemistry, 1997, pp. 622-626, vol. 122.
Kubo, Tom et al., Serum Cardiac Troponin I is Related to Increased Left Ventricular Wall Thickness, Left Ventricular Dysfunction, and Male Gender in Hypertrophic Cardiomyopathy, Clinical Cardiology, 2010, pp. E1-E7, vol. 33, No. 2.
Mallamaci, Francesca et al., Diagnostic value of troponin T for alterations in left ventricular mass and function in dialysis patients, Kidney International, 2002, pp. 1884-1890, vol. 62.
Giuliani, Isabelle et al., Determination of cardiac troponin I forms in the blood of patients with unstable angina pectoris, Clinical Biochemistry, 2002, pp. 111-117, vol. 32.
Otsuka, Toshiaki et al., Association between high-sensitivity cardiac troponin T levels and the predicted cardiovascular risk in middle-aged men without overt cardiovascular disease, American Heart Journal, 2010, pp. 972-978, vol. 159, No. 6.
Maynard, S. J. et al., Troponin T or troponin I as cardiac markers in ischaemic heart disease, Heart, 2000, pp. 371-373, vol. 83.
Siciliano, Massimo et al., Troponin I serum concentration: a new marker of left ventricular hypertrophy in patients with essential hypertension, Italian Heart Journal 2000, pp. 532-535, vol. 8. No. 1.

* cited by examiner

USE OF BIOMARKERS IN THE ASSESSMENT OF THE EARLY TRANSITION FROM ARTERIAL HYPERTENSION TO HEART FAILURE

CROSS-REFERENCE TO RELATED APPLICATIONS

This application is a continuation of U.S. application Ser. No. 13/776,314 filed Feb. 25, 2013, which is a continuation of International Application No. PCT/EP2011/063398, filed Aug. 3, 2011 which claims the benefit of European Patent Application No. 10174182.5, filed Aug. 26, 2010, and European Patent Application No. 10186710.9, filed Oct. 6, 2010, the disclosures of which are hereby incorporated by reference in their entirety.

BACKGROUND OF THE DISCLOSURE

An aim of modern medicine is to provide personalized or individualized treatment regimens. Those are treatment regimens which take into account a patient's individual needs or risks. Personalized or individual treatment regimens may even be taken into account for measures where it is required to decide on potential treatment regimens.

Heart failure (HF) is a major and growing public health problem. It is estimated that approximately 5 million patients in the USA have HF, more than 500 000 patients are diagnosed with HF for the first time each year, and more than 50.000 patients in the US die each year of HF as a primary cause. Heart failure (HF) is one of the main causes of morbidity and mortality in developed countries. Because of aging of the population and greater longevity of patients with cardiovascular disease incidence and prevalence of HF are increasing.

In general, HF is diagnosed by e.g. echocardiography and Doppler sonography which, however, only permit to diagnose symptomatic later stages of HF. Individuals suffering from presymptomatic forms of HF cannot be diagnosed by these established methods. Poor diagnostic capabilities is one of the reasons that the survival rate for individuals diagnosed for HF is only 50% for 5 years.

BRIEF SUMMARY OF THE DISCLOSURE

The present disclosure relates to a method for predicting risk of an individual bearing risk factors of developing heart failure, to suffer from heart failure. The present disclosure further relates to diagnosing early stages of functional and/or structural abnormalities of the heart preceding left ventricular hypertrophy (LVH) and/or heart failure in an individual bearing risk factors of developing heart failure. In an embodiment, the subject suffers from hypertension and/or diabetes. In another embodiment, the subject suffers from diastolic dysfunction. In yet another embodiment the subject is female. In particular, the present disclosure provides a method of predicting the risk of heart failure before left ventricular hypertrophy (LVH) is apparent (i.e. visible by e.g. echocardiography or ECG). The present disclosure, furthermore, relates to a method of predicting the risk of such an individual to suffer from heart failure as a consequence of the presence of functional and/or structural abnormalities of the heart. The present disclosure further relates to a method of predicting the risk of a female subject to suffer from left ventricular hypertrophy. The present disclosure, furthermore, relates to a method of predicting the risk of such an individual to suffer from cardiovascular and renal events preceding heart failure: Ischemic stroke, detrimental non-fatal stroke, myocardial ischemia/myocardial infarction, arterial aneurysm, chronic kidney failure and finally heart failure. The diagnosis is carried out by measuring the concentrations of at least one cardiac troponin. As the case may be, optionally one further marker selected from GDF-15 and IGFBP7 is determined. The method can also be used for deciding on a possible treatment of an individual bearing risk factors of suffering from heart failure and/or having been diagnosed for functional and/or structural abnormalities of the heart preceding heart failure and/or predicted an elevated risk of suffering from heart failure. Moreover, the present disclosure relates to a device and a kit adapted to carry out the method of the present disclosure. Also encompassed by the present disclosure is the use of the above-specified plurality of markers for diagnosing and/or predicting, in an individual bearing risk factors of developing heart failure, the above-referenced health states.

According to some embodiments, a method of diagnosing a heart functional or structural abnormality preceding heart failure in a subject is provided. Embodiments of the method include the steps of contacting, in vitro, a portion of a sample of the subject with an antibody having specific binding affinity for an epitope of a cardiac troponin marker or variant thereof, whereby a complex of the antibody and the cardiac troponin marker or variant thereof is formed; calculating a concentration of the cardiac troponin marker or variant thereof in the sample based on an amount of complex formed in said step of contacting; comparing the concentration of the cardiac troponin marker or variant thereof determined in said step of calculating with a cardiac troponin marker reference value; and diagnosing a heart functional or structural abnormality preceding heart failure in the subject if the concentration of the cardiac troponin marker or variant thereof in the sample is greater than the cardiac troponin marker reference value.

In some embodiments of the method provided herein, the method further comprises the step of contacting, in vitro, a portion of the sample of the subject with a second antibody having specific binding affinity for a second epitope of the cardiac troponin marker or variant thereof, whereby a complex of the antibody, the cardiac troponin marker or variant thereof, and the second antibody is formed.

According to yet further embodiments of the instant disclosure, a device adapted for diagnosing a heart functional or structural abnormality preceding heart failure in a subject is provided. Embodiments of the device include means for determining an amount of a cardiac troponin marker of variant thereof in a sample from the subject; implemented rules for comparing the determined amount of the cardiac troponin marker of variant thereof to a cardiac troponin marker reference value, the cardiac troponin marker reference value existing as a stored value; and means for implementing the rules, wherein an amount of the cardiac troponin marker or variant thereof greater than the cardiac troponin marker reference value is indicative of a heart functional or structural abnormality preceding heart failure.

According to some embodiments of the device, the means for determining the amount of the cardiac troponin marker of variant thereof in the sample comprises an antibody having specific binding affinity for an epitope of the cardiac troponin marker of variant thereof. According to some further embodiments of devices disclosed herein, said means for determining the amount of the cardiac troponin marker of variant thereof in the sample further comprises a second antibody having specific binding affinity for a second epitope of the cardiac troponing marker or variant thereof. In yet further embodiments, the epitope of the cardiac troponin marker or variant thereof consists of amino acids 125-131 and the second epitope of the cardiac troponin marker or variant thereof consists of amino acids 136-147

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

Figure 1:
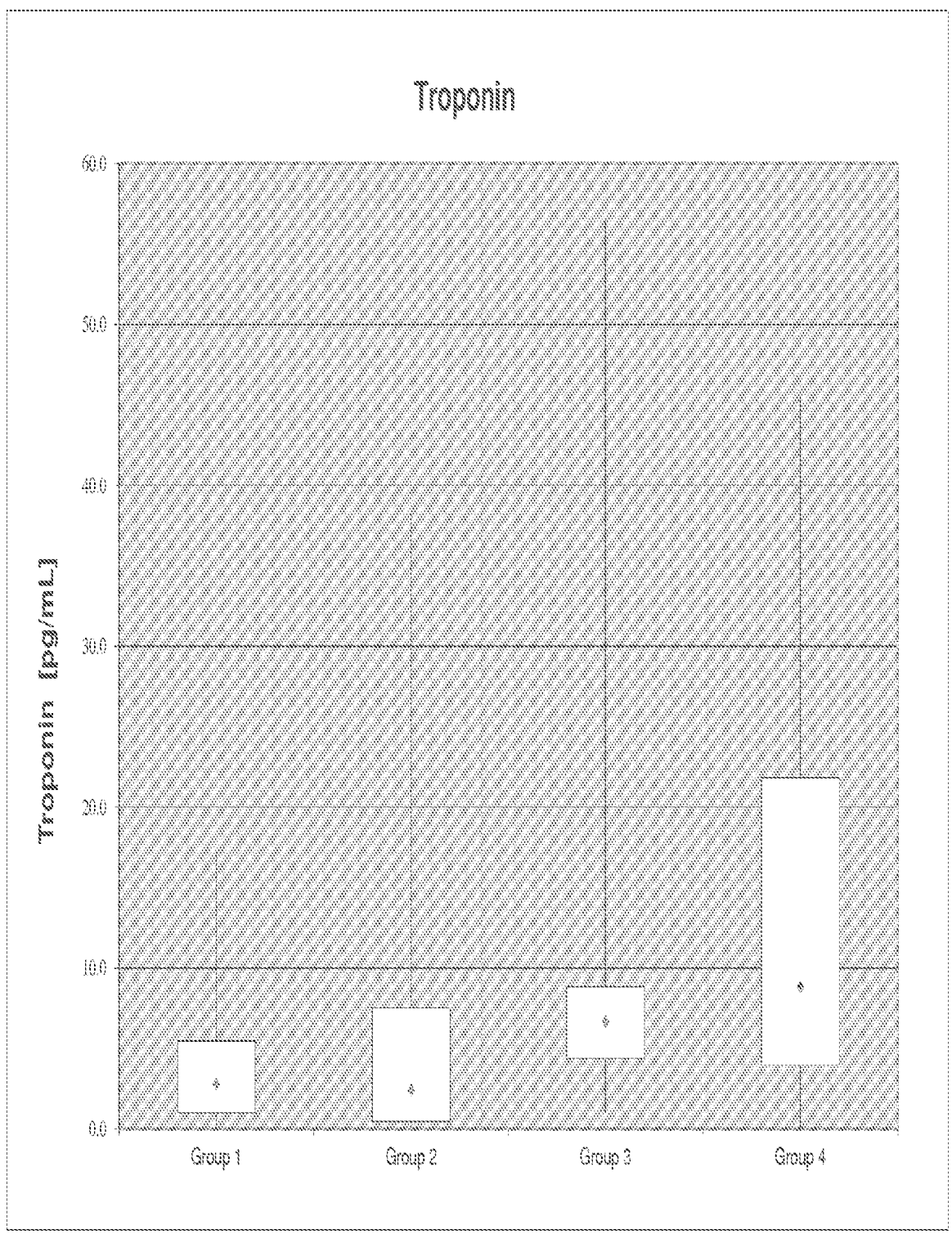
FIG. 1 is a bar graph presenting the values of troponin T in patients belonging to group 1, 2, 3 or 4 as described in the Examples.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Heart failure is a complex clinical syndrome that can result from any structural or functional cardiac disorder that impairs the ability of the ventricle to fill with or eject blood and to ensure the body's metabolic needs for supply with blood/oxygen. In such cases, the body tries to compensate lack of supply by structural changes of the myocardium (e.g. fibrosis, apoptosis, necrosis) aiming at maintaining the required supply. First structural changes to the myocardium are, in general, reversible changes but which, when untreated, turn to non reversible permanent changes which finally lead to chronic HF with the final stage of terminal HF.

HF is classified into various degrees of severity. One classification is the so-called NYHA (New York Heart Association) classification. Heart failure patients are classified NYHA classes I, II, III and IV. A patient having heart failure has already experienced structural and functional changes to his pericardium, myocardium, coronary circulation or cardiac valves. He will not be able to fully restore his health, and is in need of a therapeutical treatment. Patients of NYHA Class I have no obvious symptoms of cardiovascular disease but already have objective evidence of functional impairment. Patients of NYHA class II have slight limitation of physical activity. Patients of NYHA class III show a marked limitation of physical activity. Patients of NYHA class IV are unable to carry out any physical activity without discomfort. They show symptoms of cardiac insufficiency at rest.

This functional classification is supplemented by the more recent classification by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy (LVH, a phenomenon in which the walls of the ventricles thicken) and/or impaired LV function would be designated as stage B. Stage C then denotes patients with current or past symptoms of HF associated with underlying structural heart disease (the bulk of patients with HF), and stage D designates patients with truly refractory HF.

Arterial hypertension places increased tension on the left ventricular myocardium that is manifested as stiffness and hypertrophy. Independently thereof, atherosclerosis develops within the coronary vessels as a consequence of hypertension. Subjects with hypertension have increased risk of detrimental non-fatal stroke. Antihypertensive medication may help to reduce the risk of detrimental non-fatal stroke. It is known that subjects suffering from diabetes mellitus are at an elevated risk of suffering from atherosclerosis. Subjects suffering from atherosclerosis are at an elevated risk of ischemic stroke. Antihypertensive medication may help to reduce the risk of ischemic stroke and ischemic heart disease.

Systolic dysfunction has been found to be associated with an increased risk to develop symptomatic systolic HF. Diastolic dysfunction is believed to be a precursor of diastolic HF. Early treatment of hypertension may improve diastolic function. A large number of individuals with left ventricular dysfunction, systolic as well as diastolic dysfunction, remain undiagnosed and untreated, although early therapy may improve outcome. Untreated hypertension is associated with an increased risk to develop heart failure, which is often is preceded by other cardiovascular and renal events: Hypertension or diabetes leading to ischemic stroke, detrimental non-fatal stroke, myocardial ischemia/myocardial infarction, arterial aneurysm and finally heart failure, if the patient lives long enough. Persistent hypertension is a leading cause of chronic kidney failure. Early treatment of hypertension may help to prevent disease progression to a variety of cardiovascular as well as renal death risks Accordingly, there is a strong need to have methods and means at hand which allow to identify in subjects functional and/or structural abnormalities of the heart preceding heart failure caused by functional and/or structural changes to their myocardium, before the patient develops symptoms of overt heart failure (e.g. those typical for stages C or D of the ACC/AHA classification). In some embodiments, the methods and means shall permit to identify subjects at an early stage of impaired cardiac function, i.e. the subjects are about to develop impaired cardiac function. According to some embodiments, the subjects should be at a stage where minimum functional and/or structural changes to the patient's pericardium, myocardium, coronary circulation or cardiac valves (e.g. structural changes to the patient's left ventricle) have occurred, at least in some cases before left ventricular hypertrophy becomes apparent. According to some embodiments, the subject should be about to leave stage A of the ACC/AHA classification and be about to enter stage B of the ACC/AHA classification. The method and means permit the identification of subjects at increased risk of developing HF and associated further cardiovascular and renal diseases and improved risk stratification in patients with early functional and/or structural abnormalities of the heart preceding heart failure (stages A/B according to AHA/ACC classification) in order to initiate appropriate preventive treatment before non-reversible progression of HF or major complications occur. The methods and means shall permit to make early decisions on an appropriate treatment of the respective individual/subject and to monitor the treatment.

In the studies carried out in the context of the present disclosure, it was surprisingly found that the determination of the concentration of a cardiac troponin allows for the identification of subjects at early stage B even before hypertrophy becomes apparent, and thus, of subjects having risk factors of suffering from heart failure and showing first structural changes to the left ventricle and/or diastolic dysfunction, but not suffering from left ventricular hypertrophy. Thus, the determination of a cardiac troponin allows for differentiating between subjects with first structural changes to the left ventricle and/or diastolic dysfunction and subjects without first structural changes to the left ventricle and/or diastolic dysfunction. In particular, the determination of a cardiac troponin allows identification of female subjects at early stage B.

In contrast, the studies carried out in the context of the present disclosure further showed that NT-proBNP, i.e. a well-known marker for the diagnosis of heart failure, failed to identify subjects with first structural changes to the left ventricle and/or diastolic dysfunction. Rather, NT-proBNP was only increased in patients with left ventricular hypertrophy (LVH). The level of NT-proBNP was not increased in patients without LVH, and thus in patients with a left ventricular mass index below cutoff used to define LVH. Thus, in contrast to NT-proBNP, cardiac troponins are valuable markers for the diagnosis of first functional and/or structural abnormalities of the heart preceding LVH and heart failure (and, thus, in subjects without LVH).

The findings of the present disclosure are advantageous since they allow for an early diagnosis of structural and/or functional abnormalities of the heart preceding heart failure and/or preceding left ventricular hypertrophy. Early functional and/or structural abnormalities of the heart and heart failure often remain undiagnosed, particularly in women. First structural changes to the heart are, in general, reversible changes but which, when untreated, turn to non reversible permanent changes which finally may lead to chronic HF with the final stage of terminal HF. Therefore, the early diagnosis of structural changes to the heart since appropriate preventive treatment can be initiated before progression to LVH and/or to HF or other major complications occur.

Method of Diagnosing.

Accordingly, the present disclosure relates to a method of diagnosing in a subject functional and/or structural abnormalities of the heart typically heart failure, based on the comparison of the concentrations of at least on cardiac troponin or a variant thereof, and optionally of one or more other markers of heart failure, to the concentration of this or these marker(s) in a control sample.

The method of the disclosure may comprise the following steps: a) measuring in a sample obtained from the subject the concentration of at least one cardiac troponin or a variant thereof; b) optionally measuring in the sample the concentration of one or more other marker(s) of heart failure; and c) diagnosing the said functional and/or structural abnormalities by comparing the concentration determined in step (a) and optionally the concentration(s) determined in step (b) to reference amounts, e.g. to the concentration of this marker or these markers as established in a control sample.

Therefore, the present disclosure provides a method of diagnosing in a subject functional and/or structural abnormalities of the heart preceding heart failure, the method comprising the steps of
 a) measuring in a sample obtained from the subject the concentration of at least one cardiac troponin or a variant thereof,
 b) optionally measuring in the sample the concentration of one or more other marker(s) of heart failure, and
 c) diagnosing said functional and/or structural abnormalities by comparing the concentration determined in step (a) and optionally the concentration(s) determined in step (b) with a reference amount.

In general, the subject does not suffer from heart failure, i.e. the patient has not experienced permanent structural or functional damages to his myocardium. According to some embodiments, the subject bears risk factors for heart failure. These are known to the person skilled in the art and include e.g. hypertension and diabetes. Also according to some embodiments, the subject does not show overt signs and/or symptoms of heart failure. In some embodiments, the subject does not show LVH.

According to some embodiments, the subject suffers from hypertension, diabetes, obesity, metabolic syndrome and/or a history of smoking (i.e. the subject has a history of smoking). In an exemplary embodiment, the subject suffers from hypertension and/or diabetes.

According to some embodiments, the structural and/or functional abnormality of the heart preceding heart failure and/or left ventricular hypertrophy is an abnormality selected from left ventricular structural changes, an increased septum diameter, increased posterial wall diameter, and diastolic dysfunction.

In some embodiments, the subject is female.

Accordingly, the present disclosure particularly relates to a method of diagnosing functional and/or structural abnormalities of the heart preceding heart failure and/or preceding left ventricular hypertrophy in a subject suffering from hypertension, diabetes, obesity, metabolic syndrome and/or having a history of smoking, the method comprising the steps of:
 a) measuring in a sample obtained from the subject the concentration of at least one cardiac troponin or a variant thereof,
 b) optionally measuring in the sample the concentration of one or more other marker(s) of heart failure, and
 c) diagnosing said functional and/or structural abnormalities by comparing the concentration determined in step (a) and optionally the concentration(s) determined in step (b) with a reference amount
 wherein the subject does not show left ventricular hypertrophy, and
 wherein the structural and/or functional abnormalities of the heart preceding heart failure and/or left ventricular hypertrophy comprise an abnormality selected from a left ventricular structural change, an increased septum diameter, an increased posterial wall diameter, and diastolic dysfunction.

Method of Differentiating.

In a further embodiment, the present disclosure relates to a method of differentiating between a subject only bearing risk factors of developing heart failure and a subject not only bearing risk factors but already suffering from functional and/or structural abnormalities of the heart preceding heart failure, based on the comparison of the concentrations of at least on cardiac troponin or a variant thereof, and optionally of one or more other markers of heart failure, to the concentration of this or these marker(s) in a control sample.

The method of the disclosure may comprise the following steps: a) measuring in a sample obtained from the subject the concentration of at least one cardiac troponin or a variant thereof; b) optionally measuring in the sample the concentration of one or more other marker(s) of heart failure; and c) assessing the said functional and/or structural abnormalities by comparing the concentration determined in step (a) and optionally the concentration(s) determined in step (b) to reference amounts, e.g. to the concentration of this marker or these markers as established in a control sample.

Accordingly, the present disclosure provides a method of differentiating between a subject only bearing risk factors of developing heart failure and a subject not only bearing risk factors but already suffering from functional and/or structural abnormalities of the heart preceding left ventricular hypertrophy and/or preceding heart failure, the method comprising the steps of:
  a) measuring in a sample obtained from the subject the concentration of at least one cardiac troponin or a variant thereof,
  b) optionally measuring in the sample the concentration of one or more other marker(s) of heart failure, and
  c) differentiating between said subjects (i.e. those only bearing risk factors of developing heart failure and those not only bearing risk factors but already suffering from functional and/or structural abnormalities of the heart preceding heart failure) by comparing the concentration determined in step (a) and optionally the concentration(s) determined in step (b) with a reference amount.

In general, the subject (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. The risk factors for heart failure are known to the person skilled in the art and include e.g. hypertension and diabetes. Also in some embodiments, the subject does not show overt signs and/or symptoms of heart failure. According to some embodiments, the subject does not show LVH.

According to some embodiments, the structural and/or functional abnormality of the heart preceding heart failure and/or preceding left ventricular hypertrophy is an abnormality selected from left ventricular structural changes, an increased septum diameter, increased posterial wall diameter, and diastolic dysfunction.

Thus, the present disclosure also relates to a method of differentiating between a subject only bearing risk factors of developing heart failure and a subject not only bearing risk factors but already suffering from functional and/or structural abnormalities of the heart preceding heart failure and/or preceding left ventricular hypertrophy, the method comprising the steps of:
  a) measuring in a sample obtained from the subject the concentration of at least one cardiac troponin or a variant thereof,
  b) optionally measuring in the sample the concentration of one or more other marker(s) of heart failure, and
  c) differentiating between said subjects by comparing the concentration determined in step (a) and optionally the concentration(s) determined in step (b) with a reference amount,
  wherein the subject may not show left ventricular hypertrophy
  wherein the structural and/or functional abnormalities of the heart preceding heart failure and/or preceding left ventricular hypertrophy comprise an abnormality selected from a left ventricular structural change, an increased septum diameter, an increased posterial wall diameter, and diastolic dysfunction.

The present disclosure also provides methods and means to predict the risk of subjects to suffer from heart failure. According to some embodiments, the subjects bear risk factors of developing heart failure and are subjects classified in stage A. The present disclosure provides methods and means to predict the risk of heart failure before left ventricular hypertrophy (LVH) is apparent.

The present disclosure also provides methods and means to diagnose subjects in stage A which are about to enter into stage B (ACC/AHA classification), in particular when left ventricular hypertrophy is not apparent (not identifiable by e.g. echocardiography and/or ECG), and which are at a high risk to progress to left ventricular hypertrophy within the next months or years.

The individual bearing risk factors may have experienced physiological changes towards functional and/or structural abnormalities of the heart preceding heart failure, such as left ventricular diastolic dysfunction, or left ventricular diastolic dysfunction with a preserved left ventricular ejection fraction (LVEF). These functional/structural abnormalities of the heart preceding heart failure are diagnosed by the methods of the present disclosure, which will be explained in greater detail below, in the following paragraphs.

The individual bearing risk factors may in particular have experienced physiological changes towards functional and/or structural abnormalities of the heart preceding heart failure without LVH being apparent, for example ventricular structural changes without LVH, in particular left ventricular diastolic dysfunction without LVH, but also functional and/or structural damage of the myocardium, epicardium, valves, or coronary circulation. These functional/structural abnormalities of the heart preceding heart failure, but without LVH being apparent are diagnosed by the methods of the present disclosure, which will be explained in greater detail below, in the following paragraphs.

In a further embodiment, the present disclosure provides methods and means to stratify these subjects for treatment with antihypertensive drugs, in particular as a consequence of early diagnosis of functional and/or structural abnormalities of the heart and thereby prediction of heart failure even before LVH is apparent (in particular, even before LVH is visible by e.g. echocardiography or ECG).

The methods and means of the present disclosure permit to diagnose, in a straightforward and simple manner, if a subject suffers from functional and/or structural abnormalities of the heart preceding heart failure. In particular, the present disclosure advantageously permits to diagnose early stages of functional and/or structural abnormalities of the heart preceding heart failure in a subject, as defined below, in particular before left ventricular hypertrophy LVH becomes apparent. Accordingly, the present disclosure also provides a method of differentiating between risk factors of developing heart failure (subjects bearing risk factors of developing heart failure) and functional and/or structural abnormalities of the heart preceding heart failure.

The methods and means of the present disclosure permit to predict the risk of an individual bearing risk factors of developing heart failure to suffer from heart failure. In particular the present disclosure advantageously permits to predict the risk of heart failure before left ventricular hypertrophy (LVH) is apparent. Further methods of the present disclosure permit therapy adaption of subjects at risk of heart failure before LVH becomes apparent as a consequence of diagnosing functional and/or structural abnormalities of the heart preceding heart failure.

Further methods of the present disclosure include methods of deciding on the therapy and monitoring the therapy of an individual having been identified to suffer from functional and/or structural abnormalities of the heart preceding heart failure. These embodiments will become apparent from studying the present application in its entirety. For reasons of clarity, the principles of the present disclosure including its exemplified embodiments will be laid out hereinafter in the context of the methods of the present disclosure which have been cited in the form of an independent claim beforehand (diagnosing functional and/or structural abnormalities of the heart preceding heart failure and differentiating between individuals having the said functional and/or structural abnormalities of the heart and those only bearing risk factors). If not stated otherwise, these principles and embodiments also apply in respect to the further methods belonging to the present disclosure.

General Definitions

Heart failure can be classified into a functional classification system according to the New York Heart Association (NYHA). Patients of NYHA Class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than ordinary activity causes fatigue, palpitation, or dyspnea. Patients of NYHA class IV are unable to carry out any physical activity without discomfort. They show symptoms of cardiac insufficiency at rest. Heart failure, i.e., an impaired systolic and/or diastolic function of the heart, can be determined also by, for example, echocardiography, angiography, scintigraphy, or magnetic resonance imaging. This functional impairment can be accompanied by symptoms of heart failure as outlined above (NYHA class II-IV), although some patients may present without significant symptoms (NYHA I).

The present disclosure refers to the more recent ACC/AHA classification of heart failure, identifying 4 stages involved in the development of the HF syndrome. The first 2 stages (A and B) are clearly not HF but are an attempt to help healthcare providers identify patients early who are at risk for developing HF. Stages A and B patients are best defined as those with risk factors that clearly predispose toward the development of HF. Stage C then denotes patients with current or past symptoms of HF associated with underlying structural heart disease, and Stage D designates patients with truly refractory HF who might be eligible for specialized, advanced treatment strategies such as mechanical circulatory support, procedures to facilitate fluid removal, continuous inotropic infusions, or cardiac transplantation or other innovative or experimental surgical procedures, or for end-of-life care, such as hospice. This classification recognizes that there are established risk factors and structural prerequisites for the development of HF and that therapeutic interventions introduced even before the appearance of LV dysfunction or symptoms can reduce the population morbidity and mortality of HF.

The definition of the various stages is as follows (taken from the ACC/AHA guidelines for the evaluation and management of chronic heart failure in the adult, J. Am. Coll. Cardiol. 2001; 38; 2101-2113). The following includes a description of the stage and examples for pathophysiological states in individuals which would be classified in the respective stage.

Stage A. Description:
Patients at high risk of developing HF because of the presence of conditions that are strongly associated with the development of HF. Such patients have no identified structural or functional abnormalities of the pericardium, myocardium, coronary circulation or cardiac valves and have never shown signs or symptoms of HF.
Examples:
Systemic hypertension; coronary artery disease; diabetes mellitus; history of cardiotoxic drug therapy or alcohol abuse; personal history of rheumatic fever; family history of cardiomyopathy.

Stage B. Description:
Patients who have developed structural heart disease that is strongly associated with the development of HF but who have never shown signs or symptoms of HF.
Examples:
Left ventricular hypertrophy or fibrosis; left ventricular dilatation or hypocontractility; asymptomatic valvular heart disease; previous myocardial infarction.

Stage C. Description:
Patients who have current or prior symptoms of HF associated with underlying structural heart disease.
Examples:
Dyspnea or fatigue due to left ventricular systolic dysfunction; asymptomatic patients who are undergoing treatment for prior symptoms of HF.

Stage D. Description:
Patients with advanced structural heart disease and marked symptoms of HF at rest despite maximal medical therapy and who require specialized interventions.
Examples:
Patients who are frequently hospitalized for HF or cannot be safely discharged from the hospital; patients in the hospital awaiting heart transplantation; patients at home receiving continuous intravenous support for symptom relief or being supported with a mechanical circulatory assist device; patients in a hospice setting for the management of HF.

The ACC/AHA stages A, B, C and D specified beforehand are referred to in the context of the present disclosure as "stage A", "stage B", "stage C", and "stage D".

In the context of the present disclosure, subjects of stage A having risk factors typically associated with the development of heart failure but no identified structural or functional abnormalities of the pericardium, myocardium, cardiac valves or coronary circulation are subjects not having functional and/or structural abnormalities of the heart preceding heart failure. Subjects of stage B who have developed functional and/or structural heart disease that is strongly associated with the development of and typically precedes HF but who have never shown signs or symptoms of HF are subjects having functional and/or structural damage of the myocardium, epicardium, valves, or coronary circulation. The present disclosure advantageously diagnoses early stages of functional and/or structural abnormalities of the heart preceding heart failure (early stage B) and even preceding LVH (late stage B). The present disclosure also differentiates between early stages of functional and/or structural abnormalities of the heart preceding heart failure (early stage B) and later stages of functional and/or structural abnormalities of the heart preceding heart failure (late stage B).

Functional and/or Structural Abnormalities of the Heart Preceding Heart Failure.

In the context of the methods of the present disclosure, functional and/or structural abnormalities of the heart preceding heart failure and/or preceding left ventricular hypertrophy shall be diagnosed. The term "abnormalities" as used herein, is intended to mean "at least one abnormality". Thus, one abnormality or more than one abnormality may be diagnosed in the context of the methods described herein.

The term "functional and/or structural abnormalities of the heart preceding heart failure" relates to several pathological states of the myocardium which are known in the art to typically occur prior to heart failure (i.e. they typically precede heart failure). Functional and/or structural abnormalities of the heart preceding heart failure, in the sense of the present disclosure, are generally symptomless functional and/or structural abnormalities of the heart preceding heart failure. Functional and/or structural abnormalities of the heart preceding heart failure may disappear after removing the underlying cause or by training exercise. Functional and/or structural abnormalities of the heart preceding heart failure, in particular symptomless functional and/or structural abnormalities of the heart preceding heart failure, may also develop into heart failure.

The term "functional and/or structural abnormalities of the heart preceding heart failure" as used in the present disclosure relates to functional and/or structural change and/or a functional and/or structural damage of the myocardium, epicardium, coronary circulation or valves, and is to be regarded as a functional abnormality of the heart and/or a structural abnormality of the heart. An example for a functional abnormality of the heart is an impaired pumping or filling capacity, often a systolic or a diastolic impairment. An example for a structural abnormality of the heart is a change in the geometry of the left ventricle. Often, the structural and/or functional heart abnormality/impairment is reversible when the underlying cause is remedied (e.g. when appropriately treated) without leaving permanent structural or functional damage to the myocardium typical for heart failure (i.e. an individual classified in stage B can enter back into stage A). An individual having functional and/or structural abnormalities of the heart preceding heart failure does not show signs of heart failure (thus the individual may be apparently healthy).

Heart failure often starts with a change in the geometry of the left ventricle, changing potentially both systolic and diastolic function (left ventricular dysfunction LVD). LVD is sub-divided into systolic LVD and diastolic LVD. LVD may develop into left ventricular hypertrophy (LVH) in which the walls of the ventricle thicken.

Left ventricular dysfunction begins with stress or injury to the myocardium and is generally a progressive process, resulting in a change in the geometry and structure of the LV. The chamber dilates and/or hypertrophies and becomes more spherical. This process is generally referred to as cardiac remodeling. This change in chamber size and structure increases the hemodynamic stresses on the walls of the (failing) heart and depresses its mechanical performance. Furthermore, this may also increase regurgitant flow through the mitral valve, sustaining and exacerbating the remodeling process. Cardiac remodeling generally precedes the development of symptoms (which may take months or even years), continues after the appearance of symptoms, and contributes substantially to worsening of symptoms. Progression of coronary artery disease, diabetes mellitus, hypertension, or the onset of atrial fibrillation may also contribute to the progression of HF.

In the context of the methods of the present disclosure, functional and/or structural abnormalities of the heart preceding heart failure can be diagnosed even before the subject suffers from left ventricular hypertrophy. Thus, the method of the present disclosure allows for diagnosing structural abnormalities of the heart preceding heart failure and/or preceding left ventricular hypertrophy. The term "left ventricular hypertrophy" is well known in the art. A detailed overview on left ventricular hypertrophy can be, e.g. found in standard text books (see Swamy Curr Cardiol Rep (2010) 12:277-282). LVH can be detected by electrocardiography, echocardiography, or cardiac magnetic resonance imaging (MRI). According to some embodiments, LVH is detected by echocardiography. Moreover, criteria for the diagnosis of LVH are well known in the art (Mancia et al., European Heart J. 2007, 28: 1462, Die Innere Medizin: Referenzwerk für den Facharzt-Wolfgang Gerok-2007, page 293, Swamy Curr Cardiol Rep (2010) 12:277-282).

The diagnosis of LVH, may include measurements of the septum diameter, left ventricular posterial wall thickness and end diastolic diameter, with calculation of left ventricular mass according to formulae known in the art. Exemplary criteria for diagnosing LVH are e.g. disclosed in the guidelines (Mancia et al., European Heart J. 2007, 28: 1462).

According to some embodiments, the Cornell voltage criteria, the Cornell product criteria, the Sokolow-Lyon voltage criteria or the Romhilt-Estes point score system is/are used (Mancia et al., European Heart J. 2007, 28: 1462).

The term "left ventricular hypertrophy" (abbreviated "LVH") as used herein, may relate to a thickening of the walls of the ventricles. LVH is, for example, a response to a chronically increased workload on the heart. LVH is found in patients suffering from arterial hypertension is a disease requiring treatment. In the context of the present disclosure functional and/or structural abnormalities of the heart typically precedes left ventricular hypertrophy and/or heart failure.

Hypertrophy as a response to the increased afterload associated with elevated systemic vascular resistance is necessary and protective up to a certain point. Beyond that point, a variety of dysfunctions accompany LVH, including lower coronary vasodilatory capacity, depressed left ventricular wall mechanics, and abnormal left ventricular diastolic filling pattern.

According to some embodiments, a male subject shows LVH (and, thus, may suffer from LVH) if the ratio of the left ventricular mass to body surface is larger than 112 $g/m^2$, or, for example, if the ratio is larger than 125 $g/m^2$. According to some embodiments, a female subject shows LVH (and, thus, may suffer from LVH) if the ratio of the left ventricular mass to body surface is larger than 89 $g/m^2$, or more in some cases, if the ratio is larger than 110 $g/m^2$. (see, e.g. Drazner M H, Dries D L, Peshock R M, Cooper R S, Klassen C, Kazi F, Willett D, Victor R G. Left ventricular hypertrophy is more prevalent in blacks than whites in the general population: the Dallas Heart Study. Hypertension. 2005; 46:124-129).

In the context of the method of the present disclosure, the term LVH may also include concentric or eccentric hypertrophy. It is known that treatment of arterial hypertension will cause LVH to regress. Treatment with antihypertensive drugs has been shown to cause LVH regression. With regression, left ventricular function usually improves and cardiovascular morbidity decreases.

The present disclosure refers to a subject who is known to bear at least one risk factor as specified elsewhere in the present application for developing heart failure and who has entered into the state of functional and/or structural abnormalities of the heart preceding heart failure. The functional and/or structural abnormality can be an early or a late functional and/or structural abnormality of the heart preceding heart failure.

In an embodiment of the present disclosure, the individual has previously been classified into stage A and has entered into functional and/or structural abnormalities of the heart preceding heart failure (late stage B). In an exemplary embodiment, the individual is about to enter into functional and/or structural abnormalities of the heart preceding heart failure (early stage B).

Accordingly, the method of the present disclosure permits to identify individuals suffering from any functional and/or structural abnormalities of the heart typically preceding left ventricular hypertrophy and typically preceding heart failure, including those with advanced structural heart disease typical for advanced stage B.

Individuals having entered into functional and/or structural abnormalities of the heart preceding heart failure typically proceed to heart failure via suffering from one or more of the following structural abnormalities of the heart which are known to precede heart failure. The list below includes early and late stages of functional and/or structural abnormalities of the heart. The individuals may belong to class B of the ACC/AHA classification including early and late stages of stage B: systolic and diastolic irregularities; geometric chamber distortion; left ventricular enlargement; cardiac remodeling; left ventricular hypertrophy; concentric hypertrophy, left ventricular fibrosis; left ventricular hypocontractility; asymptomatic valvular heart disease; regional wall-motion abnormality, left ventricular systolic dysfunction, for example with a LVEF of ≤50%; left ventricular diastolic dysfunction (DD), for example mild DD as an abnormal relaxation without increased LV end-diastolic filling pressure (decreased E/A ratio<0.75) or moderate or pseudonormal" DD as an abnormal relaxation with increased LV≤end-diastolic filling pressure (E/A 0.75 to 1.5, deceleration time>140 ms, and 2 other Doppler indices of elevated LV end-diastolic filling pressure); DD as myocardial dysfunction with preserved ejection fraction, cardiac dysfunction as six minutes walk test, cardiac dysfunction as detectable with coronary catheterization; previous myocardial infarction.

According to some embodiments, the functional and/or structural abnormalities of the heart preceding heart failure as referred to herein are early (early stage) functional and/or structural abnormalities. According to some embodiments, early (early stage) functional and/or structural abnormalities of the heart precede heart failure and left ventricular hypertrophy.

In the context of the present disclosure, early stage functional and/or structural abnormalities of the heart preceding heart failure individuals (for example early stage B) in general suffer from at least one of the following functional and/or structural abnormalities of the heart: functional and/or structural damage of the myocardium, epicardium, valves, or coronary circulation; impaired pumping or filling capacity, often a systolic or a diastolic impairment; change in the geometry of the left ventricle; hypertension associated with geometric chamber distortion; hypertension associated with left ventricular structural changes without developing or developed left ventricular hypertrophy, hypertension associated with increased septum diameter (or septum enlargement) without hypertrophy; hypertension associated with increased posterial wall diameter, hypertension associated with concentric increased myocardial enlargement, hypertension associated with eccentric increased myocardial enlargement, asymptomatic diastolic left ventricular dysfunction with preserved left ventricular ejection fraction (LVEF), in particular a LVEF of >50%.

In an exemplary embodiment, the functional and/or structural abnormality of the heart preceding heart failure and/or left ventricular hypertrophy is at least one abnormality selected from: left ventricular structural changes, an increased septum diameter (and/or septum enlargement), in particular hypertension associated with increased septum diameter (or septum enlargement), increased posterial wall diameter, in particular hypertension associated with increased posterial wall diameter, and diastolic dysfunction, in particular with preserved ejection fraction.

According to some embodiments, the diastolic dysfunction is asymptomatic diastolic left ventricular dysfunction with preserved left ventricular ejection fraction (LVEF), in particular a LVEF of >50%.

Thus, an exemplary structural abnormality of the heart preceding heart failure and/or left ventricular hypertrophy is selected from left ventricular structural changes, an increased septum diameter (and/or septum enlargement), and increased posterial wall diameter.

Thus, an exemplary functional abnormality of the heart preceding heart failure is diastolic dysfunction, in particular diastolic dysfunction with preserved ejection fraction.

According to some embodiments, the septum diameter is increased (and/or the septum is enlarged), if the septum wall is thicker than 11 mm. According to some embodiments, the septum diameter is increased (and/or the septum is enlarged) if the thickness of the septum wall is larger than 11 but lower than 16 mm, or if the thickness is between 12 and 16 mm, for example.

According to some embodiments, the posterial wall diameter is increased, if the posterial wall is thicker than 11 mm. According to some embodiments, the posterial wall diameter is increased if the thickness of the posterial wall is larger than 11 but lower than 16 mm, or if the thickness is between 12 and 16 mm, for example.

According to some embodiments of the present disclosure, the patient having early stage functional and/or structural abnormalities of the heart preceding heart failure (early stage B) shows the following risk factors of suffering from heart failure: history of cigarette smoking, obesity, metabolic syndrome, diabetes type 1 and type 2, arterial hypertension. Thus, the subject may be suffering from hypertension, diabetes, obesity, metabolic syndrome and/or a history of smoking (and, thus, has a history of smoking). In an exemplary embodiment, the subject suffers from hypertension and/or diabetes.

Diastolic Dysfunction.

According to some embodiments of the present disclosure, the method permits to diagnose asymptomatic diastolic dysfunction in the individual having early stage functional and/or structural abnormalities of the heart preceding heart failure (early stage B). The individual may also suffer from systolic dysfunction. Furthermore, the individual may suffer from morphological changes in its left ventricle. According to some embodiments, the individual suffering from diastolic dysfunction does not suffer from a reduced left ventricular ejection fraction LVEF (i.e. the individual has a preserved LVEF). In an exemplary embodiment, the individual suffering from diastolic dysfunction does not suffer from systolic dysfunction. The individual, in particular, does not suffer from left ventricular hypertrophy LVH.

According to some embodiments of the present disclosure, the patient having early stage functional and/or structural abnormalities of the heart preceding heart failure (early stage B) and suffering from diastolic dysfunction, as specified in the preceding paragraph, shows at least one of the following risk factors of suffering from heart failure: history of cigarette smoking, obesity, metabolic syndrome, diabetes type 1 and type 2, arterial hypertension, in particular arterial hypertension.

Heart Failure.

Heart failure is a condition that can result from any structural or functional cardiac disorder that impairs the ability of the heart to fill with or pump a sufficient amount of blood throughout the body. Heart failure is a chronic disease; it can, inter alia, occur either following an acute cardiovascular event (like myocardial infarction), or it can occur e.g. as a consequence of inflammatory or degenerative changes in myocardial tissue.

Functional and/or structural functional and/or structural abnormalities of the heart and heart failure often remain undiagnosed, particularly when the condition is considered "mild". A patient having heart failure, however, will not be able to fully restore his health. Even with the best therapy, heart failure is associated with an annual mortality of about 10%.

The term "heart failure" as used herein relates to an impaired systolic and/or diastolic function of the heart being accompanied by overt signs of heart failure as known to the person skilled in the art. According to some embodiments, heart failure referred to herein is also chronic heart failure. Heart failure according to the present disclosure includes overt and/or advanced heart failure. In overt heart failure, the subject shows symptoms of heart failure as known to the person skilled in the art.

The term "heart failure" as used herein refers to stages C and D of the ACC/AHA classification; in these stages, the subject shows typical symptoms of heart failure. i.e. the subject is not apparently healthy. The subject having heart failure and being classified into stage C or D has undergone permanent, non reversible structural and/or functional changes to his myocardium, and as a consequence of these changes, full health restoration is not possible. A subject having attained stage C or even D of the ACC/AHA classification cannot go back to stage B or even A.

Permanent structural or functional damages to the myocardium which are typical for heart failure are known to the person skilled in the art and include a variety of molecular cardiac remodelling processes, such as interstitial fibrosis, inflammation, infiltration, scar formation, apoptosis, necrosis.

A stiffer ventricular wall due to interstitial fibrosis causes inadequate filling of the ventricle in diastolic dysfunction. Permanent structural or functional damages to the myocardium are caused by dysfunction or destruction of cardiac myocytes. Myocytes and their components can be damaged by inflammation or by infiltration. Toxins and pharmacological agents (such as ethanol, cocaine, and amphetamines) cause intracellular damage and oxidative stress. A common mechanism of damage is ischemia causing infarction and scar formation. After myocardial infarction, dead myocytes are replaced by scar tissue, deleteriously affecting the function of the myocardium. On echocardiogram, this is manifest by abnormal or absent wall motion.

Manifestations (symptoms) of HF are dyspnea and fatigue and fluid retention, which may lead to pulmonary congestion and peripheral edema, typical signs on the physical examination are edema and rales. There is no single diagnostic test for HF because it is largely a clinical diagnosis that is based on a careful history and physical examination.

The clinical syndrome of HF may result from disorders of the pericardium, myocardium, endocardium, or great vessels, but the majority of patients with HF suffers from an impairment of LV myocardial function. Heart failure may be associated with a wide spectrum of LV functional abnormalities, ranging from e.g. normal LV size and preserved EF to severe dilatation and/or markedly reduced EF. In most patients, abnormalities of systolic and diastolic dysfunction coexist. Patients with normal EF may have a different natural history and may require different treatment strategies than patients with reduced EF. The various alterations of systolic and diastolic function seen with LVH obviously can progress into congestive heart failure (CHF).

Systolic and diastolic heart failure can be diagnosed by methods known to the person skilled in the artsuch as by echocardiography or tissue Doppler echocardiography (TD). In general, systolic heart failure is apparent by a reduced left ventricular ejection fraction (LVEF). In an embodiment of the present disclosure, heart failure as used herein is accompanied by a left ventricular ejection fraction (LVEF) of less than 50% or midwall fractional shortening (MFS)<15%.

Diastolic heart failure (DHF) is supposed to account for more than 50% of all heart failure patients and is also referred to as heart failure with normal LVEF ejection fraction (HFNEF). The diagnosis of HFNEF requires the following conditions to be satisfied: (i) signs or symptoms of heart failure; (ii) normal or mildly abnormal systolic LV function; (iii) evidence of diastolic LV dysfunction. Normal or mildly abnormal systolic LV function implies both an LVEF>50% and an LV end-diastolic volume index (LVEDVI)<97 mL/m$^2$. Diastolic LV dysfunction is preferably diagnosed by tissue Doppler (TD), wherein a ration E/E'>15 is regarded as diagnostic evidence for diastolic LV dysfunction (E being early mitral valve flow velocity; and E' being early TD lengthening velocity) If TD yields an E/E' ratio suggestive of diastolic LV dysfunction (15>E/E'>8), additional non-invasive investigations are required for diagnostic evidence of diastolic LV dysfunction. (e.g. Doppler of the lateral mitral annulus, Doppler of mitral valve or pulmonary veins, echo measures of LV mass index or left atrial volume index, electrocardiographic evidence of atrial fibrillation). For more detailed information on diastolic LV dysfunction, reference is made to the Consensus statement on the diagnosis of heart failure with normal left ventricular ejection fraction by the Heart Failure and Echocardiography Associations of the European Society of Cardiology, European Heart Journal 2007, 28, 2359-2550.

Risk Factors.

In general, prior to carrying out the methods of the present disclosure, the respective individual is diagnosed for risk factors of developing heart failure. Risk factors are known to the person skilled in the art and include the following: hypertension; age, systolic and diastolic hypertension; coronary artery disease (CAD); subclinical organ damage, e.g. of the heart, brain, kidneys, blood vessels; obesity, such as obesity defined as body mass index BMI<25 kg/m$^2$; adipositas; metabolic syndrome; diabetes mellitus type 1 or type 2, in particular type 2 diabetes mellitus; type 1 diabetes with microalbuminuria, cigarette smoking; history of revascularization; history of cardiotoxic drug therapy or alcohol abuse; dyslipidemia; total cholesterol, total cholesterol/ HDL-cholesterol ratio, personal history of rheumatic fever; family history of cardiomyopathy.

It is to be understood that the above list is not exhaustive. A more exhaustive citation of risk factors is found in the 2007 Guidelines for the Management of Arterial Hypertension, European Heart Journal (2007) 28, 1462-1536 which is incorporated herein in its entirety in respect to the risk factors, in particular tables 1, 2 and 3 and FIG. 1.

Individual risk factors comprise the risk of CVD and of developing fatal atherosclerotic events, which is calculated using the SCORE system available from the European Society of Hypertension (European Society of Hypertension Scientific Newsletter 2010, 11, No 48). According to the recommended scoring system of the ESC of Hypertension based on the number and levels of risk factors different risk groups are formed (low, low-moderate . . . ) and accordingly therapy is adapted. The disclosure of the European Society of Hypertension Scientific Newsletter 2010, 11, No 48 is incorporated by reference in its entirety in the present application.

The term "subclinical organ damage" as used herein refers to a pathophysiological state (damage) of an organ. The term is known to the person skilled in the art. Subclinical organ damage may be caused by various reason, e.g. by one or more risk factors of suffering from heart failure as specified above, in particular arterial hypertension, does not give rise to clinical symptoms and cannot be recognized by the person skilled in the art without referring to an established diagnostic method (e.g. cardiac hypertrophy, low grade albuminuria, pulse wave velocity, . . . ). For a more detailed definition of subclinical organ damage, reference is made to the European Heart Journal (2007) 28, 1462-1536 which is incorporated herein in its entirety in respect to the risk factors, in particular chapter 3.6 including box 7.

It is to be understood that the above list is not exhaustive. Furthermore, the respective individual may show one risk factor, or 2 or even more risk factors. For example, it is known that diabetes mellitus in general triggers CAD and/or hypertension; coronary artery disease, irrespective of the existence of diabetes mellitus, often leads to hypertension.

An individual suffering from one or more of the risk factors as specified beforehand and not having symptoms of heart failure (apparently healthy) will in general and may be classified into ACC/AHA stage A in case no functional and/or structural abnormalities of the heart preceding heart failure is diagnosed in the individual.

It is important to note that the criteria are not ambiguous and the classification of an individual may vary depending on the physician carrying out examination. The first criterium for the classification of an individual in stage A (and also in stages B, C and D) of the ACC/AHA classification is the description of the patient (see the above definition of the ACC/AHA classification, as taken from the original publication of the Guidelines). The examples for risk factors/ pathophysiological state of each stage cannot be exhaustive, as becomes clear from an inspection of the original publications. This means that, in the context of the present disclosure, an individual will in general and may be classified into stage A of the ACC/AHA classification even in case the risk factors which the individual bears are not explicitly cited in the guidelines.

In an embodiment of the present disclosure, the individual bearing risk factors of developing heart failure is an individual which has been classified into ACC/AHA stage A prior to carrying out the methods according to the present disclosure. The individual classified in stage A may have experienced physiological changes towards pathophysiological states belonging to ACC/AHA stage B (i.e. functional and/or structural abnormalities of the heart preceding heart failure). In the context of the present disclosure, this state is referred to as "early stage of functional and/or structural abnormalities of the heart preceding heart failure" (early stage B) and is different from a "late stages of functional and/or structural abnormalities of the heart preceding heart failure" (late stage B). According to some embodiments, the individual does not show obvious symptoms of heart failure. According to some embodiments the individual does not show left ventricular hypertrophy (i.e. the individual is apparently healthy).

As the individual, in some cases, does not show obvious or overt signs of heart failure a (for example, of left ventricular hypertrophy, i.e. the individual is apparently healthy) the physiological changes which may have occurred are not diagnosed without carrying out a detailed diagnosis, either with the methods known in the art (which are onerous, costly and time-consuming) or with the methods of the present disclosure.

According to some embodiments, the subject suffers from hypertension, in particular from arterial hypertension. In the context of the present disclosure, an individual suffering from hypertension will be referred to as "hypertensive individual". The hypertension can be any form of hypertension known to the person skilled in the art. Non-limiting examples include subjects suited for anti-hypertensive medication due to their cardiovascular risk profile according to the recommendations of the guidelines as well as subjects already at anti-hypertensive medication. In this respect, reference is made to the 2007 Guidelines for the Management of Arterial Hypertension, European Heart Journal (2007) 28, 1462-1536 and the European Society of Hypertension Scientific Newsletter 2010, 11, No 48).

According to some embodiments of the present disclosure, the individual suffers from arterial hypertension, systolic and/and or diastolic hypertension. Hypertension may be accompanied by one or more of the above-referenced further risk factors. Thus, a subject bearing risk factors of heart failure may suffer from hypertension accompanied by one or more of the above-referenced further risk factors. However, it is also contemplated that said subject suffers from hypertension alone.

In another embodiment of the present disclosure, the individual suffers from diabetes mellitus, in particular diabetes mellitus type 2. In yet another embodiment, the individual suffers from obesity. In yet another embodiment, the individual suffers from metabolic syndrome. In yet another embodiment the individual suffers from low, moderate, high or very high risk according to the risk chart of the European Society of Hypertension.

Diagnosis of risk factors generally occurs by methods known to the person skilled in the art, in general cardiac auscultation and/or ECG and/or chest x-ray and/or echocardiography, tissue Doppler echocardiography, coronary catheterization, determination of blood pressure, determination of pulse wave velocity, determination of intima media thickness, determination of diabetes mellitus, determination of metabolic syndrome, determination of body mass index, determination of smoking habitus, determination of total cholesterol, determination of LDL-cholesterol, determination of blood glucose determination of cardiovascular risk profile according to risk chart of the European Society of Hypertension and according to the Guidelines for the Management of Arterial Hypertension, European Heart Journal (2007) 28, 1462-1536 and the European Society of Hypertension Scientific Newsletter 2010, 11, No 48).

In another embodiment one or more of the additional diagnostic steps cited beforehand are a part of the present disclosure, i.e. these additional steps may be carried out in addition to the method of the present disclosure making use of a cardiac troponin or a variant thereof for diagnosing functional and/or structural abnormalities of the heart preceding heart failure. This also applies for the other methods of the present disclosure.

Accordingly, the present disclosure relates to a method of diagnosing in a subject functional and/or structural abnormalities of the heart preceding heart failure, based on the diagnosis of risk factors of developing heart failure by a method or methods known to the person skilled in the art and, furthermore, comparison of the concentrations of at least on cardiac troponin or a variant thereof, and optionally of one or more other markers of heart failure, to the concentration of this or these marker(s) in a control sample.

The method of the disclosure may comprise the following steps:
a) diagnosing risk factors of developing heart failure by a method or methods known to the person skilled in the art,
b) measuring in a sample obtained from the subject the concentration of at least one cardiac troponin or a variant thereof; c) optionally measuring in the sample the concentration of one or more other marker(s) of heart failure; and d) assessing the said functional and/or structural abnormalities by comparing the concentration determined in step (a) and optionally the concentration(s) determined in step (b) to the concentration of this marker or these markers to reference amounts, e.g. to the concentration of this marker or these markers as established in a control sample.

The present disclosure provides a method of diagnosing in a subject functional and/or structural abnormalities of the heart preceding heart failure, the method comprising the steps of
a) diagnosing risk factors of developing heart failure by a method or methods known to the person skilled in the art,
b) measuring in a sample obtained from the subject the concentration of at least one cardiac troponin or a variant thereof,
c) optionally measuring in the sample the concentration of one or more other marker(s) of heart failure, and
d) assessing the said functional and/or structural abnormalities by comparing the concentration determined in step (a) and optionally the concentration(s) determined in step (b) to reference amounts.

The methods known to the person skilled in the art are the following: cardiac auscultation and/or ECG and/or chest x-ray and/or echocardiography, tissue Doppler echocardiography, coronary catheterization, determination of blood pressure, determination of pulse wave velocity, determination of intima media thickness, determination of diabetes mellitus, determination of metabolic syndrome, determination of body mass index, determination of smoking habitus, determination of total cholesterol, determination of LDL-cholesterol, determination of blood glucose determination of cardiovascular risk profile according to risk chart of the European Society of Hypertension and according to the Guidelines for the Management of Arterial Hypertension, European Heart Journal (2007) 28, 1462-1536 and the European Society of Hypertension Scientific Newsletter 2010, 11, No 48).

In the above method, step a) and step b), or step a) and steps b) to d) can be carried out simultaneously (i.e. at the same point in time) or subsequently (i.e. at different points in time). In case the steps are carried out subsequently, the time interval between the steps is not long enough to allow a change in the pathophysiological state of the subject.

In accordance with the present disclosure, an increased concentration of cardiac troponin or a variant thereof, in particular troponin T or a variant thereof is indicative for functional and/or structural abnormalities of the heart preceding heart failure. The subject bears risk factors of developing heart failure, for example, and may be an asymptomatic subject, or may be suffering from left ventricular dysfunction (LVD), diastolic left ventricular dysfunction, or even diastolic left ventricular dysfunction with preserved left ventricular systolic function. For example, the individual has not developed LVH (i.e. LVH is not apparent). A decreased concentration of a cardiac troponin, such as troponin T or a variant thereof or Troponin I or a variant thereof, which is indicative for the absence of heart disease.

In accordance with the foregoing, troponin T concentrations of ≥(equal to or higher than) about 5.0 pg/mL, ≥ about 6.0 pg/mL, or ≥ about 7.0 pg/mL are increased troponin T concentrations which are indicative for functional and/or structural abnormalities of the heart preceding heart failure and/or preceding left ventricular hypertrophy, as laid out in the preceding paragraph. Moreover troponin T concentrations of equal to or higher than about 3.3 pg/ml or of equal or higher than about 3.5 pg/ml are increased troponin T concentrations which are indicative for functional and/or structural abnormalities of the heart preceding heart failure and/or left ventricular hypertrophy.

Moreover, troponin I concentrations of equal or higher than 0.2-9.0 pg/ml, or of equal to or higher than about 9 pg/ml are increased troponin I concentrations which are indicative for functional and/or structural abnormalities of the heart preceding heart failure and/or left ventricular hypertrophy. A concentration of a cardiac troponin, such as troponin T or I, lower of the aforementioned concentrations, is indicative for the absence of functional and/or structural abnormalities of the heart preceding heart failure and/or left ventricular hypertrophy.

In the studies carried out in the context of the present disclosure, it was surprisingly found, that an increase of a cardiac troponin, in particular of troponin T, that is at least 20% or of at least 30% larger than the amount of a cardiac troponin, in particular of troponin T, is indicative for the diagnosis of functional and/or structural abnormalities preceding heart failure and/or preceding left ventricular hypertrophy. According to the explanation of the terms "decreased" or "increased", as used in the context of the present disclosure, denotes with an increase or decrease of at least 10%, of at least 20%, at least 30%, in respect to the amount/concentration of the marker in a sample from a healthy individual/subject and/or from healthy individuals/ subjects. In respect to reference amounts no increase of Nt-ProBNP was observed in the in the subjects belonging to groups 1 to 3 described in Example 1.

In the studies carried out in the context of the present disclosure, it was further surprisingly found, that an increase of a cardiac troponin, such as of troponin T, in a sample that is derived from a female subject that is at least 30%, or more or at least 50% larger than the amount of a cardiac troponin, in particular of troponin T, in a sample of a healthy female subject (or group of healthy female subjects) is indicative for the diagnosis of functional and/or structural abnormalities preceding heart failure and/or preceding left ventricular hypertrophy.

If the amount of troponin T is measured, the reference amount serving as a cut-off is within a range of 2 to 14 pg/ml. According to some embodiments, the reference amount, serving as cut-off for Troponin is within a range of 3.2 to 4 pg/ml. According to some embodiments reference amounts of troponin T that may serve as cut-off amount include, 3.2, 3.4 and 4.2 pg/ml. According to some embodiments a reference amount of troponin I that may serve as cut-off amount is 9.0 pg/ml. An amount of a cardiac troponin in sample, such as in a serum or plasma sample, of a subject larger than the reference amount, is indicative for the diagnosis of functional and/or structural abnormalities preceding heart failure and/or preceding left ventricular hypertrophy. An amount of a cardiac troponin in sample, for example a serum or plasma sample, of subject lower than the reference amount, indicates that the subject has no functional and/or structural abnormalities preceding heart failure and/or preceding left ventricular hypertrophy.

The above values were established using Roche's electrochemiluminescence ELISA sandwich test Elecsys™ Troponin T hs (high sensitive) STAT (Short Turn Around Time) assay, as specified in the examples, under "Methods". Moreover, it has been found that each of said biomarkers is statistically independent from each other.

The present disclosure relates to a method which permits to diagnose or assess or evaluate if a subject who is bearing risk factors for heart failure only bears risk factors or if the risk factors have developed into functional and/or structural abnormalities of the heart preceding heart failure.

An individual suffering from functional and/or structural abnormalities of the heart preceding heart failure as specified beforehand and not having symptoms of heart failure (apparently healthy) will in general be classified into ACC/AHA stage B in case heart failure is not diagnosed in the individual. According to the instant disclosure, the criteria are not ambiguous and the classification of an individual may vary depending on the physician carrying out examination. The first criterium for the classification of an individual in stage B (and also in stages A, C and D) of the ACC/AHA classification is the description of the patient (see the above definition of the ACC/AHA classification, as taken from the original publication of the Guidelines). The examples for risk factors/pathophysiological state of each stage cannot be exhaustive, as becomes clear from an inspection of the original publications. According to the present disclosure, an individual will in general and may be classified into stage B of the ACC/AHA classification even in case functional and/or structural abnormalities of the heart preceding heart failure which the individual bears is not explicitly cited in the guidelines.

The proteins which are measured in the context of the present disclosure can be measured in one single sample or various samples of the subject, e.g. 2, 3, 4 or 5 samples. The samples may be obtained at the same time or at different time points. For example, the samples may be collected before and/or during and/or after therapy of the patient.

According to some embodiments, the cardiac troponin is troponin T or a variant thereof or troponin I or a variant thereof. In further embodiments of the present disclosure, at least one further marker to the marker selected from cardiac troponins, namely at least on further marker of heart failure, is used in the methods of the present disclosure. The at least one marker of heart failure is selected from GDF-15 and variants thereof and IGFBP7 and variants thereof. In an embodiment of the present disclosure, the cardiac troponin is selected from troponin T and variants thereof and troponin I and variants thereof, in particular the cardiac troponin is troponin T or a variant thereof. In one embodiment of the present disclosure, the following markers are determined in combination: the cardiac troponin is selected from troponin T and troponin I and variants thereof, in particular the cardiac troponin is troponin T or a variant thereof; GDF-15 or a variant thereof; and IGFBP7 or a variant thereof.

The term "diagnosing" as used herein means assessing, identifying, evaluating or classifying if a subject suffers from functional and/or structural abnormalities of the heart preceding heart failure. The term "diagnosing" also refers to distinguishing between a subject only bearing risk factors of developing heart failure, or already suffering from functional and/or structural abnormalities of the heart preceding heart failure.

The person skilled in the art is aware of methods to diagnose if a subject suffers from functional and/or structural abnormalities of the heart preceding heart failure or is about to develop functional and/or structural abnormalities of the heart preceding heart failure, where the subject is classified into ACC/AHA stage A. This diagnosis is in general costly, time-consuming and requires medical skill and experience. Methods of evaluation are known to the person skilled in the art and are typically based on medical history, further evaluation includes examination using diagnostic apparatuses/devices (cardiac auscultation, ECG, echocardiography, chest x-ray, radionuclide imaging, ventriculography, CT scan, MRI and/or stress testing, coronary angiography, ultrasonography, coronary catheterization). Other tests may be done as needed to determine the cause. Treatment depends on the specific type and severeness of the functional and/or structural abnormalities of the heart preceding heart failure.

For example, a preliminary diagnosis of left ventricular hypertrophy can usually be made based on the results of a physical examination. The heart sounds heard through a stethoscope are usually characteristic. Echocardiography is the best way to confirm the diagnosis. Electrocardiography (ECG) and a chest x-ray are also helpful. Cardiac catheterization, an invasive procedure, is performed to measure pressures in the heart chambers only if surgery is being considered.

The diagnostic methods listed above can be used supplementary/complementary with the methods of the present disclosure based on the determination of the cited markers.

The markers (peptides) which are used in the present disclosure can also be used, in further embodiments of the present disclosure, for the confirmation of a diagnosis established by a conventional diagnostic method known in the art, and vice versa. Accordingly, the present disclosure also relates to a method of confirming a diagnosis which is not or only partly-based on the determination of the markers used in the present disclosure, by determining the concentration of the markers used in the present disclosure, comparing these to the concentration of said marker in a control sample, and confirming or not confirming the diagnosis obtained by methods according to the state of the art.

Confirmation.

In a further embodiment, the present disclosure relates to a method of confirming in a subject functional and/or structural abnormalities of the heart preceding heart failure, based on the diagnosis of risk factors of developing heart failure by a method or methods known to the person skilled in the art and, furthermore, comparison of the concentrations of at least on cardiac troponin or a variant thereof, and optionally of one or more other markers of heart failure, to the concentration of this or these marker(s) in a control sample.

The method of the disclosure may comprise the following steps:
   a) diagnosing risk factors of developing heart failure by a method or methods known to the person skilled in the art,
   b) measuring in a sample obtained from the subject the concentration of at least one cardiac troponin or a variant thereof;
   c) optionally measuring in the sample the concentration of one or more other marker(s) of heart failure; and
   d) confirming the said functional and/or structural abnormalities by comparing the concentration determined in step (a) and optionally the concentration(s) determined in step (b) to reference amounts, e.g. to the concentration of this marker or these markers as established in a control sample.

Accordingly, the present disclosure provides a method of confirming in a subject functional and/or structural abnormalities of the heart preceding heart failure, the method comprising the steps of:
   a) diagnosing in the subject risk factors of developing heart failure by a method or methods known to the person skilled in the art,
   b) measuring in a sample obtained from the subject the concentration of at least one cardiac troponin or a variant thereof,
   c) optionally measuring in the sample the concentration of one or more other marker(s) of heart failure, and
   d) confirming the said functional and/or structural abnormalities by comparing the concentration determined in step (a) and optionally the concentration(s) determined in step (b) to reference amounts.

The methods known to the person skilled in the art generally use diagnostic apparatuses/devices and are selected from the following: transvenous endomyocardial biopsy, cardiac catheterization, cardiac auscultation, ECG, echocardiography, chest x-ray, radionuclide imaging, ventriculography, CT scan, MRI and/or stress testing, coronary angiography, ultrasonography, In the above method, step a) and step d), or steps a) to c) and step d) can be carried out simultaneously (i.e. at the same point in time) or subsequently (i.e. at different points in time). In case the steps are carried out subsequently, the time interval between the steps is not long enough to allow a change in the pathophysiological state of the subject.

As already mentioned beforehand, more than one pathomechanism may be the cause for the occurrence of pathological left ventricular hypertrophy in a subject.

Risk Prediction.

In a further embodiment, the present disclosure provides a method of predicting the risk of a subject to suffer from heart failure, or respective cardiovascular and renal events preceding heart failure, based on the comparison of the concentrations of at least on cardiac troponin or a variant thereof, and optionally of one or more other markers of heart failure, to the concentration of this or these marker(s) in a control sample.

The method of the disclosure may comprise the following steps:
   a) measuring in a sample obtained from the subject the concentration of at least one cardiac troponin or a variant thereof;
   b) optionally measuring in the sample the concentration of one or more other marker(s) of heart failure; and
   c) predicting the risk of the subjects to suffer from heart failure or from cardiovascular and renal events, by comparing the concentration determined in step (a) and optionally the concentration(s) determined in step (b) to reference amounts, e.g. to the concentration of this marker or these markers as established in a control sample.

Accordingly, the present disclosure provides a method of predicting the risk of a subject to suffer from heart failure, or respective cardiovascular and renal events preceding heart failure, the method comprising the steps of:
   a) measuring in a sample obtained from the subject the concentration of at least one cardiac troponin or a variant thereof,
   b) optionally measuring in the sample the concentration of one or more other marker(s) of heart failure, and
   c) predicting the risk of the subjects to suffer from heart failure or from cardiovascular and renal events by comparing the concentration determined in step (a) and optionally the concentration(s) determined in step (b) with a reference amount.

The above method of predicting may comprise an optional step bb) of diagnosing functional and/or structural abnormalities of the heart preceding heart failure. This step bb) may identify any of the heart diseases cited beforehand, including for example those found in early stage functional and/or structural abnormalities of the heart preceding heart failure.

According to some embodiments of the present disclosure, the individual is an individual for whom the risk of suffering from heart failure is determined is an individual wherein LVH is not apparent.

Method of Predicting Prior to LVH.

Therefore, in a further embodiment, the present disclosure provides a method of predicting the risk of heart failure in a subject before left ventricular hypertrophy (LVH) is apparent, based on the comparison of the concentrations of at least on cardiac troponin or a variant thereof, and optionally of one or more other markers of heart failure, to the concentration of this or these marker(s) in a control sample.

The method of the disclosure may comprise the following steps: a) measuring in a sample obtained from the subject the concentration of at least one cardiac troponin or a variant thereof; b) optionally measuring in the sample the concentration of one or more other marker(s) of heart failure; and c) predicting the risk of the subjects to suffer from heart failure by comparing the concentration determined in step (a) and optionally the concentration(s) determined in step (b) to reference amounts, e.g. to the concentration of this marker or these markers as established in a control sample.

Accordingly, the present disclosure provides a method of predicting the risk of heart failure in a subject before left ventricular hypertrophy (LVH) is apparent, the method comprising the steps of:
   a) measuring in a sample obtained from the subject the concentration of at least one cardiac troponin or a variant thereof, b) optionally measuring in the sample the concentration of one or more other marker(s) of heart failure, and c) predicting the risk of the subjects to suffer from heart failure by comparing the concentration determined in step (a) and optionally the concentration(s) determined in step (b) to reference amounts.

The subject may bears risk factors for heart failure, e.g. hypertension and diabetes. Also according to some embodiments, the subject does not show overt signs and/or symptoms of heart failure.

Diastolic Dysfunction.

According to some embodiments of the present disclosure, the above method permits to predict the risk of suffering from heart failure in an individual having early stage functional and/or structural abnormalities of the heart preceding heart failure (early stage B) and suffering from asymptomatic diastolic dysfunction. The individual may also suffer from systolic dysfunction. Furthermore, the individual may suffer from morphological changes in its left ventricle. According to some embodiments, the individual suffering from diastolic dysfunction does not suffer from a reduced left ventricular ejection fraction LVEF (i.e. the individual has a preserved LVEF). According to some embodiments, the individual suffering from diastolic dysfunction does not suffer from systolic dysfunction. The individual, for example, may not suffer from left ventricular hypertrophy LVH.

According to some embodiments of the above method, the patient having early stage functional and/or structural abnormalities of the heart preceding heart failure (early stage B) and/or suffering from diastolic dysfunction, as specified in the preceding paragraph, shows the following risk factors of suffering from heart failure: history of cigarette smoking, obesity, metabolic syndrome, diabetes type 1 and type 2, arterial hypertension, in particular arterial hypertension.

In case of a prediction in a subject having a diastolic dysfunction, the method of prediction according to the disclosure may comprise an optional step bb) of diagnosing (asymptomatic) diastolic dysfunction. This step bb) may identify any of the functional and/or structural abnormalities of the heart cited beforehand, including for example those found in early stage functional and/or structural abnormalities of the heart preceding heart failure.

It is known in the art that individuals having a diastolic dysfunction are predisposed to suffer from heart failure as a consequence of the diastolic dysfunction. This is published, for example, in; *Med Clin North Am.* 2009 May; 93(3):647-64; *Am J Hypertens.* 2001 February; 14(2):106-13; Hypertension. 2002; 40:136-14.

Prediction of Early Stage B.

According to some embodiments of the present disclosure, the above method permits to predict the risk of an individual having risk factors of developing heart failure (stage A) to suffer from functional and/or structural abnormalities of the heart preceding heart failure (stage B) and/or preceding left ventricular hypertrophy. According to some embodiments of the above method, the risk to suffer from a left ventricular dysfunction, in particular a diastolic dysfunction, of the individual having risk factors is predicted. According to some embodiments, the individual suffering from diastolic dysfunction does not suffer from a reduced left ventricular ejection fraction LVEF (i.e. the individual has a preserved LVEF). In some embodiments, the individual suffering from diastolic dysfunction does not suffer from systolic dysfunction. In further embodiments of the above method, the risk to suffer from a structural change of the left ventriculum is predicted. In particular, the risk is predicted before the individual suffers from LVH (i.e. the risk of an individual having risk factors of developing heart failure (stage A) to suffer from early stage functional and/or structural abnormalities of the heart (early stage B) typically preceding heart failure left ventricular hypertrophy (late stage B), is predicted.

According to some embodiments of the above method, the subject having risk factors of suffering from heart failure (stage A) or to suffer from functional and/or structural abnormalities of the heart preceding heart failure (stage B), as specified in the preceding paragraphs, shows the following risk factors of suffering from heart failure: history of cigarette smoking, obesity, metabolic syndrome, diabetes type 1 and type 2, arterial hypertension, in particular arterial hypertension.

In case of a prediction in a subject having a diastolic dysfunction, the method of prediction according to the disclosure may comprise an optional step bb) of diagnosing (asymptomatic) diastolic dysfunction. This step bb) may identify any of the functional and/or structural abnormalities of the heart cited beforehand, including those found in early stage functional and/or structural abnormalities of the heart preceding heart failure.

Method of Predicting the Risk of a Female Subject to Suffer from LVH.

The definitions and explanation given herein, may apply mutatis mutandis to the following:

Moreover, the present disclosure relates to a method of predicting the risk of a female subject to suffer from left ventricular hypertrophy, the method comprising the steps of:

a) measuring in a sample obtained from the subject the concentration of at least one cardiac troponin or a variant thereof, b) optionally measuring in the sample the concentration of one or more other marker(s) of heart failure, and c) predicting the risk of the subjects to suffer from left ventricular hypertrophy by comparing the concentration determined in step (a) and optionally the concentration(s) determined in step (b) with a reference amount.

The method of the present disclosure, is an ex vivo method. Moreover, it may comprise steps in addition to those explicitly mentioned above. For example, further steps may relate to sample pre-treatments or evaluation of the results obtained by the method. The method may be carried out manually or assisted by automation. The steps may in total or in part be assisted by automation, e.g., by a suitable robotic and sensory equipment for the determination or a computer-implemented comparison based on said comparison. According to some embodiments, the method is carried out entirely in an automated manner. In such a case, the prognostic result which is established in step c) is generated in a suitable output format so that it can be used as an aid for establishing the final clinical prognosis by, e.g., a medical practitioner.

In the context of the aforementioned method of the present disclosure, the risk of a female subject to suffer from LVH shall be predicted. The term "predicting the risk" as used herein, may refer to assessing the probability according to which the female subject as referred to herein will suffer from left ventricular hypertrophy. According to some embodiments, the risk/probability to suffer from left ventricular hypertrophy within a certain time window is predicted. According to some embodiments of the present disclosure, the predictive window, for example, is an interval of at least 6 month, at least 9 month, at least 1 year, at least 2 years, at least 3 years, at least 4 years, at least 5 years, at least 10 years, at least 15 years or any intermitting time range. In a particular embodiment of the present disclosure, the predictive window, is an interval of 10 years, an in some cases of 5 years. According to some embodiments, said predictive window is calculated from the time point at which the sample to be tested has been obtained.

As will be understood by those skilled in the art, the aforementioned prediction is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Exemplary confidence intervals include at least 90%, at least 95%, at least 97%, at least 98% or at least 99%.

The term "predicting", according to some embodiments, relates to assessing whether a subject is at risk or not at risk to suffer from left ventricular hypertrophy (the term left ventricular hypertrophy has been defined elsewhere herein, the definition applies accordingly). According to some embodiments, it shall be assessed whether a female risk is at elevated risk or at reduced risk as compared to the average risk in a population of subjects. The term "predicting the risk to suffer from left ventricular hypertrophy" as used herein means that the subject to be analyzed by the method of the present disclosure is allocated either into the group of subjects being at risk to suffer from left ventricular hypertrophy, or into a group of subjects being not at risk to suffer from left ventricular hypertrophy. Having a risk to suffer from left ventricular hypertrophy as referred to in accordance with the present disclosure, means that the risk to suffer from left ventricular hypertrophy is increased (for example, within the predictive window). Said risk may be elevated as compared to the average risk in a cohort of female subjects, in particular in a cohort of subjects bearing at least one risk factor to suffer from heart failure (for example, the same risk factor(s) as the test subject). A subject who is not at risk to suffer from left ventricular hypertrophy as referred to in accordance with the present disclosure, may have a reduced risk to suffer from left ventricular hypertrophy (for example, within the predictive window). According to some embodiments, said risk is reduced as compared to the average risk in a cohort of female subjects, in particular in a cohort of subjects bearing at least one risk factor (for example, the same risk factor(s) as the test subject) to suffer from heart failure. A subject who is at risk to suffer from left ventricular hypertrophy may have a risk of 10-20%, or larger, or, for example of 20% or larger to suffer from left ventricular hypertrophy, for example, within a predictive window of 5 years. A subject who is not at risk to suffer from left ventricular hypertrophy, may have a risk to suffer from left ventricular hypertrophy of lower than 10%, and in some cases of lower than, 5% or lower even, within a predictive window of 10 years.

The term "subject" has been described elsewhere herein. The definition applies accordingly. The subject in accordance with the aforementioned method may be a female subject. According to some embodiments of the aforementioned method, the female subject to be tested shows at least one (and, thus, one or more than one) risk factor of suffering from heart failure. In particular, the female subject to be tested, may show at least one risk factor selected from the group consisting of history of cigarette smoking, obesity, metabolic syndrome, diabetes type 1 and type 2, and hypertension, in particular arterial hypertension. Thus, the female subject may, suffer from hypertension (in particular arterial hypertension), diabetes, obesity, metabolic syndrome and/or a history of smoking (i.e. the subject has history of smoking). In some particular embodiments, the female subject bearing at least one risk factor of heart failure suffers from hypertension (such as arterial hypertension) and/or diabetes.

The term "reference amount" has been described elsewhere herein. The definition applies accordingly. Moreover, the term "reference amounts" or "reference values" as used herein in the context of the aforementioned method refers to an amount of the polypeptides which allow to predict the risk to suffer from LVH. Therefore, the reference amounts will in general be derived from a subject known to be at risk to suffer from LVH or from a subject known to be at not at risk to suffer from LVH.

According to some embodiments, an increased amount for a cardiac troponin or a variant thereof as measured from a sample derived from a female subject to be tested indicates that the female subject is at risk to suffer from LVH. Also, an increased amount of GDF15 or a variant thereof and IGFBP7 or a variant thereof as measured from a sample derived from a female subject to be tested is indicative for the risk to suffer from LVH. According to some embodiments increased amounts with respect to the reference amount are indicative for the risk to suffer from LVH.

The amounts for cardiac troponin or a variant thereof, GDF15 or a variant thereof and IGFBP7 or a variant thereof as measured in a control group or a control population are for example used to establish a cut-off amount or a reference range. An amount above such cut-off amount or out-side the reference range and its higher end is considered as elevated.

In a one embodiment a fixed cut-off value is established. Such cut-off value is chosen to match the diagnostic question of interest.

In the context of the aforementioned method, the terms "decreased" and "increased" may refer to amounts that are increased or decreased with respect to the average amount in a population of subjects, in particular the median amount. According to some embodiments, said population is a population of healthy subjects.

According to some embodiments, an amount of a cardiac troponin, such as of troponin T, in a sample of female subject that is at least 30%, or for example, at least 50% larger than the amount of a cardiac troponin, in particular of troponin T, in a sample of a female subject (or group of female subjects) who is (are) not at risk to suffer from LVH indicates that the test female subject is at risk of suffer from LVH. A subject who is not at risk of suffering from LVH may be a subject without functional and structural abnormalities of the heart preceding heart failure and/or preceding left ventricular hypertrophy (for a definition of this term, see elsewhere). Said subject may bear at least one risk factor for heart failure (and, thus may be in stage A as described elsewhere herein). According to some embodiments, however, the subject who is not at risk to suffer from LVH is a healthy subject. Preferably, the sample is serum or plasma sample.

Thus, the reference amount is derived from a healthy female subject (or from a group thereof). According to some embodiments, an increase of a cardiac troponin (in particular of troponin T) of at least 30%, for example, of at least 50% as compared to the amount in a healthy female subject (or to the median amount in group of healthy female subjects) is indicative for a risk of the subject to suffer from left ventricular hypertrophy.

If the amount of troponin T is measured, the reference amount serving as a cut-off may be within a range of 2 to 14 pg/ml. According to some embodiments, the reference amount, serving for troponin T as cut-off is within a range of 3.2 to 4 pg/ml. According to some embodiments reference amounts of troponin T that may serve as cut-off amount include 3.2, 3.4 and 4.2 pg/ml. A exemplary reference amount of troponin I that may serve as cut-off amount is within a range of 0.2 to 9.0 pg/ml. A further exemplary reference amount of troponin I that may serve as cut-off amount is 9.0 pg/ml. An amount of a cardiac troponin in sample, such as a serum or plasma sample, of a female subject larger than the reference amount indicates that the subject is a risk to suffer from LVH. An amount of a cardiac troponin in sample, such as a serum or plasma sample, of a female subject lower than the reference amount indicates that the subject is not a risk to suffer from LVH.

If the amount of IGFBP7 is measured, the reference amount serving as a cut-off may be within a range of 33.3 pg/ml to 46.2 pg/ml. According to some embodiments, the reference amount, serving for IGFBP7 as cut-off is within a range of 42.6 to 46.2 pg/ml. According to some embodiments reference amounts of IGFBP7 that may serve as cut-off amount include 42.6 pg/ml and 46.2 pg/ml.

In an embodiment of the methods and uses of the present disclosure IGFBP7 can also used as single marker instead of the cardiac Troponin (thus, IGFBP7 may replace the cardiac Troponin).

In a further embodiment, the present disclosure provides a method of diagnosing heart failure in a subject, the method comprising the steps of:
a) measuring in a sample obtained from the subject the concentration of at least one cardiac troponin or a variant thereof,
b) optionally measuring in the sample the concentration of one or more other marker(s) of heart failure, and
c) assessing heart failure by comparing the concentration determined in step (a) and optionally the concentration(s) determined in step (b) to reference amounts.

Methods of the present disclosure include in vitro methods. According to some embodiments, the concentrations of at least one marker are determined in a sample obtained from said subject. Moreover, it may comprise steps in addition to those explicitly mentioned above. For example, further steps may relate to sample pre-treatments or evaluation of the results obtained by the method. The method of the present disclosure may be also used for monitoring, confirmation, and subclassification of the subject. The method may be carried out manually or assisted by automation. According to some embodiments, the step of determining the concentration of at least one cardiac troponin in at least one sample of said subject, the step of comparing the thus determined concentration of the said marker(s) as determined in the preceding step to the concentration of this marker established in a control sample, and/or the step of diagnosing/differentiating/predicting may in total or in part be assisted by automation, e.g., by a suitable robotic and sensory equipment.

As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Exemplary confidence intervals are at least 90%, at least 95%, at least 97%, at least 98% or at least 99%. The p-values, according to some embodiments include 0.1, 0.05, 0.01, 0.005, or 0.0001. According to some embodiments, at least 60%, at least 70%, at least 80% or at least 90% of the subjects of a population can be properly identified by the method of the present disclosure.

The terms "individual", "subject" and "patient" may be used interchangeably herein and relate to an animal, for example a mammal such as a human. The subject may be a male or a female subject.

It is envisaged in accordance with the aforementioned method of the present disclosure that the subject shall be a subject belonging to ACC/AHA stage A, and showing one or more of the risk factors for developing HF. Furthermore, the subject may have entered into stage B or may be about to enter into stage B (early stage B) of the ACC/AHA classification. Said subject shall not exhibit symptoms and/or physical signs known to be associated with HF (i.e. the subject is apparently healthy).

The method of the present disclosure makes use of so-called "markers" or "molecular markers". These terms are known to the person skilled in the art and refer to polypeptides or proteins which are expressed in the body of the subject. On the one hand, the expression or elevated expression can be the consequence of a pathophysiological state which has occurred or is occurring in the subject, and an elevated concentration, in respect to "normal" values (which, as the case may be, can be zero) measured in a physiologically healthy subject, is indicative of the pathophysiological state (or the "disease") occurring in the subject. On the other hand, the protein can be expressed in certain concentrations in physiologically healthy subjects, and the expression is raised in consequence of a pathophysiological state which has occurred or is occurring in the subject.

In the context of the present disclosure, the markers which are measured all belong to the first group, i.e. they are expressed or expressed in higher concentrations than normal if the subject suffers from a pathophysiological state or disease. All the marker types and markers employed in the present disclosure are known to the person skilled in the art.

The present disclosure makes use of cardiac troponins and variants thereof. It is known that patients suffering from myocardial infarction MI can be diagnosed using cardiac troponins, for example troponin T or I. Myocardial infarction is regarded as being caused by a necrotic state of the myocard, i.e. cell death. Cardiac troponins are released following cell death and can hence be used for the diagnosis of MI. If the concentration of Troponin T in the blood is elevated, i.e. above 0.1 ng/ml, an acute cardiovascular event is assumed and the patient is treated accordingly. However, it is known that cardiac troponins are also released (in small concentrations) in pathological states preceding cell death, e.g. ischemia.

The term "cardiac Troponin" refers to all Troponin isoforms expressed in cells of the heart and for example the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. According to some embodiments, cardiac Troponin refers to Troponin T and/or Troponin I, and, most preferably, to Troponin T. It is to be understood that isoforms of Troponins may be determined in the method of the present disclosure together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44: 487-493.

The term "cardiac Troponin" encompasses also variants of the aforementioned specific Troponins, such as Troponin I and Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present disclosure shall have an amino acid sequence which differs due to at least one amino acid substitution, deletion and/or addition wherein the amino acid sequence of the variant is still, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. According to some embodiments, the cardiac troponin variants have immunological properties (i.e. epitope composition) comparable to those of human troponin T or troponin I. Thus, the variants shall be recognizable by the aforementioned means or ligands used for determination of the concentration of the cardiac troponins. Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. According to some embodiments the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). According to some embodiments the biological property of troponin T and its variant is the ability to form a complex with troponin C and I, to bind calcium ions or to bind to tropomyosin, if present as a complex of troponin C, I and T or a complex formed by troponin C, troponin I and a variant of troponin T. It is known that low concentrations of circulating cardiac troponin may be detected in subjects at various conditions, but further studies are required to understand their respective role and rate (Masson et al., Curr Heart Fail Rep (2010) 7:15-21).

The term "Growth-Differentiation Factor-15" or "GDF-15" relates to a polypeptide being a member of the transforming growth factor (TGF)-β cytokine superfamily. The terms polypeptide, peptide and protein are used interchangeable throughout this specification. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-β-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the said GDF-15 polypeptides. An exemplary assay is described in the accompanying Examples. Moreover, it is to be understood that a variant as referred to in accordance with the present disclosure shall have an amino acid sequence which differs due to at least one amino acid substitution, deletion and/or addition wherein the amino acid sequence of the variant is still, for example, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific GDF-15 polypeptides, for example with the amino acid sequence of human GDF-15, for example over the entire length of the specific GDF-15, e.g. of human GDF-15. The degree of identity between two amino acid sequences can be determined by algorithms well known in the art. According to some embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT may be employed to determine their optimal alignment and, thus, the degree of identity. According to some embodiments, the default values of 5.00 for gap weight and 0.30 for gap weight length are used. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to posttranslational modifications such as phosphorylation or myristylation.

The Insulin like growth factor binding protein (IGFBP) system plays an important role in cell growth and differentiation. It comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to include the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBP-rPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999) 761-787).

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein I; IGFBP 7; IGFBP 7v; IGFBP rPl; IGFBP7; IGFB-PRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP7 was initially identified as a gene differentially expressed in normal leptomeningeal and mammary epithelial cells, compared with their counterpart tumor cells, and named meningioma-associated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin stimulating factor (Akaogi, K., et al., Proc Natl Acad Sci USA 93 (1996) 8384-8389). It has additionally been reported as T1Al2, a gene down-regulated in breast carcinomas (StCroix, B., et al., Science 289 (2000) 1197-1202).

The biological roles of IGFBP7 have not yet been clearly established. Preliminary experimental data are somewhat controversial and relate to diverse actions for IGFBP7, such as tumor suppression (Sprenger, C. C., et al., Cancer Res 59 (1999) 2370-2375), tumor growth promotion (Lopez-Bermejo, A., et al., J. Clinical Endocrinology and Metabolism 88 (2003) 3401-3408, stimulation of prostacyclin (Akaogi, K., et al., Proc. Natl. Acad. Sci. USA 93 (1996) 8384-8389) and involvement in angiogenesis (Yamauchi, T., et al., Biochem J. 303 (1994) 591-598) and senescence (Lopez-Bermejo, A., et al., Endocrinology 141 (2000) 4072-4080).

Differential expression of IGFBP7 mRNA was measured in patients suffering from various diseases including cardiac disease, kidney disease, inflammatory diseases (U.S. Pat. No. 6,709,855 to Scios Inc.) and vascular graft disease (US 2006/0,003,338).

A number of different assays has been described and used to test for the hormone binding properties of IGFBP7. Low affinity IGF binding was analyzed via competitive affinity cross-linking assays. Recombinant human mac25 protein specifically binds IGF-I and -II (Oh, Y., et al., J. Biol. Chem. 271 (1996) 20322-20325; Kim, H. S., et al., Proc. Natl. Acad. Sci USA 94 (1997) 12981-12986.) IGFBP activity can also be detected by measuring the ability of the protein to bind radiolabeled IGF in Western ligand blotting.

Immunological determination of circulating IGFBP7 was performed recently. Low levels of this analyte were detected in random human sera and increased serum levels have been seen in association with insulin-resistance (Lopez-Bermejo, A., et al., J. Clinical Endocrinology and Metabolism 88 (2003) 3401-3408, Lopez-Bermejo, A., et al., Diabetes 55 (2006) 2333-2339).

The term "reference amounts" or "reference values" as used herein in this embodiment of the disclosure refers to amounts of the polypeptides which allow to diagnose if the respective individual classified in ACC/AHA class A has developed heart disease typically preceding heart failure or is about to develop heart disease typically preceding heart failure.

Therefore, the reference amounts will in general be derived from a subject known to have heart disease typically preceding heart failure and/or being about to develop heart disease typically preceding heart failure. In an embodiment of the present disclosure, subject is classified in ACC/AHA class A.

The expression "comparing the concentration . . . to the concentration as established in a control sample" is merely used to further illustrate what is obvious to the skilled artisan anyway. The control sample may be an internal or an external control sample. In one embodiment an internal control sample is used, i.e. the marker level(s) is(are) assessed in the test sample as well as in one or more other sample(s) taken from the same subject to determine if there are any changes in the level(s) of said marker(s). In another embodiment an external control sample is used. For an external control sample the presence or concentration of a marker in a sample derived from the individual is compared to its presence or concentration in an individual known to suffer from, or known to be at risk of, a given condition; or an individual known to be free of a given condition, i.e., "normal individual". For example, a marker level in a patient sample can be compared to a level known to be associated with a specific course of disease in HF. Usually the sample's marker level is directly or indirectly correlated with a diagnosis and the marker level is e.g. used to determine whether an individual is at risk for HF. Alternatively, the sample's marker level can e.g. be compared to a marker level known to be associated with a response to therapy in patients suffering from structural and/or functional abnormalities of the heart preceding heart failure, the differential diagnosis of risk factors for developing heart failure and structural and/or functional abnormalities of the heart preceding heart failure, the guidance for selecting an appropriate drug to treat structural and/or functional abnormalities of the heart preceding heart failure, in particular early stages, in judging the risk of disease progression, or in the follow-up of patients having structural and/or functional abnormalities of the heart preceding heart failure. Depending on the intended diagnostic use an appropriate control sample is chosen and a control or reference value for the marker established therein. It will be appreciated by the skilled artisan that such control sample in one embodiment is obtained from a reference population that is age-matched and free of confounding diseases. As also clear to the skilled artisan, the absolute marker values established in a control sample will be dependent on the assay used. According to some embodiments samples from 100 well-characterized individuals from the appropriate reference population are used to establish a control (reference) value. Also in some instances the reference population may be chosen to consist of 20, 30, 50, 200, 500 or 1000 individuals. Healthy individuals represent an exemplary reference population for establishing a control value.

An increased value for cardiac troponin or a variant thereof as measured from a sample derived from an individual indicates structural and/or functional abnormalities of the heart preceding heart failure, an increased value of GDF15 or a variant thereof and IGFBP7 or a variant thereof as measured from a sample derived from an individual is indicative for heart failure. The values for cardiac troponin or a variant thereof, GDF15 or a variant thereof and IGFBP7 or a variant thereof as measured in a control group or a control population are for example used to establish a cut-off value or a reference range. A value above such cut-off value or out-side the reference range and its higher end is considered as elevated. In a one embodiment a fixed cut-off value is established. Such cut-off value is chosen to match the diagnostic question of interest.

In one embodiment values for cardiac troponin or a variant thereof, GDF15 or a variant thereof and IGFBP7 or a variant thereof as measured in a control group or a control population are used to establish a reference range. In another embodiment an cardiac troponin or a variant thereof, GDF15 or a variant thereof and IGFBP7 or a variant thereof concentration is considered as elevated if the value measured is above the 90%-percentile of the reference range. In further embodiments an cardiac troponin or a variant thereof, GDF15 or a variant thereof and IGFBP7 or a variant thereof concentration is considered as elevated if the value measured is above the 95%-percentile, the 96%-percentile, the 97%-percentile or the 99%-percentile of the reference range.

In one embodiment the control sample will be an internal control sample. In this embodiment serial samples are obtained from the individual under investigation and the marker levels are compared. This may for example be useful in assessing the efficacy of therapy.

The sensitivity and specificity of a diagnostic and/or prognostic test depends on more than just the analytical "quality" of the test-they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker of the disclosure, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al, Radiology 143: 29-36 (1982).

In certain embodiments, markers and/or marker panels are selected to exhibit at least about 70% sensitivity, at least about 80% sensitivity, at least about 85% sensitivity, at least about 90% sensitivity, and even at least about 95% sensitivity, combined with at least about 70% specificity, at least about 80% specificity, at least about 85% specificity, at least about 90% specificity, and even at least about 95% specificity. In some embodiments, both the sensitivity and specificity are at least about 75%, at least about 80%, at least about 85%, at least about 90%, and even at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain embodiments, markers and/or marker panels are preferably selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, and even at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain embodiments, markers and/or marker panels are selected to exhibit an odds ratio of at least about 2 or more or about 0.5 or less, at least about 3 or more or about 0.33 or less, at least about 4 or more or about 0.25 or less, at least about 5 or more or about 0.2 or less, and even at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain embodiments, markers and/or marker panels are selected to exhibit a hazard ratio of at least about 1.1 or more or about 0.91 or less, at least about 1.25 or more or about 0.8 or less, at least about 1.5 or more or about 0.67 or less, at least about 2 or more or about 0.5 or less, and even at least about 2.5 or more or about 0.4 or less. The term "about" in this context refers to +/−5% of a given measurement.

While exemplary panels are described herein, one or more markers may be replaced, added, or subtracted from these exemplary panels while still providing clinically useful results. Panels may comprise both specific markers of a disease (e.g., markers that are increased or decreased in bacterial infection, but not in other disease states) and/or non-specific markers (e.g., markers that are increased or decreased due to inflammation, regardless of the cause; markers that are increased or decreased due to changes in hemostasis, regardless of the cause, etc.). While certain markers may not individually be definitive in the methods described herein, a particular "fingerprint" pattern of changes may, in effect, act as a specific indicator of disease state. As discussed above, that pattern of changes may be obtained from a single sample, or may optionally consider temporal changes in one or more members of the panel (or temporal changes in a panel response value).

The diagnosis if individuals are healthy or suffer from a certain pathophysiological state is made by established methods known to the person skilled in the art. The methods differ in respect to the individual pathophysiological state.

The algorithms to establish the desired diagnosis are laid out in the present application, in the passages referring to the respective embodiment, to which reference is made.

Accordingly, the present disclosure also comprises a method of determining the threshold level indicative for a physiological and/or a pathological state and/or a certain pathological state, comprising the steps of determining in appropriate patient groups the levels of the appropriate marker(s), collecting the data and analyzing the data by statistical methods and establishing the threshold values.

In the present disclosure, the appropriate markers are cardiac troponins and variants thereof, including troponin T or a variant thereof or troponin I or a variant thereof, and optionally at least one further marker selected from GDF-15 or a variant thereof and IGFBP7 or a variant thereof.

The present disclosure also relates to a method of deciding on the therapy of a subject as referred to above based on the aforementioned steps. Therefore, the method of the present disclosure allows to decide which kind of intervention or which pharmaceutical or pharmaceuticals should be taken by a subject suffering from functional and/or structural abnormalities of the heart preceding heart failure or being about to develop functional and/or structural abnormalities of the heart preceding heart failure, where the subject is classified into ACC/AHA stage A. Treatment can aim at treating the functional and/or structural abnormalities of the heart preceding heart failure as such, or to preventing further deterioration of the functional and/or structural abnormalities of the heart preceding heart failure.

Treatment Decision.

Accordingly, the present disclosure relates to a method of deciding on the treatment of functional and/or structural abnormalities of the heart preceding heart failure in a subject, based on the comparison of the concentrations of at least on cardiac troponin or a variant thereof, and optionally of one or more other markers of heart failure, to the concentration of this or these marker(s) in a control sample.

The method of the disclosure may comprise the following steps: a) measuring in a sample obtained from the subject the concentration of at least one cardiac troponin or a variant thereof; b) optionally measuring in the sample the concentration of one or more other marker(s) of heart failure; c) comparing the thus determined concentration to reference amounts, e.g. to the concentration of this marker or these markers as established in a control sample.

According to some embodiments, the therapy decision is taken by comparing the determined concentrations with a reference amount.

The present disclosure therefore provides a method of deciding on the treatment of functional and/or structural abnormalities of the heart preceding heart failure in a subject, the method comprising the steps of
a) measuring in a sample obtained from the subject the concentration of at least one cardiac troponin or a variant thereof,
b) optionally measuring in the sample the concentration of one or more other marker(s) of heart failure, and
c) deciding on treatment of the subject by comparing the thus determined concentration with a reference amount.

According to some embodiments, before deciding on the treatment, it is diagnosed if the subject suffers from functional and/or structural abnormalities of the heart preceding heart failure and/or preceding left ventricular hypertrophy.

In general, the subject does not suffer from heart failure, i.e. the patient has not experienced permanent structural or functional damages to his myocardium. According to some embodiments the subject has a left ventricular mass index below the criteria used to define left ventricular hypertrophy. According to some embodiments, the subject bears risk factors for heart failure. These are known to the person skilled in the art and include e.g. hypertension and diabetes. Also in some embodiments, the subject does not show overt signs and/or symptoms of heart failure. The subject may be classified into ACC/AHA stage A, prior to carrying out the method of the present disclosure.

The person skilled in the art is aware of methods to diagnose if a subject suffers from functional and/or structural abnormalities of the heart preceding heart failure or is about to develop functional and/or structural abnormalities of the heart preceding heart failure, where the subject is classified into ACC/AHA stage A. This diagnosis is in general costly, time-consuming and requires medical skill and experience. Thus early functional and/or structural abnormalities often remain underdiagnosed. Methods of evaluation are known to the person skilled in the art and are typically based on medical history, further evaluation includes examination using diagnostic apparatuses/devices (cardiac auscultation, ECG, echocardiography, chest x-ray, radionuclide imaging, ventriculography, CT scan, MRI and/or stress testing, coronary angiography, ultrasonography, coronary catheterization. Other tests may be done as needed to determine the cause. Methods described above are applied reluctant, because of limited sensitivity to detect structural and/or functional abnormalities of the heart preceding LVH and/or heart failure. Treatment depends on the specific type and severity of the functional and/or structural abnormalities of the heart preceding heart failure. Preventive treatment may be initiated before progression to LVH and/or to HF or other major complications. As a consequence of diagnosing first structural abnormalities in subjects with arterial hypertension or diabetes, these patients, that may rapidly progress to LVH need more intensive medication or adaption of medication and more intensive monitoring.

In an exemplary embodiment, the present disclosure provides a method of therapy adaption a consequence of diagnosis of early functional and/or structural abnormalities of the heart preceding heart failure, in particular preceding LVH. The therapeutic consequence is a change of antihypertensive medication, for example angiotensin-converting enzyme (ACE) inhibitors, Angiotensin-II-receptor blocker (ARB), aldosteron antagonists, beta blockers versus diuretics and Calcium antagonists. Accordingly, the administration of angiotensin-converting enzyme (ACE) inhibitors, Angiotensin-II-receptor blocker (ARB), and/or aldosteron antagonists are, in some instances, recommended, if early functional and/or structural abnormalities of the heart preceding heart failure are diagnosed.

In a further embodiment of the present disclosure, the supplementary/complementary methods as laid out beforehand can be used for the methods of deciding on the treatment of a subject as referred to above, based on the aforementioned steps. These methods are laid out further below in the present application and allow to decide which pharmaceutical or pharmaceuticals should be taken by said subject or which other therapy the subject should undergo.

The disclosure also encompasses the use of at least one marker selected from cardiac troponins and variants thereof, and, optionally, at least one marker selected from: GDF-15 or a variant thereof and IGFBP7 or a variant thereof, for deciding on the treatment of functional and/or structural abnormalities of the heart preceding heart failure in a subject bearing risk factors of developing heart failure but not showing overt signs of heart failure.

In an embodiment of the present disclosure, the cardiac troponin is selected from troponin T or a variant thereof and troponin I or a variant thereof, in particular the cardiac troponin is troponin T or a variant thereof. In one embodiment of the present disclosure, the following markers are determined in combination: the cardiac troponin is selected from troponin T or a variant thereof and troponin I or a variant thereof, in particular the cardiac troponin is troponin T or a variant thereof; GDF-15 or a variant thereof; and IGFBP7 or a variant thereof.

The term "deciding" as used herein means assessing as to whether a certain medication or treatment should be administered to a subject having undergone the test according to the present disclosure.

Therapy, Treatment.

The term "therapy" as used in the context of the present disclosure encompasses life style changes, diet regimen, interventions on the body as well as administration of appropriate drugs for the treatment of a subject according to the present disclosure. The subject suffers from functional and/or structural abnormalities of the heart preceding left ventricular hypertrophy and/or heart failure or is about to develop functional and/or structural abnormalities of the heart preceding heart failure, and the subject may be classified into ACC/AHA stage A. According to some embodiments, the subject has arterial hypertension, systolic and/and or diastolic hypertension, obesity, metabolic syndrome, and/or diabetes mellitus (e.g., type 2 diabetes mellitus). In yet another embodiment the individual suffers from low, moderate, high or very high risk according to the risk chart of the European Society of Hypertension.

Pharmaceuticals suitable for the treatment of functional and/or structural abnormalities of the heart preceding heart failure are well known in the art, see e.g. Heart Disease, 2008, 8$^{th}$ Edition, Eds. Braunwald, Elsevier Sounders, chapter 24 (in respect to heart failure) and chapter 41 (in respect to hypertension). These treatments are a part of the present disclosure. According to some embodiments, the administration of such pharmaceuticals aims to treat the symptoms and signs of functional and/or structural abnormalities of the heart preceding heart failure caused and which aim to prevent a further progression of functional and/or structural abnormalities of the heart preceding heart failure and/or development of heart failure. Accordingly, also contemplated are pharmaceuticals that aim to treat functional and/or structural abnormalities of the heart preceding left ventricular hypertrophy and/or heart failure and/or left ventricular dysfunction and/or heart failure.

Life style changes include smoking cessation, moderation of alcohol consumption, increased physical activity, weight loss, sodium (salt) restriction, weight management and healthy eating, daily fish oil, salt restriction.

The therapy may also include interventions. One exemplary intervention in the context of the present disclosure is administration of antihypertensive medication with such as angiotensin-converting enzyme (ACE) inhibitors, Angiotensin-II-receptor blocker (ARB), aldosteron antagonists, beta blockers versus diuretics and Calcium antagonists. In an exemplary embodiment, the present disclosure provides a method of therapy adaption a consequence of diagnosis of early functional and/or structural abnormalities of the heart preceding heart failure and/or in particular even preceding LVH. The therapeutic consequence is a change of antihypertensive medication for example with angiotensin-converting enzyme (ACE) inhibitors, Angiotensin-II-receptor blocker (ARB), aldosteron antagonists, beta blockers versus diuretics and Calcium antagonists.

When a level of a cardiac troponin or variants thereof, in particular Troponin T or a variant thereof, indicates that the subject has functional and/or structural abnormalities of the heart preceding left ventricular hypertrophy and/or preceding heart failure, one or more of the following drugs should be administered:

diuretics like loop diuretics, thiazide and thiazide-like diuretics, K-sparing diuretics, type I mineralocorticoid receptor antagonists, antialdosterone, carbonic anhydrase inhibitors, vasopressure antagonists;

Beta blockers like proprenolol, metoprolol, bisoprolol, carvedilol, bucindolol, nebivolol;

calcium antagonists like dihydropyridines, verapamil, diltiazem;

adrenergic agonists, like dobutamine, dopamine, epinephrine, isoprotenerol, norepinephrine, phenylephrine;

positive inotropic agents, like digoxin, digitoxin;

ACE inhibitors like Enalapril, Captopril, Ramipril, Trandolapril;

angiotensin receptor antagonists like Losartan, Valsartan, Irbesartan, Candesartan, Telmisartan, Eprosartan;

aldosterone antagonists like Eplerone, Spironolactone, Canrenone, Mexrenone, Prorenone;

statines, in particular Atorvastatin, Fluvastatin, Lovastatin, Pravastatin, Rosuvastatin, Simvastatin;

hydazaline and isosorbide dinitrate.

When a level of a cardiac troponin or a variant thereof, for example troponin T or a variant thereof, indicates that the subject suffers from early stage functional and/or structural abnormalities of the heart preceding heart failure (e.g., early stage B) and/or does not show LVH and/or diastolic dysfunction without LVH, one or more of the following drugs should be administered:

Beta blockers like proprenolol, metoprolol, bisoprolol, carvedilol, bucindolol, nebivolol;

adrenergic agonists, like dobutamine, dopamine, epinephrine, isoprotenerol, norepinephrine, phenylephrine;

aldosterone antagonists like Eplerone, Spironolactone, Canrenone, Mexrenone, Prorenone.

Exemplary therapeutics according to some embodiments include:
- ACE inhibitors like Enalapril, Captopril, Ramipril, Trandolapril; and
- angiotensin receptor antagonists like Losartan, Valsartan, Irbesartan, Candesartan, Telmisartan, Eprosartan.

Treatment Monitoring.

Furthermore, the present disclosure provides a method of monitoring treatment of functional and/or structural abnormalities of the heart preceding heart failure in a subject, based on the comparison of the concentrations of at least one cardiac troponin or a variant thereof and repeatedly determined, and optionally of one or more other markers of heart failure and repeatedly determined, to the concentration of this or these marker(s) in a control sample.

The method of the disclosure may comprise the following steps:
a) repeatedly determining, within given time intervals, the concentration of at least one cardiac troponin or a variant thereof,
b) optionally repeatedly measuring in the sample the concentration of one or more other marker(s) of heart failure, and
c) comparing the thus determined concentration of the said markers as determined in step a) to its concentration in a control sample, and
d) assessing, based on the differences in the determined concentrations in one or more of the above-cited markers, whether the subject has undergone a change in its pathophysiological state.

According to some embodiments, the assessment is carried out by comparing the thus determined concentration of the said markers as determined in step a) and optionally step b) to its concentration in a control sample The present disclosure therefore provides a method of monitoring treatment of functional and/or structural abnormalities of the heart preceding heart failure in a subject, the method comprising the steps of:
a) determining the concentration of at least one cardiac troponin or a variant thereof,
b) optionally measuring in the sample the concentration of one or more other marker(s) of heart failure, and
c) assessing whether the subject has undergone a change in its pathophysiological state by comparing the thus determined concentration of the said markers as determined in step a) to its concentration in a control sample.

According to some embodiments of the present disclosure, the determination of the cardiac troponin and, optionally, the one or more other markers of heart failure is carried out repeatedly, i.e. at least 2 times, and, in some cases, within a given time interval or time intervals.

In general, the subject does not suffer from heart failure, i.e. the patient has not experienced permanent structural or functional damages to his myocardium. Preferably, the subject bears risk factors for heart failure. These are known to the person skilled in the art and include e.g. hypertension and diabetes. Also in some cases, the subject does not show overt signs and/or symptoms of heart failure.

The concentration cited in step b) may be the concentration cited in the present application in respect to the therapy decision beforehand, or may be the concentrations determined before the therapy was initiated, or both.

In general, prior to carrying out the monitoring method of some embodiments of the present disclosure, the method of deciding on the therapy of treating left ventricular hypertrophy is carried out.

Therapy Adaptation.

In a further embodiment of the present disclosure provides a method of therapy adaption a consequence of predicting the risk of heart failure in a subject with diagnosed functional and/or structural abnormalities of the heart preceding heart failure, in particular when LVH is not apparent. In case of risk of heart failure, the therapeutic consequence is a change of antihypertensive medication to, for example, angiotensin-converting enzyme (ACE) inhibitors, Angiotensin-II-receptor blocker (ARB), aldosteron antagonists, beta blockers versus diuretics and Calcium antagonists. The methods of the present disclosure provide antihypertensive therapy adaption of subjects with stage A and/or early stage B HF as a consequence of diagnosis of structural changes preceding left ventricular hypertrophy and/or heart failure to, for example, angiotensin-converting enzyme (ACE) inhibitors, Angiotensin-II-receptor blocker (ARB), aldosteron antagonists, beta blockers versus diuretics and Calcium antagonists. Advantageously further progression to left ventricular hypertrophy and/or heart failure may be prevented.

Determining the concentration of a cardiac troponin or a variant thereof and, as the case may be, GDF-15 or a variant thereof, or IGFBP7 or a variant thereof, or any other peptide or polypeptide referred to in this specification relates to measuring the concentration or concentration, either semi-quantitatively or quantitatively. Measuring can be done directly or indirectly. Direct measuring relates to measuring the concentration or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In a further embodiment of the present disclosure, there are provided methods of therapy monitoring and therapy adaptation in a subject receiving administration of a medicament selected from ACE inhibitors, angiotensin receptor blockers and aldosterone antagonists, or any combination of the aforecited documents and, as the case may be, in addition to any further medicament or combination of medicaments known for the treatment of the hereinafter cited diseases. The method according to this embodiment of the present disclosure, in particular, permits to decide on the administration of aldosterone antagonists, optionally in addition to ACE inhibitors and angiotensin receptor blockers and, as the case may be, in addition to any further medicament known for the treatment of heart failure and/or structural and/or functional abnormalities of the heart preceding heart failure.

In one embodiment, the subject has heart failure, in particular the subject is classified into stage C of the ACC/AHA system. In a further embodiment, the individual suffers from structural and/or functional abnormalities of the heart preceding heart failure.

Currently, it is recommended to treat patients at risk of heart failure with ACE inhibitors and/or angiotensin receptor blockers. This includes patients classified into stages A and B according to the ACC/AHA guidelines.

Starting from stage C (which includes patients with structural heart disease having prior or current symptoms of heart disease) diuretics are recommended which include aldosterone antagonists in selected patients according to the ACC/AHA guidelines. Selected patients include those with moderate to severe heart failure and evidence of recent decompensation (see ACC/AHA guidelines).

It is appreciated that the effect of ACE inhibitors as well as of angiotensin receptor blockers is affected by functional polymorphisms (see McNamara, Heart Failure Clin 6 (2010), p 35-43, in particular Table 1). It has been shown that the prevalence of aldosterone escape on ACE inhibitors is greatest in the ACE DD genotype (Mc Namara et al, p. 39), supporting the rationale for the use of aldosterone antagonists.

Figure 2:
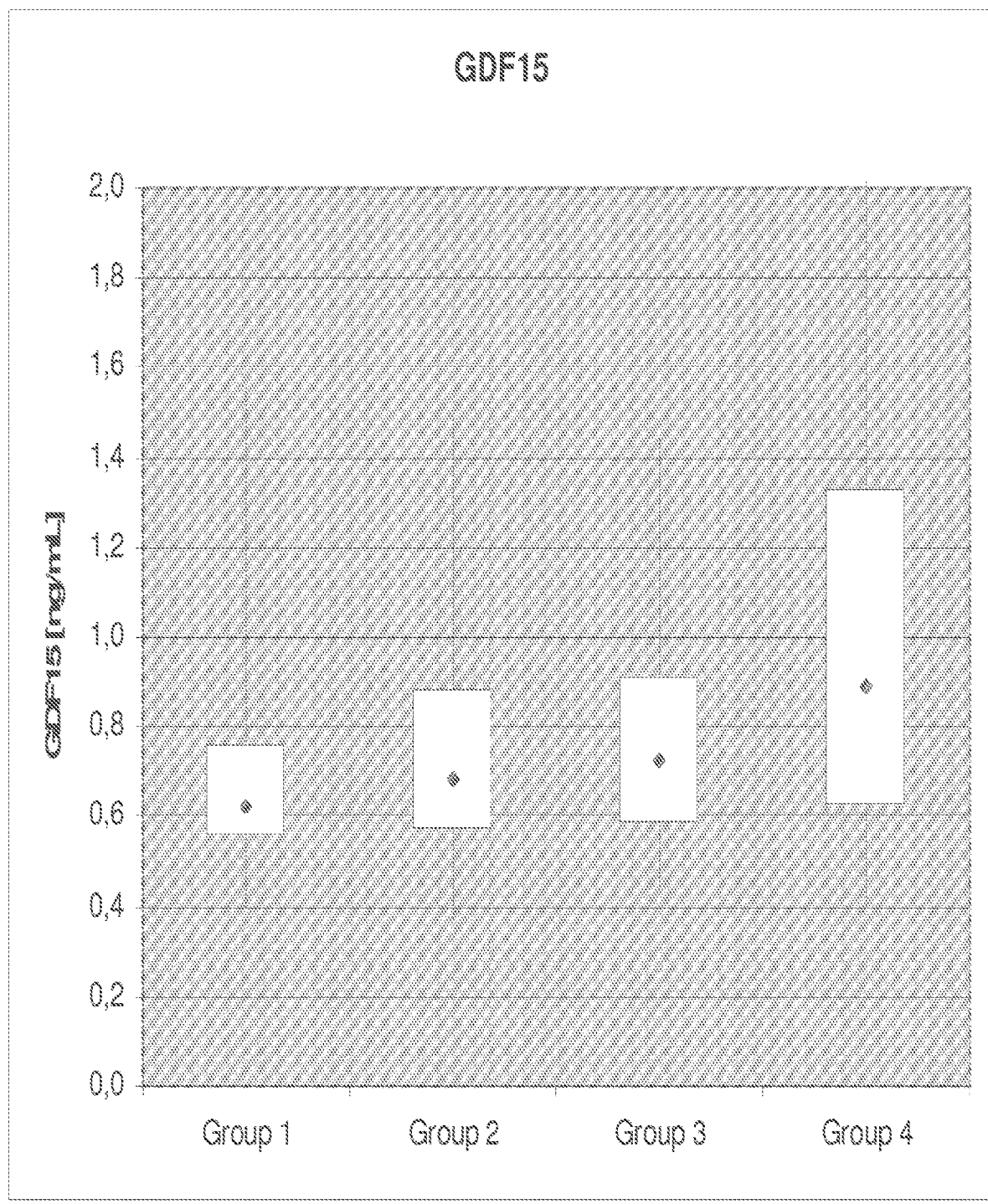
FIG. 2 is a bar graph presenting the values of GDF-15 in patients belonging to group 1, 2, 3 or 4 as described in the Examples.
Figure 3:
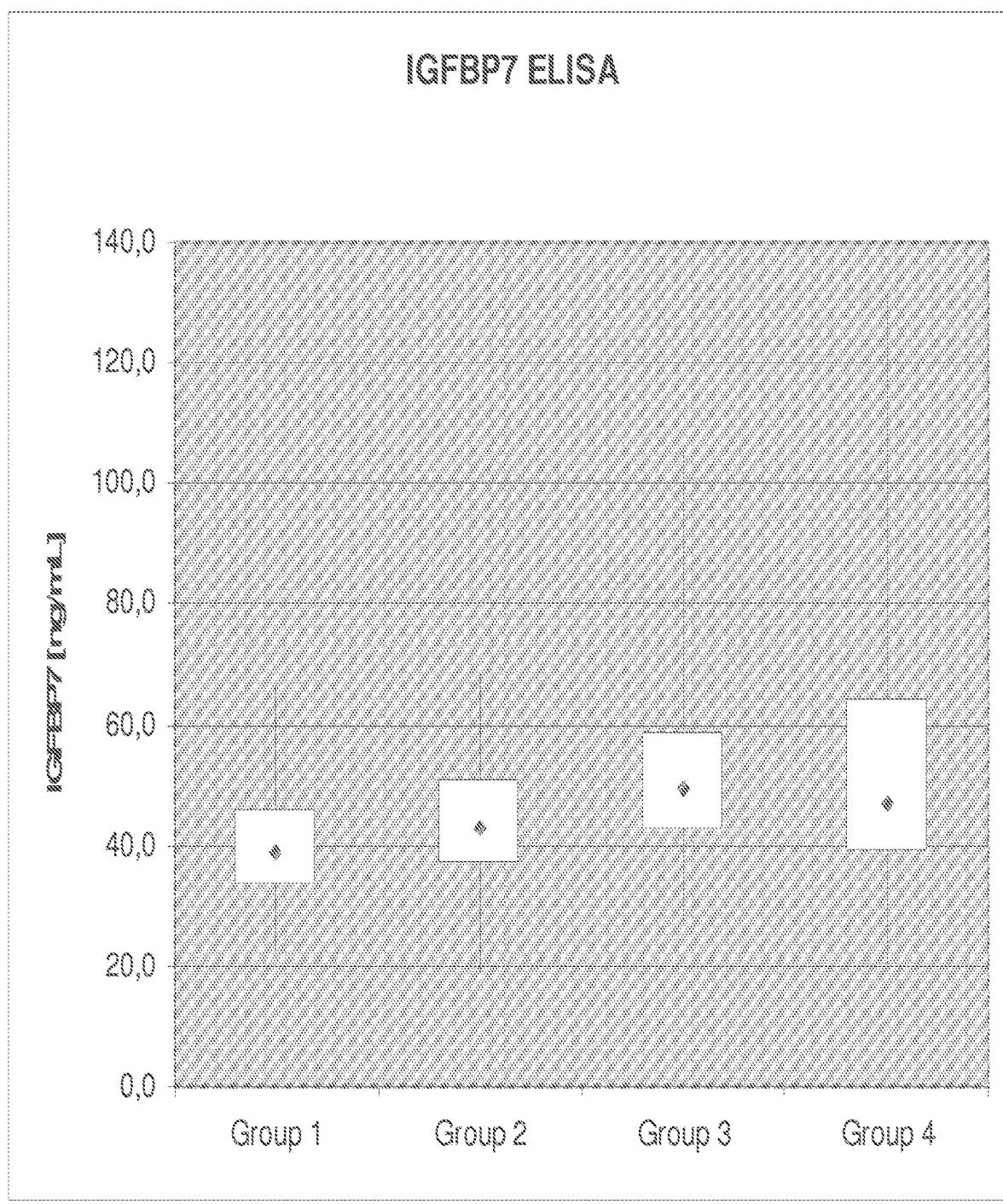
FIG. 3 is a bar graph presenting the values of IFGBP7 in patients belonging to group 1, 2, 3 or 4 as described in the Examples.
Figure 4:
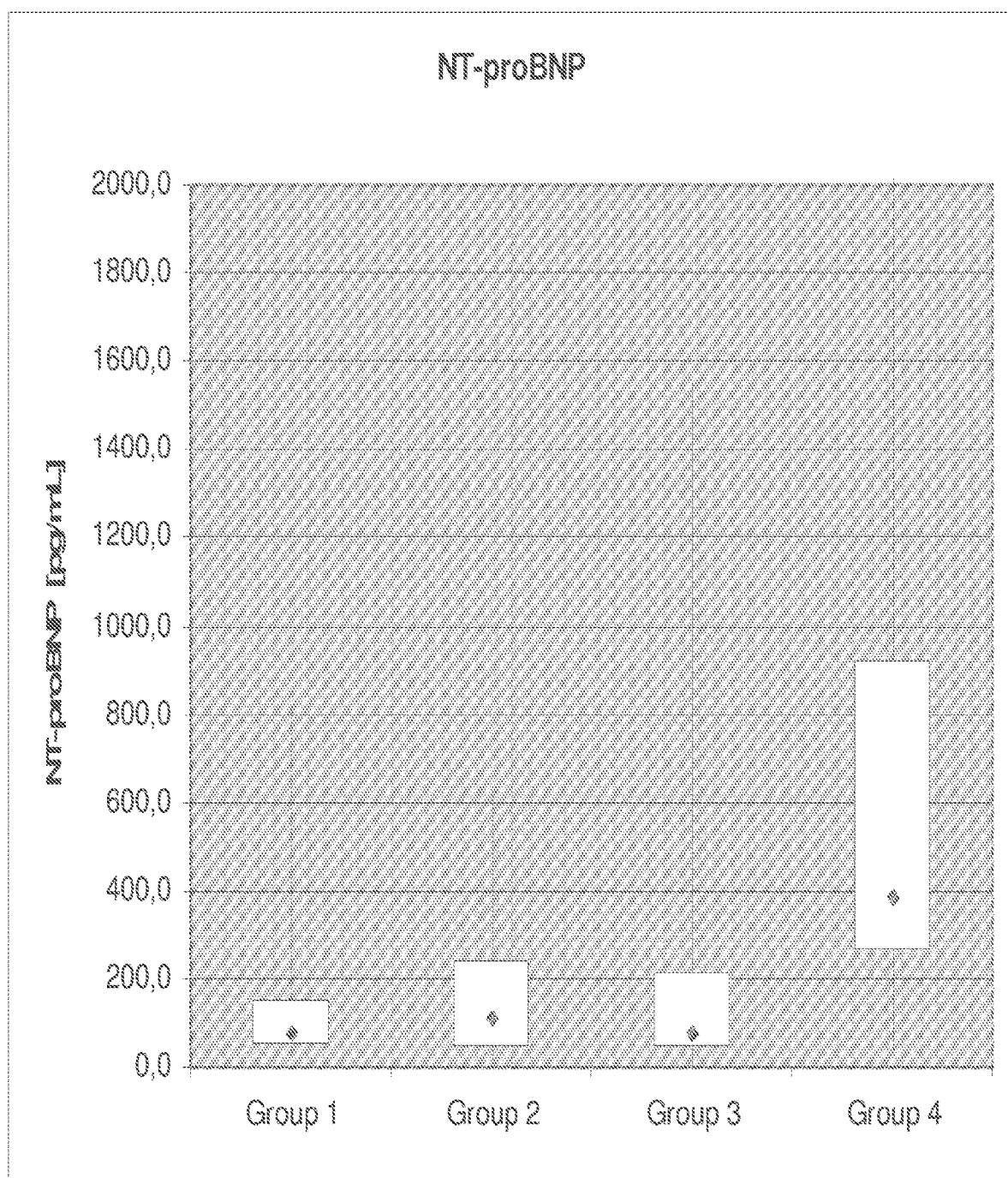
FIG. 4 is a bar graph presenting the values of NT-proBNP in patients belonging to group 1, 2, 3 or 4 as described in the Examples.

Collagen formation in heart tissue is preceded by inflammation. It is known that inflammation is present in heart failure patients through activation of the renin-angiotensin-aldosterone (RAAS) system, supporting the use of aldosterone antagonists in heart failure. Previously it has been shown that the aldosterone antagonist eplerone reduces collagen formation in heart failure patients as indicated by PIIINP levels (see G. Mak et al, JACC vol 54, no 18, 2009, p 1674-1682, in particular FIG. 2). This is further supported by ongoing studies to test the use of aldosterone antagonists in NYHA class II patients (Mc Murray NEJM 362, 228-238, 2010, in particular p 236, "Areas of uncertainty"). This is however consistent with a recent review indicating that aldosterone promotes collagen synthesis in the heart and promotes maladaptive cardiac remodelling (KIM Y. S., Current Treatment Options in Cardiovascular Medicine 11, 455-466, 2009, in particular p. 462, "ARAB").

It was found by the present inventors that cardiac troponins and variants thereof, including troponin T or a variant thereof or troponin I or a variant thereof, in particular troponin T or a variant thereof, and GDF-15 or a variant thereof and, optionally, a natriuretic peptide selected from ANP type and BNP type natriuretic peptides and variants thereof, including BNP or a variant thereof or NT-proBNP or a variant thereof, in particular NT-proBNP or a variant thereof, give relevant information on the efficacy of treatment of the aforementioned subjects. On the one hand, these subjects are those having heart failure, in particular being classified into stage C of the ACC/AHA system. On the other hand, the subjects may have risk factors of suffering from heart failure and may be classified into stage A of the ACC/AHA classification, or suffer from structural and/or functional abnormalities of the heart preceding heart failure and may be classified into stage B of the ACC/AHA classification.

In particular, the amounts of GDF-15, NT-proBNP and Troponin T were determined in 97 patients with overt heart failure. All patients were on beta blocker as well as on ACE inhibitor therapy, 59 patients were on aldosterone antagonists, 38 did not receive aldosterone antagonists After the determination of the amounts of the aforementioned markers, the ratio of NT-pro BNP and GDF 15 and the ratio of Troponin T and GDF-15 was formed. Interestingly, it was found that the ratios in the group of aldosterone antagonist group were higher than in the group of patients not treated with aldosterone antagonists. Therefore, the determination of the GDF-15 in combination with a natriuretic peptide or a cardiac Troponin shall allow for making decisions on the therapy adaption in patients treated with an ACE inhibitor, an angiotensin receptor antagonist, or aldosterone antagonists (or combinations thereof). In particular, said determination shall allow for making decisions on the therapy adaption in patients treated with an ACE inhibitor. The aformentioned medicaments, in particular ACE inhibitors, sometimes become less effective resulting in an increased level of inflammation. In this case, a therapy adaptation with aldosterone antagonists as described herein below would be useful since aldosterone antagonists allow for reducing the level of inflammation. The methods described herein below allow for identifying subjects which may benefit from a therapy adaptation.

While ACE inhibitors and angiotension receptor blockers (ARBs) have been shown to be effective in large randomized trials there is currently no method available to diagnose the effectiveness of these drugs in the individual patient. This is in contrast to the application of these drugs in patients with kidney disease where the decrease of urinary albumin can be used to verify treatment success. Thus the method described offers for the first time a method for the diagnosis of treatment failure and provides guidance for improved treatment using aldosterone inhibitors or in the future drugs that inhibit synthesis of aldosterone.

In one embodiment of the disclosure, a medication which has been initiated in a subject according to the disclosure is monitored (i.e. it is assessed whether the medication is effective). In a further embodiment of the disclosure, a decision on the adaptation of the medication is made, for example, in accordance with the results of the monitoring of the medication. In an exemplary embodiment, it is decided if administration of an aldosterone antagonists is appropriate. It may also be conceived to administrate one or more aldosterone synthetase inhibitors, see Roumen L. et al J Medical Chemistry 2010, 53 1712-25.

The present disclosure therefore furthermore provides a method of monitoring a medication which has been initiated in a subject suffering from heart failure or stages preceding left ventricular hypertrophy and/or preceding heart failure including risk factors for heart failure, based on the comparison of the concentrations of at least on cardiac troponin or a variant thereof, and optionally of one or more other markers of heart failure, to the concentration of this or these marker(s) in a control sample.

The method of the disclosure may comprise the following steps: a) measuring in a sample obtained from the subject the concentration of at least one cardiac troponin or a variant thereof; b) measuring in a sample the concentration of GDF-15 or a variant thereof, c) monitoring the medication by comparing the thus determined concentrations with a reference amount, e.g. in a control sample. According to some embodiments, monitoring is carried out by comparing the determined concentrations with a reference amount.

Accordingly, the present disclosure provides a method of monitoring a medication to which a subject suffering from heart failure or stages preceding left ventricular hypertrophy and/or heart failure including risk factors for heart failure is subjected, the method comprising the steps of:
  a) measuring in a sample obtained from the subject the concentration of at least one cardiac troponin or a variant thereof and/or a natriuretic peptide or a variant thereof,
  b) measuring in a sample the concentration of GDF-15 or a variant thereof,
  c) monitoring the medication by comparing the thus determined concentrations with a reference amount.

The present disclosure furthermore provides a method of decision on the adaptation of a medication which has been initiated in a subject suffering from heart failure or stages preceding heart failure including risk factors for heart failure, based on the comparison of the concentrations of at least on cardiac troponin or a variant thereof, and optionally of one or more other markers of heart failure, to the concentration of this or these marker(s) in a control sample.

The method of the disclosure may comprise the following steps: a) repeatedly measuring in a sample obtained from the subject the concentrations of at least one cardiac troponin or a variant thereof; b) repeatedly measuring in a sample the concentration of GDF-15 or a variant thereof, c) deciding on the adaptation of the medication by comparing the thus determined concentrations with a reference amount. According to some embodiments, the decision on adaptation is carried out by comparing the determined concentrations with a reference amount.

The present disclosure therefore also provides a method of deciding on the adaptation of a medication in a subject subjected to said medication and suffering from heart failure or stages preceding heart failure including risk factors for heart failure, the method comprising the steps of:
 a) measuring in a sample obtained from the subject the concentrations of at least one cardiac troponin or a variant thereof and/or a natriuretic peptide or a variant thereof,
 b) measuring in a sample the concentration of GDF-15 or a variant thereof, and
 c) deciding on the adaptation of the medication by comparing the thus determined concentrations with a reference amount.

According to some embodiments of the present disclosure, the determination of the cardiac troponin and, optionally, the one or more other markers of heart failure is carried out repeatedly, i.e. at least 2 times, and in some cases within a given time interval or time intervals.

A definition of the term "subject" has been given elsewhere herein. The definition applies accordingly. According to some embodiments, the subject in the context of the method of deciding on the adaptation of a medication and the subject in the context of the method of monitoring a medication (both methods based on the determination of the amount of GDF-15 in combination with a natriuretic peptide and a cardiac Troponin), according to some embodiments may not have exhibited and acute coronary syndrome within at least 2 weeks, or, even within at least 4 week before the sample for carrying out the method has been obtained. Also in some embodiments, the subject does not suffer from acute inflammation, in particular from the systemic inflammatory response syndrome (SIRS), at the time at which the sample for carrying out the method has been obtained.

According to some embodiments, the medication is selected from ACE inhibitors, angiotension receptor blockers and aldosterone antagonists. In particular, the medication is an ACE inhibitor.

Examples for these classes of drugs are the following:
 ACE inhibitors: Enalapril, Captopril, Ramipril, Trandolapril; Enalapril
 angiotensin receptor blockers: Losartan, Valsartan, Irbesartan, Candesartan, Telmisartan, Eprosartan; Losartan
 aldosterone antagonists: Eplerenone, Spironolactone, Canrenone, Mexrenone, Prorenone, Spironolactone, Eplerenone.

As described above the recommendation of ACE inhibitors in stages A and B suggests the need for antiinflammatory treatment, however because of polymorphisms this appears not to be effective in all cases. Aldosterone antagonists are considered to be useful also in patients belonging to stages A and B of the ACC/AHA classification, for example in cases where ACE inhibitors and angiotensin receptor blockers are not effective.

Lack of effectiveness of ACE inhibitors and angiotensin receptor blockers can be identified by the present method of the disclosure. This applies, on the one hand, for subjects not suffering from heart failure, but having risk factors of developing heart failure, subjects classified in stage A; on the other hand, the method applies to subjects suffering from functional and/or structural abnormalities of the heart preceding heart failure, subjects classified in stage B. The method of the present disclosure also lends itself for subjects having non reversible structural damage of the heart (i.e. heart failure), subjects classified in stage C.

In the context of the present disclosure, effectiveness of treatment with a medicament from the group ACE inhibitors, angiotensin receptor blockers and aldosterone antagonists is assessed by the concentrations of a cardiac troponin and variants thereof, including troponin T or a variant thereof or troponin I or a variant thereof, in connection with the concentrations of GDF-15 or a variant thereof. In a further embodiment, effectiveness of treatment is assessed by the concentrations of a natriuretic peptide, including BNP or NT-proBNP, in connection with the concentrations of GDF-15.

As clear from the foregoing, increased concentrations of a cardiac troponin in a subject indicate that the subject either suffers from functional and/or structural abnormalities of the heart preceding heart failure, or is already suffering from heart failure. Increased concentrations of a cardiac troponin may also indicate that the subject suffers from coronary artery disease; as known to the person skilled in the art, here the concentrations of a cardiac troponin may be increased in respect to healthy individuals.

Increased concentrations of a natriuretic peptide in a subject indicate that the subject either suffers from functional and/or structural abnormalities of the heart preceding heart failure, or is already suffering from heart failure. Increased concentrations of a natriuretic peptide may also indicate that the subject suffers from coronary artery disease; as known to the person skilled in the art, here the concentrations of a natriuretic peptide may be increased in respect to healthy individuals.

It is also clear from the foregoing that an increased concentration of GDF-15 in a subject is not only indicative of heart failure, but also indicates inflammatory processes occurring in the myocardium of the individual. Accordingly, if the concentration of GDF-15 is not increased or only slightly increased in respect to healthy individuals, this is indicative for no or a low number of inflammatory processes occurring in the myocardium. On the contrary, increased or highly increased concentrations of GDF-15 or a variant thereof in a subject show the occurrence of inflammatory processes in the individual's myocardium.

The person skilled in the art is able to conclude the information necessary for the therapy monitoring and/or therapy adaptation from the respective values of the cardiac troponin or a variant thereof and concentrations of GDF-15 and variants thereof. For example, a only slightly increased concentration (in respect to healthy individuals) of a cardiac troponin or a variant thereof, for example troponin I or a variant thereof or troponin I or a variant thereof, in connection with an increased or even highly increased concentration of GDF-15 or a variant thereof indicates that the subject does not suffer from heart failure, but that a considerable number of inflammatory processes are ongoing in his myocardium, pointing to the danger of development of heart failure and that medication is not effective, with an adaptation being recommended (for an explanation of the therapy adaptation, please see elsewhere herein). Accordingly, an increased level (or highly increased level) of GDF-15 in combination with a slightly increased level of a cardiac troponin indicates that the therapy, in particular the therapy with an ACE inhibitor, shall be adapted.

On the other hand, a highly increased concentration (in espect to healthy individuals) of a cardiac troponin, for example troponin I or troponin I, or a variant thereof respectively, in connection with an only slightly increased concentration of GDF-15 or a variant thereof indicates that the subject suffers from heart failure, but that inflammatory processes are moderate and that medication is effective and an adaptation is not necessary. Accordingly, a highly increased level of a cardiac Troponin in combination with a slightly increased level of GDF-15 indicates that the therapy, in particular the therapy with an ACE inhibitor, that an adaption of the therapy is not necessary, and, thus, that the therapy can be continued.

The person skilled in the art is aware that various intermediate constellations of the concentrations of the above-cited markers exist, indicating various degrees of efficacy of medicament administration.

In an exemplary embodiment of the instant embodiment of the present disclosure, the ratio cardiac troponin/GDF 15 is formed, with the cardiac troponin being troponin T or troponin I, for example. By this, often a more profound information in respect to the treatment of the respective subject can be obtained. In general, a high ratio cardiac troponin/GDF-15 is often indicative of an appropriate medication suppressing inflammatory processes. Accordingly, a high ratio of the amount of a cardiac troponin to the amount of GDF-15, may indicate that no adaption of the therapy is necessary, and, thus, that the therapy can be continued. Accordingly, a low ratio of the amount of a cardiac troponin to the amount of GDF-15 indicates that the therapy should be adapted.

In an exemplary embodiment of the aforementioned method the ratio of the amount of a cardiac troponin to the amount of GDF-15 is formed, and compared to a reference ratio of the amount of a cardiac troponin to the amount of GDF-15. According to some embodiments, the reference ratio is derived from a subject for whom no therapy adaptation is necessary, or from a subject for whom the therapy shall be adapted (and, thus, from a subject who will benefit from therapy adaptation).

Preferably, an increased ratio of the amount of a cardiac troponin to the amount of GDF-15 in the sample from the subject to be tested as compared to the reference ratio indicates that no adaption of the therapy is necessary, and, thus, that the therapy can be continued (and thus, that the therapy shall not be changed), whereas a decreased ratio of the amount of a cardiac troponin to the amount of GDF-15 in the sample from the subject to be tested as compared to the reference ratio indicates that the therapy shall be adapted. Exemplary reference ratios are mentioned herein below.

In an exemplary embodiment of the present disclosure, the above mentioned ratio cardiac troponin/GDF 15 is used in connection with the individual concentrations. In general, a ratio troponin T/GDF-15 of $\geq$(equal to or higher than) about 0.01, such as about 0.017, is indicative that the medication is appropriate and should not be changed. On the contrary, a ratio troponin T/GDF-15 of < (lower than) about 0.01, such as about 0.005 is indicative that the medication is not appropriate and should be adapted.

In a further embodiment of the present disclosure, the ratio natriuretic peptide/GDF-15 is formed. The natriuretic peptide may be a BNP type or an ANP type natriuretic peptide, or BNP or NT-proBNP.

According to some embodiments of the aforementioned method the ratio of the amount of a natriuretic peptide to the amount of GDF-15 is formed, and compared to a reference ratio of the amount of a natriuretic peptide to the amount of GDF-15. According to some embodiments, the reference ratio is derived from a subject for which no therapy adaptation is necessary, or from a subject for which the therapy shall be adapted (and, thus, a subject who will benefit from therapy adaptation).

According to some embodiments, an increased ratio of the amount of a natriuretic peptide to the amount of GDF-15 in the sample from the subject to be tested as compared to the reference ratio indicates that no an adaption of the therapy is necessary, and, thus, that the therapy can be continued (and thus, shall not be changed), whereas a decreased ratio of the amount of a natriuretic peptide to the amount of GDF-15 in the sample from the subject to be tested as compared to the reference ratio indicates that the therapy shall be adapted. Exemplary reference ratios are mentioned herein below.

In general, a ratio NT-proBNP/GDF-15 of $\geq$ (equal to or higher than) about 0.8, for example about 1.9, is indicative that the medication is appropriate and should not be changed. On the contrary, a ratio NT-proBNP/GDF-15 of < (lower than) about 0.7, for example about 0.4 is indicative that the medication is not appropriate and should be adapted.

In the context of the method of monitoring a medication in a subject subjected to said medication and suffering from heart failure or stages preceding heart failure including risk factors for heart failure, at least in some cases, the following applies:

According to some embodiments, the ratio cardiac troponin/GDF 15 is formed, with the cardiac troponin being preferably troponin T or troponin I. By this, often a more profound information in respect to the treatment of the respective subject can be obtained. In general, a high ratio cardiac troponin/GDF-15 is often indicative of an appropriate medication suppressing inflammatory processes. Accordingly, a high ratio of the amount of a cardiac troponin to the amount of GDF-15, indicates that the therapy is appropriate, and, thus, that the therapy can be continued. Accordingly, a low ratio of the amount of a cardiac troponin to the amount of GDF-15 indicates that the therapy is not appropriate.

According to some embodiments of the aforementioned method the ratio of the amount of a cardiac troponin to the amount of GDF-15 is formed, and compared to a reference ratio of the amount of a cardiac troponin to the amount of GDF-15. In some cases, the reference ratio is derived from a subject for whom the therapy is appropriate, or from a subject for whom the therapy is not appropriate.

According to some embodiments, an increased ratio of the amount of a cardiac troponin to the amount of GDF-15 in the sample from the subject to be tested as compared to the reference ratio indicates that the therapy is appropriate (and thus, that therapy shall not be changed), whereas a decreased ratio of the amount of a cardiac troponin to the amount of GDF-15 in the sample from the subject to be tested as compared to the reference ratio indicates that the therapy is not appropriate. Exemplary reference ratios are mentioned herein below.

According to some embodiments of the present disclosure, the above mentioned ratio cardiac troponin/GDF 15 is used in connection with the individual concentrations. In general, a ratio troponin T/GDF-15 of equal to or higher than about 0.01, for example about 0.017, is indicative that the medication is appropriate. On the contrary, a ratio troponin T/GDF-15 of < (lower than) about 0.01, for example about 0.005 is indicative that the medication is not appropriate.

In a further embodiment of the present disclosure, the ratio natriuretic peptide/GDF-15 is formed. The natriuretic peptide may be a BNP type or an ANP type natriuretic peptide, for example NT-proBNP.

In a further embodiment of the aforementioned method the ratio of the amount of a natriuretic peptide to the amount of GDF-15 is formed, and compared to a reference ratio of the amount of a natriuretic peptide to the amount of GDF-15. According to some embodiments, the reference ratio is derived from a subject for whom the therapy is appropriate, or from a subject for whom the therapy is not appropriate.

According to some embodiments, an increased ratio of the amount of a natriuretic peptide to the amount of GDF-15 in the sample from the subject to be tested as compared to the reference ratio indicates that the therapy is appropriate, whereas a decreased ratio of the amount of a natriuretic peptide to the amount of GDF-15 in the sample from the subject to be tested as compared to the reference ratio indicates that the therapy is not appropriate. Exemplary reference ratios are mentioned herein below.

In general, a ratio NT-proBNP/GDF-15 of equal to or higher than about 0.8, for example about 1.9, is indicative that the medication is appropriate. On the contrary, a ratio NT-proBNP/GDF-15 of < (lower than) about 0.7, for example about 0.4 is indicative that the medication is not appropriate.

It is to be understood that the subjects of the present disclosure (suffering from either heart failure, such as classified stage C of the ACC/AHA classification; or having risk factors for heart failure or suffering from functional and/or structural abnormalities of the heart preceding heart failure, such as classified stage A or B of the ACC/AHA classification) already receive medication for the treatment of the aforementioned states, in general a medication selected from ACE inhibitors, angiotensin receptor blockers and aldosterone antagonists. In an embodiment, the subject does not receive administration of an aldosterone antagonist.

In the decision on the adaptation of the medication, an exemplary embodiment is the decision on the administration of an aldosterone antagonist, or the decision on the augmentation of the concentration of the aldosterone antagonist, or the decision on the administration of a different or a further aldosterone antagonist.

Accordingly, the therapy adaptation may be selected from i) the administration of an aldosterone antagonist, ii) the augmentation of the concentration (in particular the dosage) of the aldosterone antagonist, and iii) the administration of a different or a further aldosterone antagonist. According to some embodiments, i) is recommended if the subject did not receive aldosterone antagonists prior to carrying out the method (i.e. before the sample has been obtained). According to some embodiments, ii) or iii) is recommended if the subject did receive aldosterone antagonists prior to carrying out the method (i.e. before the sample has been obtained).

In case the concentrations of GDF-15 or a variant thereof in the individual show that inflammatory processes are predominant, in particular in consideration of the concentrations of a cardiac troponin in the individual showing heart failure or stages preceding heart failure, the medication should be adapted. According to some embodiments, administration of an aldosterone antagonist should be initiated.

In case the concentrations of a cardiac troponin or a variant thereof in the individual show that the individual suffers from heart failure and stages preceding heart failure, in particular in consideration of the concentrations of GDF-15 or a variant thereof in the individual showing inflammatory processes or not, the medication should be adapted if the GDF-15 concentration shows that inflammatory processes are predominant, and the medication should not be adapted if GDF-15 concentrations are not increased or only slightly increased in respect to healthy individuals, indicating that inflammatory processes are not existent or not predominant.

Collagen synthesis in the heart is believed to be a reason for diastolic dysfunction, as the left ventricle becomes stiffer as a consequence of collagen deposition between the cells. An impaired filling capacity results. Therefore, aldosterone antagonists appear to be in particular appropriate for treating individuals who are at risk of suffering from diastolic dysfunction, or who are about to develop diastolic dysfunction, or who suffer from diastolic dysfunction which may worsen.

In the context of the present embodiment of the present disclosure, the terms "decreased" and "increased" refer to the average values in a healthy subject. These values are known to the person skilled in the art and are as follows: about 2.0 pg/mL, or about 3 pg/ml for troponin T (or 0.0 pg/mL taking into account the test's sensitivity of about 2.0); about 680 pg/ml, about 580 pg/mL, about 500 pg/mL for GDF-15; about 68 pg/ml, about 37 pg/mL, about 18 pg/mL for NT-proBNP.

As known to the person skilled in the art mean average values of NT-ProBNP in healthy subjects increase with age (e.g. 37 pg/mL at age 18-44, 72 pg/ml at age 55-64, 107 pg/ml at age 65-74, 211 pg/ml at age above 75). The person skilled in the art considers this when assessing whether the amount of natriuretic peptide is increased. Thus, whether an amount of a natriuretic peptide is increased, e.g. by at least 20% in respect to the amount in a sample from a healthy individual, can be determined by the skilled person without further ado.

The terms "decreased" or "increased" as used in the context of the present disclosure denote in case of GDF-15 an increase or decrease of at least 10%, at least 20% in respect to healthy individuals; in case of troponin T and NT-proBNP, the terms "decreased" or "increased" as used in the context of the present disclosure denote an increase or decrease of at least 20%, at least 30%, in respect to healthy individuals. Accordingly, an increase of at least 20%, at least 30% of a cardiac troponin, of troponin T, in respect to the amount in a sample from a healthy subject or in respect to the amount in a sample from a subject bearing risk factors of heart failure, but not having functional and/or structural abnormalities preceding heart failure (for example in a stage A subject) is indicative for the diagnosis of functional and/or structural abnormalities preceding heart failure and/or preceding left ventricular hypertrophy. Further embodiments include an increase of at least 50% of a cardiac troponin, such as of troponin T, in respect to the aformentioned amounts is indicative for the diagnosis of functional and/or structural abnormalities preceding heart failure and/or preceding left ventricular hypertrophy. According to some embodiments, the risk factors of the test subject and the reference subject are the same.

A healthy subject/individual may be a subject not bearing risk factors of heart failure, in particular a normotensive subject (see e.g. group 1 in Example 1). According to some embodiments, said subject is a subject not bearing risk factors of heart failure and not having functional and structural abnormalities of the heart preceding heart failure and/or preceding left ventricular hypertrophy. Is a further embodiment that the healthy subject may be a subject bearing risk factors of heart failure, but not having functional and/or structural abnormalities preceding heart failure and/or preceding LVH (see e.g. group 2 in Example 1). For example, the subject bearing risk factors of heart failure, but not having functional and/or structural abnormalities preceding heart failure and/or preceding LVH is a stage A subject. If the healthy subject bears risk factors of heart disease, the subject to be tested bears the same risk factors.

According to some embodiments, an amount of a cardiac troponin in sample from a test subject which is decreased or which is essentially same as compared to the amount of a cardiac troponin in a sample from a healthy subject (or from a subject bearing risk factors of heart failure, but not having functional and/or structural abnormalities preceding heart failure (in particular in a stage A subject) indicates that the subject does not suffer from functional and/or structural abnormalities preceding heart failure and/or preceding left ventricular hypertrophy.

Particular reference amounts for troponin T that may serve as cut-off amount include, for example, 3.3 pg/ml and 3.5 pg/ml. An exemplary reference amount for troponin I that may serve as cut-off amount includes 9 pg/ml. An exemplary reference range may be 0.2 up to 9 pg/ml. An amount of a cardiac troponin in a sample, such as a serum or plasma sample, from a subject larger than the reference amount may indicate that the subject suffers from structural or functional abnormalities of the heart preceding heart failure and/or preceding left ventricular hypertrophy. An amount of a cardiac troponin in sample from a subject lower than the reference amount may indicate that the subject does not suffer from structural or functional abnormalities of the heart preceding heart failure and/or preceding left ventricular hypertrophy.

Particular reference amounts for IGFBP7 that may serve as cut-off amount include 42.6 pg/ml and 46.2 pg/ml. An exemplary reference range is 33.3 pg/ml to 46.2 pg/ml.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present disclosure comprise ANP-type and BNP-type peptides and variants thereof (see e.g. Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Natriuretic peptides according to the present disclosure include NT-proANP, ANP, and NT-proBNP, BNP, and variants thereof. ANP and BNP are the active hormones and have a shorter half-life than their respective inactive counterparts, NT-proANP and NT-proBNP. BNP is metabolized in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46). Preanalytics are more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73). Therefore, depending on the time-course or properties of interest, either measurement of the active or the inactive forms of the natriuretic peptide can be advantageous. Exemplary natriuretic peptides according to the present disclosure are NT-proBNP or variants thereof. As briefly discussed above, the human NT-proBNP, as referred to in accordance with the present disclosure, is a polypeptide comprising, for example, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. According to some embodiments, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present disclosure further encompasses allelic and other variants of said specific sequence for human NT-proBNP discussed above. Specifically, envisaged are variant polypeptides which are (on the amino acid level) at least 50%, 60%, 70%, 80%, 85%, 90%, 92%, 95%, 97%, 98%, or 99% identical to human NT-proBNP, for example over the entire length of human NT-proBNP. The degree of identity between two amino acid sequences can be determined by algorithms well known in the art. According to some embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT may be employed to determine their optimal alignment and, thus, the degree of identity. According to some embodiments, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. According to some embodiments, NT-proBNP variants have immunological properties (i.e. epitope composition) comparable to those of human NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Lab Invest 230:177-181), Yeo et al. (Yeo 2003, Clinica Chimica Acta 338:107-115). Variants also include posttranslationally modified peptides such as glycosylated peptides. Further, a variant in accordance with the present disclosure is also a peptide or polypeptide which has been modified after collection of the sample, for example by covalent or non-covalent attachment of a label, particularly a radioactive or fluorescent label, to the peptide.

It is to be understood that the subjects which are in the context of the present embodiment of the disclosure (namely methods of therapy monitoring and therapy adaptation in a subject receiving administration of a medicament selected from ACE inhibitors, angiotensin receptor blockers and aldosterone antagonists) should not suffer from diseases which affect the concentrations of the markers cited in respect to individuals not suffering from the cardiac abnormalities or diseases which are the subject-matter of the present disclosure. Accordingly, the subject should be clinically healthy except for heart failure/functional and/or structural abnormalities of the heart preceding heart failure, and for risk factor of suffering from heart failure. Furthermore, the subject should not suffer from diabetes mellitus, should not have liver disease, should not be pregnant and should not suffer from malignancies.

The person skilled in the art is aware that the concentrations cited in the present application for the cardiac troponins (troponin T or a variant thereof and troponin I or a variant thereof), NT-proBNP or a variant thereof and—to a lesser extent—for GDF-15 or a variant thereof may not apply for patients suffering from impaired renal function, for example some patients suffering from renal failure such as patients suffering from chronic and end stage renal failure. In an exemplary embodiment of the present disclosure, patients suffering from impaired renal function such as renal failure, including chronic and end stage renal failure are not comprised in (excluded from) the methods of the present disclosure. In another embodiment, patients with renal hypertension are not comprised in (excluded from) the methods of the present disclosure.

According to some embodiments, the "subject" as used herein excludes patients suffering from impaired renal function, for example patients suffering from renal failure, e.g., from chronic and end stage renal failure and renal hypertension. In this context, "renal failure" is regarded as an impaired glomerular filtration rate (GFR) lying below the usual ranges of 60 to 120 ml/min, preferably below 60 ml/min. Chronic renal failure is a long-standing, progressive deterioration of renal function which often results in end stage renal failure. End stage renal failure is diagnosed when the GFR reaches a rate of up to about 30 ml/min. GFR is determined by the creatinine clearance, which is known to the person skilled in the art. Subjects with impaired renal function show higher levels of troponin I and troponin T than those cited above, due to an impaired clearance of the peptide. The levels vary with the severity of the renal impairment.

The severity of renal impairment is divided into various grades, as displayed below.
0: ≥90 ml/min
1: ≥90 ml/min with microalbuminuria
2: ≥60-<90 ml/min
3: ≥30-<60 ml/min
4: ≥15-<30 ml/min
5: <15 ml/min
(Source: National Kidney Foundation, as published in: Am J. Kidney Dis 39 suppl 1, 2002; Clinical Practice Guidelines for chronic kidney disease).

The subject as set forth herein shall be, preferably, about to leave stage A and about to enter stage B (or shall have entered early stage B). Accordingly, the subject, preferably, shall have no history of myocardial infarction, in particular shall have no history of known myocardial infarction. Thus, the term "subject" as used herein, according to some embodiments, excludes a subject having a history of known myocardial infarction. This applies, for example, to the methods of diagnosing, methods of differentiating, methods of monitoring a medication, and methods of predicting as set forth herein.

A subject who has no history of known myocardial infarction (MI) in general will not have suffered from myocardial infarction (in particular from diagnosed myocardial infarction) in the past, i.e. before the sample to be tested has been obtained. The term "myocardial infarction" is well known in the art. As used herein, the term includes ST-elevation MI (STEMI) and non-ST-elevated MI (NSTEMI).

Also, the term "subject" as used herein may, exclude a subject who suffers from coronary artery disease. Thus, the subject to be tested shall not suffer from coronary artery disease. This applies, in particular, to the methods of diagnosing, methods of differentiating, methods of monitoring a medication, and methods of predicting as set forth herein.

The term "coronary artery disease" (CAD, frequently also called coronary heart disease (CHD) is known to the person skilled in the art. The term refers to a condition in which at least one of the major coronary arteries is narrowed, whereby stenosis of more than 50% should occur per vessel, for example. A subject not suffering from CAD, has less than 50% stenosis (and thus less than 50% occlusion) of the major coronary arteries. How to assess the degree of occlusion of a coronary artery is well known in the art, for example the degree may be assessed by coronary angiography.

Moreover, according to some embodiments the subject to be tested in the context of the methods of the present disclosure does not have increased levels of a natriuretic peptide. This applies, for example, to the methods of diagnosing, methods of differentiating, methods of monitoring a medication, and methods of predicting as set forth herein. According to some embodiments, the subject does not have increased levels of a brain natriuretic peptide. According to some embodiments, the subject does not have increased levels of a BNP-type natriuretic peptide. According to some embodiments, the subject does not have increased levels of NT-proBNP.

A subject who does not have increased levels of a natriuretic peptide, for example NT-proBNP, according to some embodiments may have less than 20% increase of a natriuretic peptide, in respect to healthy individuals and, according to some embodiments in respect to the amount in a sample from a healthy subject bearing risk factors of heart failure, but not having functional and/or structural abnormalities preceding LVH and/or heart failure (in particular in a stage A subject)) in respect to the amount in a sample from a subject bearing the same risk factors of heart failure and having functional and/or structural abnormalities preceding LVH and/or preceding heart failure (for example in an early stage B subject). According to some embodiments, the subject has a level of NT-proBNP of less than 10% as compared to the aforementioned levels. According to the disclosure, the aforementioned levels apply to serum levels.

The term "sample" refers to a sample of a body fluid, to a sample of separated cells or to a sample from a tissue or an organ. Samples of body fluids can be obtained by well known techniques and include, samples of blood, plasma, serum, urine, samples of blood, plasma or serum. It is to be understood that the sample depends on the marker to be determined. Therefore, it is encompassed that the polypeptides as referred to herein are determined in different samples. Cardiac troponins or a variant thereof, NT-proBNP or a variant thereof, GDF 15 or a variant thereof and IGFBP7 or a variant thereof are, for example, determined in a blood serum or blood plasma sample.

In accordance with the present disclosure, determining the concentration of a peptide or polypeptide can be achieved by all known means for determining the concentration of a peptide in a sample (the terms "concentration", "level" and "amount" are used interchangeably herein). Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, according to some embodiments, be correlated directly or indirectly (e.g. reverse-proportional) to the concentration of polypeptide present in a sample. Further suitable methods comprise measuring a physical or chemical property specific for the peptide or polypeptide such as its precise molecular mass or NMR spectrum. Said methods comprise, for example, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

According to some embodiments, determining the concentration of a peptide or polypeptide comprises the steps of (a) contacting a cell capable of eliciting a cellular response the intensity of which is indicative of the concentration of the peptide or polypeptide with the said peptide or polypeptide for an adequate period of time, (b) measuring the cellular response. For measuring cellular responses, the sample or processed sample is, in some embodiments, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the concentration of the peptide or polypeptide.

Also according to some embodiments, determining the concentration of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the concentration of a peptide or polypeptide may comprise the steps of (a) contacting the peptide with a specific ligand, (b) (optionally) removing non-bound ligand, (c) measuring the concentration of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. According to some embodiments, the ligand or agent binds specifically to the peptide or polypeptide. Specific binding according to the present disclosure means that the ligand or agent should not bind substantially to ("cross-react" with) another peptide, polypeptide or substance present in the sample to be analyzed. According to some embodiments, the specifically bound peptide or polypeptide should be bound with at least 3 times higher, at least 10 times higher and in some cases even at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. According to some embodiments, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the concentration of a protease can be measured by measuring the concentration of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the concentration of substrate is saturating. The substrate may also be labeled with a detectable label prior to the reaction. Preferably, the sample is contacted with the substrate for an adequate period of time. An adequate period of time refers to the time necessary for a detectable, preferably measurable, concentration of product to be produced. Instead of measuring the concentration of product, the time necessary for appearance of a given (e.g. detectable) concentration of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag may be at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The concentration of a peptide or polypeptide may be determined as follows: (a) contacting a solid support comprising a ligand for the peptide or polypeptide as specified above with a sample comprising the peptide or polypeptide and (b) measuring the concentration peptide or polypeptide which is bound to the support. The ligand, may be chosen from the group consisting of nucleic acids, peptides, polypeptides, antibodies and aptamers, and may be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "concentration" as used herein encompasses the absolute concentration of a polypeptide or peptide, the relative concentration or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned concentrations or parameters can also be obtained by all standard mathematical operations.

The present disclosure further encompasses a device adapted for carrying out the methods of the present disclosure, comprising:
a) means for determining the concentrations of the following peptides: a cardiac troponin or a variant thereof, for example troponin T or troponin I or variants thereof; and optionally one or more of the following means: means for determining the concentrations of an inflammatory marker, for example GDF-15 or a variant thereof; and/or means for determining the concentration of IGFBP7 or a variant thereof;

b) means for comparing the concentrations determined in step a) with respective concentrations of said markers in control samples, whereby the methods of the present disclosure are carried out.

The device is adapted for carrying out the methods of the present disclosure. The methods of the present disclosure include the following:
diagnosing functional and/or structural abnormalities of the heart preceding heart failure, in a subject bearing risk factors of developing heart failure and/or respective stroke and/or respective chronic kidney disease; and/or
differentiating, in a subject bearing risk factors of developing heart failure, if the subject only bears risk factors or if the subject already suffers from functional and/or structural abnormalities of the heart preceding heart failure; and/or
predicting the risk of a subject bearing risk factors of developing heart failure, to suffer from heart failure.

In general, the subject (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. According to some embodiments, the subject bears risk factors for heart failure. These are known to the person skilled in the art and include e.g. hypertension and diabetes. Also, the subject may not show overt signs and/or symptoms of heart failure.

Depending on the results obtainable by the device according to the disclosure, a decision on the therapy or therapy adaptation may be taken. The therapy may be adapted by e.g. augmenting or diminishing the concentrations of the medicaments which are administrated. Accordingly, the device is also adapted for monitoring the said therapy.

The present disclosure also relates to the use of a device or devices as cited beforehand, for: diagnosing functional and/or structural abnormalities of the heart preceding heart failure, in a subject bearing risk factors of developing heart failure; and/or stroke and/or chronic kidney disease;
differentiating, in a subject bearing risk factors of developing heart failure, if the subject only bears risk factors or if the subject already suffers from functional and/or structural abnormalities of the heart preceding heart failure; and/or
predicting the risk of a subject bearing risk factors of developing heart failure, to suffer from heart failure.

In general, the subject (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. According to some embodiments, the subject bears risk factors for heart failure. These are known to the person skilled in the art and include e.g. hypertension and diabetes. Also according to some embodiments, the subject does not show overt signs and/or symptoms of heart failure.

Depending on the results obtainable by the use of the device according to the disclosure, a decision on the therapy or therapy adaptation may be taken. The therapy may be adapted by e.g. augmenting or diminishing the concentrations of the medicaments which are administrated. Accordingly, the device can also be used for monitoring the said therapy.

The term "device" as used herein relates to a system of means comprising at least the aforementioned means operatively linked to each other as to allow the prediction. Exemplary means for determining the concentration of a one of the aforementioned polypeptides as well as means for carrying out the comparison are disclosed above in connection with the method of the disclosure. How to link the means in an operating manner will depend on the type of means included into the device. For example, where means for automatically determining the concentration of the peptides are applied, the data obtained by said automatically operating means can be processed by, e.g., a computer program in order to obtain the desired results. According to some embodiments, the means are comprised by a single device in such a case. Said device may accordingly include an analyzing unit for the measurement of the concentration of the peptides or polypeptides in an applied sample and a computer unit for processing the resulting data for the evaluation. The computer unit, for example, may comprise a database including the stored reference concentrations or values thereof recited elsewhere in this specification as well as a computer-implemented algorithm for carrying out a comparison of the determined concentrations for the polypeptides with the stored reference concentrations of the database. Computer-implemented as used herein refers to a computer-readable program code tangibly included into the computer unit. Alternatively, where means such as test stripes are used for determining the concentration of the peptides or polypeptides, the means for comparison may comprise control stripes or tables allocating the determined concentration to a reference concentration. The test strips are, for example, coupled to a ligand which specifically binds to the peptides or polypeptides referred to herein. The strip or device, according to some embodiments, comprises means for detection of the binding of said peptides or polypeptides to the said ligand. Exemplary means for detection are disclosed in connection with embodiments relating to the method of the disclosure above. In such a case, the means are operatively linked in that the user of the system brings together the result of the determination of the concentration and the diagnostic or prognostic value thereof due to the instructions and interpretations given in a manual. The means may appear as separate devices in such an embodiment and are, for example, packaged together as a kit. The person skilled in the art will realize how to link the means without further ado. Exemplary devices are those which can be applied without the particular knowledge of a specialized clinician, e.g., test strips or electronic devices which merely require loading with a sample. The results may be given as output of raw data which need interpretation by the clinician. According to some embodiments, the output of the device is, however, processed, i.e. evaluated, raw data the interpretation of which does not require a clinician. Further, some devices comprise the analyzing units/devices (e.g., biosensors, arrays, solid supports coupled to ligands specifically recognizing the cardiac troponin, IGFBP7 or GDF 15, Plasmon surface resonance devices, NMR spectrometers, mass-spectrometers etc.) and/or evaluation units/devices referred to above in accordance with the method of the disclosure.

The present disclosure also relates to the use of a device as cited beforehand, for monitoring the therapy in a subject diagnosing functional and/or structural abnormalities of the heart preceding heart failure, in a subject bearing risk factors of developing heart failure.

Moreover, the present disclosure relates to a kit adapted for carrying out the methods of the present disclosure referred to above comprising:
 a) means for determining the concentrations of the following peptides: a cardiac troponin or a variant thereof, preferably troponin T or a variant thereof; an inflammatory marker, preferably GDF-15 or a variant thereof; IGFBP7 or a variant thereof, and
 b) means for comparing the concentrations determined in step a) with respective concentrations of said markers in control samples, whereby the methods of the present disclosure are carried out.

The kit is adapted for carrying out the method of the present disclosure referred to above. According to some embodiments, the kit comprises instructions for carrying out the said method of the present disclosure.

The methods of the present disclosure include the following:
 diagnosing functional and/or structural abnormalities of the heart preceding heart failure, in a subject bearing risk factors of developing heart failure; and/or
 differentiating, in a subject bearing risk factors of developing heart failure, if the subject only bears risk factors or if the subject already suffers from functional and/or structural abnormalities of the heart preceding heart failure; and/or
 predicting the risk of a subject bearing risk factors of developing heart failure, to suffer from heart failure.

In general, the subject (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. According to some embodiments, the subject bears risk factors for heart failure. These are known to the person skilled in the art and include e.g. hypertension and diabetes. Also according to some embodiments, the subject does not show overt signs and/or symptoms of heart failure.

Depending on the results obtainable by the kit according to the disclosure, a decision on the therapy or therapy adaptation may be taken. The therapy may be adapted by e.g. augmenting or diminishing the concentrations of the medicaments which are administrated. Accordingly, the kit is also adapted for monitoring the said therapy.

The present disclosure also relates to the use of a kit or kits as cited beforehand, for: diagnosing functional and/or structural abnormalities of the heart preceding heart failure, in a subject bearing risk factors of developing heart failure; and/or respective of developing stroke, and/or respective of developing chronic kidney disease,
 differentiating, in a subject bearing risk factors of developing heart failure, if the subject only bears risk factors or if the subject already suffers from functional and/or structural abnormalities of the heart preceding heart failure; and/or
 predicting the risk of a subject bearing risk factors of developing heart failure, to suffer from heart failure.

In general, the subject (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. According to some embodiments, the subject bears risk factors for heart failure. These are known to the person skilled in the art and include e.g. hypertension and diabetes. Also according to some embodiments, the subject does not show overt signs and/or symptoms of heart failure.

Depending on the results obtainable by the use of the kit according to the disclosure, a decision on the therapy or therapy adaptation may be taken. The therapy may be adapted by e.g. augmenting or diminishing the concentrations of the medicaments which are administrated. Accordingly, in some embodiments, the kit can also be used for monitoring the said therapy.

The term "kit" as used herein refers to a collection of the aforementioned means, for example, provided in separately or within a single container. The container may comprise instructions for carrying out the method of the present disclosure.

The present disclosure also relates to uses of the kits, devices and means, for example, as indicated below:
 Use of a kit or device for determining the concentration of: a cardiac troponin or a variant thereof, for example Troponin T or a variant thereof and/or Troponin I or a variant thereof; and, as the case may be, GDF-15 or a variant thereof; and/or IGFBP7 or a variant thereof in a sample of a subject; and the use of a means for determining the concentration of: a cardiac troponin or a variant thereof, Troponin T or a variant thereof and/or Troponin I or a variant thereof; and, as the case may be, GDF-15 or a variant thereof; and/or IGFBP7 or a variant thereof; and the use of a means for comparing the concentration of a cardiac troponin or a variant thereof, Troponin T or a variant thereof and/or Troponin I or a variant thereof; and, as the case may be, GDF-15 or a variant thereof; and/or IGFBP7 or a variant thereof, to the concentration of at least one of said markers in a control sample for:
 diagnosing functional and/or structural abnormalities of the heart preceding heart failure, in a subject bearing risk factors of developing heart failure; and/or
 differentiating, in a subject bearing risk factors of developing heart failure but not showing overt signs of heart failure, if the subject only bears risk factors or if the subject already suffers from functional and/or structural abnormalities of the heart preceding heart failure; and/or
 predicting the risk of a subject bearing risk factors of developing heart failure to suffer from heart failure,
 and wherein all uses are based on diagnosing functional and/or structural abnormalities of the heart preceding heart failure in a subject bearing risk factors of developing heart failure.

The present disclosure also relates to the use of the following antibodies and means, for example, as indicated below:
 Use of an antibody to a cardiac troponin or a variant thereof, for example Troponin T or a variant thereof and/or Troponin I or a variant thereof; and, as the case may be, an antibody to GDF-15 or a variant thereof and/or an antibody to IGFBP7 or a variant thereof, and/or of means for determining the concentration of a cardiac troponin or a variant thereof, for example Troponin T or a variant thereof and/or Troponin I or a variant thereof; and, as the case may be, means for determining the concentration of GDF-15 or a variant thereof and/or of means for determining the concentration of IGFBP7 or a variant thereof, and/or of means for comparing the concentration of a cardiac troponin or a variant thereof, for example Troponin T or a variant thereof and/or Troponin I or a variant thereof; and, as the case may be, the concentrations of GDF-15 or a variant thereof and/or IGFBP7 or a variant thereof, to the concentration at least one of the said markers in a control sample for the manufacture of a diagnostic composition for:

diagnosing functional and/or structural abnormalities of the heart preceding heart failure, in a subject bearing risk factors of developing heart failure; and/or differentiating, in a subject bearing risk factors of developing heart failure, if the subject only bears risk factors or if the subject already suffers from functional and/or structural abnormalities of the heart preceding heart failure; and/or predicting the risk of a subject bearing risk factors of developing heart failure, to suffer from heart failure;

and wherein all uses are based on diagnosing functional and/or structural abnormalities of the heart preceding heart failure in a subject bearing risk factors of developing heart failure.

The present disclosure also relates to the use of the following antibodies and means, for example, as indicated below:

Use of an antibody to a cardiac troponin or a variant thereof, for example Troponin T or a variant thereof and/or Troponin I or a variant thereof; and, as the case may be, an antibody to GDF-15 or a variant thereof and/or an antibody to IGFBP7 or a variant thereof, and/or of means for determining the concentration of a cardiac troponin or a variant thereof, for example Troponin T or a variant thereof and/or Troponin I or a variant thereof; and, as the case may be, means for determining the concentration of GDF-15 or a variant thereof and/or of means for determining the concentration of IGFBP7 or a variant thereof, and/or of means for comparing the concentration of a cardiac troponin or a variant thereof, for example Troponin T or a variant thereof and/or Troponin I or a variant thereof; and, as the case may be, the concentrations of GDF-15 or a variant thereof and/or IGFBP7 or a variant thereof, to the concentration of at least one of the said markers in a control sample for:

diagnosing functional and/or structural abnormalities of the heart preceding heart failure, in a subject bearing risk factors of developing heart failure; and/or differentiating, in a subject bearing risk factors of developing heart failure, if the subject only bears risk factors or if the subject already suffers from myocardial dysfunction and/or structural functional and/or structural abnormalities of the heart preceding heart failure; and/or predicting the risk of a subject bearing risk factors of developing heart failure, to suffer from heart failure, and wherein all uses are based on diagnosing functional and/or structural abnormalities of the heart preceding heart failure in a subject bearing risk factors of developing heart failure.

Moreover, the present disclosure relates to the use of an antibody that specifically binds to a cardiac troponin or a variant thereof, for example Troponin T or a variant thereof and/or Troponin I or a variant thereof; and, as the case may be, an antibody that specifically binds to GDF-15 or a variant thereof and/or an antibody that specifically binds to IGFBP7 or a variant thereof, in a sample of a female subject, for predicting the risk of a female subject bearing risk factors of developing heart failure to suffer from LVH.

In general, the subject referred to above in connection with the uses of the disclosure as specified above (i.e. the individual bearing risk factors and/or suffering from functional and/or structural abnormalities of the heart preceding heart failure) does not suffer from heart failure, i.e. the patient has not experienced permanent structural or functional damages to his myocardium, and he will be able to fully restore his health, and he is not classified into stage C or D of the ACC/AHA classification. According to some embodiments, the subject bears risk factors for heart failure. These are known to the person skilled in the art and include e.g. hypertension and diabetes. Also according to some embodiments, the subject does not show overt signs and/or symptoms of heart failure.

The uses of the present disclosure, as specified beforehand, according to some embodiments, are in vitro methods.

The following examples, illustrative embodiments, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method of diagnosing functional and/or structural abnormalities of the heart preceding heart failure in a subject suffering from hypertension, diabetes, obesity, metabolic syndrome and/or having a history of smoking, the method comprising the steps of:

a) measuring in a sample obtained from the subject the concentration of at least one cardiac troponin or a variant thereof, b) optionally measuring in the sample the concentration of one or more other marker(s) of heart failure, and c) diagnosing said functional and/or structural abnormalities by comparing the concentration determined in step (a) and optionally the concentration(s) determined in step (b) with a reference amount wherein the subject does not show left ventricular hypertrophy, and wherein the structural and/or functional abnormalities of the heart preceding heart failure comprise an abnormality selected from a left ventricular structural change, an increased septum diameter, an increased posterial wall diameter, and diastolic dysfunction.

2. The method according to 1, wherein the subject does not suffer from heart failure or does not display symptoms of heart failure.

3. The method according to any of 1 to 2, wherein the cardiac troponin is troponin I or T or a variant thereof.

4. The method according to any of 1 to 3, wherein the subject suffers from hypertension, in particular arterial hypertension, and/or diabetes, in particular type 2 diabetes.

5. The method of any of 1 to 4, wherein the functional and/or structural abnormalities of the heart preceding heart failure are structural and/or functional abnormalities of the heart preceding heart failure and/or left ventricular hypertrophy.

6. The method of any of 1 to 5, wherein the functional and/or structural abnormality is an increased septum diameter.

7. The method of any of 1 to 6, wherein the functional and/or structural abnormality is a diastolic dysfunction, in particular diastolic dysfunction asymptomatic diastolic left ventricular dysfunction with preserved left ventricular ejection fraction (LVEF).

8. The method of any of 1 to 7, wherein the subject does not have increased NT-proBNP levels, in particular, wherein the subject has no increase of NT-ProBNP compared to a reference amount of at least 20% or of at least 30%, in particular to the amount of NT-proBNP in healthy individuals.

9. The method of any of 1 to 8, wherein an increase of at least 20%, in particular, of at least 30% of a cardiac Troponin, in particular of Troponin T, in respect to the amount in healthy individuals is indicative for the diagnosis of functional and/or structural abnormalities of the heart preceding heart failure.

10. The method according to any of 1 to 9, wherein the one or more other marker(s) of heart failure is selected from GDF-15 or a variant thereof, and/or IGFBP7 or a variant thereof.

11. A method of differentiating between a subject only bearing risk factors of developing heart failure and a subject not only bearing risk factors but already suffering from functional and/or structural abnormalities of the heart preceding heart failure, the method comprising the steps of:
   a) measuring in a sample obtained from the subject the concentration of at least one cardiac troponin or a variant thereof,
   b) optionally measuring in the sample the concentration of one or more other marker(s) of heart failure, and
   c) differentiating between said subjects by comparing the concentration determined in step (a) and optionally the concentration(s) determined in step (b) with a reference amount,
wherein the subject does not show left ventricular hypertrophy, and
wherein the structural and/or functional abnormalities of the heart preceding heart failure comprise an abnormality selected from a left ventricular structural change, an increased septum diameter, an increased posterial wall diameter, and diastolic dysfunction.

12. The method of 11, wherein the subject suffers from hypertension.

13. A method of predicting the risk of a female subject to suffer from left ventricular hypertrophy, the method comprising the steps of:
   a) measuring in a sample obtained from the subject the concentration of at least one cardiac troponin or a variant thereof,
   b) optionally measuring in the sample the concentration of one or more other marker(s) of heart failure, and
   c) predicting the risk of the subjects to suffer from left ventricular hypertrophy by comparing the concentration determined in step (a) and optionally the concentration(s) determined in step (b) with a reference amount.

14. The method of 13, wherein the subject bears at least one risk factor of heart failure.

15. The method of 14, wherein the subject bearing at least one risk factor suffers from hypertension.

16. The method of any of 13 to 15, wherein the reference amount is derived from a healthy female subject or a group thereof, and wherein an increase of a cardiac troponin, such as of troponin T of at least 30%, in particular of at least 50% as compared to the reference amount is indicative for a risk of the subject to suffer from left ventricular hypertrophy.

17. A method of monitoring a medication in a subject subjected to said medication, said medication being selected from ACE inhibitors, angiotension receptor blockers and aldosterone antagonists, said subject suffering from heart failure or stages preceding heart failure including risk factors for heart failure, the method comprising the steps of:
   a) measuring in a sample obtained from the subject the concentrations of at least one cardiac troponin or a variant thereof and/or a natriuretic peptide or a variant thereof,
   b) measuring in a sample the concentration of GDF-15 or a variant thereof, and
   c) monitoring the medication by comparing the thus determined concentrations with a reference amount.

18. A method of deciding on the adaptation of a medication selected from ACE inhibitors, angiotension receptor blockers and aldosterone antagonists in a subject subjected to said medication and suffering from heart failure or stages preceding heart failure including risk factors for heart failure, the method comprising the steps of:
   a) measuring in a sample obtained from the subject the concentrations of at least one cardiac troponin or a variant thereof and/or a natriuretic peptide or a variant thereof,
   b) measuring in a sample the concentration of GDF-15 or a variant thereof, and
   c) deciding on the adaptation of the medication by comparing the thus determined concentrations with a reference amount.

19. The method according to 17 or 18, wherein the medication is an ACE inhibitor.

20. The method according any of 17 to 19, wherein the concentrations of a cardiac troponin, in particular troponin T, and GDF-15 are measured, and wherein a ratio of the cardiac troponin and GDF-15 (cardiac Troponin/GDF-15) is formed.

21. The method according to 20, wherein a ratio of troponin T/GDF-15 of equal to or higher than about 0.01, in some cases equal to higher than about 0.017, is indicative that the medication is appropriate and should not be changed, and/or wherein a ratio troponin T/GDF-15 of lower than about 0.01, and ins some cases lower than about 0.005 is indicative that the medication is not appropriate and should be adapted.

22. The method according any of 17 to 19, wherein the concentrations of a natriuretic peptide, in particular NT-proBNP, and GDF-15 are measured, and wherein a ratio of the natriuretic peptide and GDF-15 (natriuretic peptide/GDF-15) is formed.

23. The method according to 22, wherein a ratio of NT-proBNP/GDF-15 of equal to or higher than about 0.8, in some cases equal to or higher than about 1.9, is indicative that the medication is appropriate and should not be changed, and/or wherein a ratio NT-proBNP/GDF-15 of lower than about 0.7, and in some cases lower than about 0.4 is indicative that the medication is not appropriate and should be adapted.

24. The method according to any of 18 to 23, wherein the adaptation is selected from i) the administration of an aldosterone antagonist, ii) the augmentation of the concentration of the aldosterone antagonist, and iii) the administration of a different or a further aldosterone antagonist.

25. In vitro use of a cardiac Troponin, or of an antibody which specifically binds to a cardiac Troponin for diagnosing functional and/or structural abnormalities of the heart preceding heart failure as defined in 1 (above) in a subject suffering from hypertension, diabetes, obesity, metabolic syndrome and/or having a history of smoking, wherein the subject does not show left ventricular hypertrophy.

26. In vitro use of a cardiac Troponin, or of an antibody which specifically binds to a cardiac Troponin for differentiating between a subject suffering from stage A heart failure and a subject suffering from early stage B heart failure.

27. In vitro use of a cardiac Troponin, or of an antibody which specifically binds to a cardiac Troponin for differentiating between a subject only bearing risk factors of developing heart failure and a subject not only bearing risk factors but already suffering from functional and/or structural abnormalities of the heart preceding heart failure as defined in 1 (above), wherein the subject does not show LVH.

28. In vitro use of a cardiac Troponin, or of an antibody which specifically binds to a cardiac Troponin for predicting the risk of a female subject to suffer from left ventricular hypertrophy.

29. The in vitro use of 25 to 28, further comprising the use of one or more other marker(s) of heart failure, in particular of GDF-15 and/or IGFBP7, or of an antibody (antibodies) which specifically binds to said one or marker(s) of heart failure.

30. A method of diagnosing in a subject functional and/or structural abnormalities of the heart preceding heart failure, the method comprising the steps of:
    a) measuring in a sample obtained from the subject the concentration of at least one cardiac troponin or a variant thereof,
    b) optionally measuring in the sample the concentration of one or more other marker(s) of heart failure, and
    c) diagnosing said functional and/or structural abnormalities by comparing the concentration determined in step (a) and optionally the concentration(s) determined in step (b) with a reference amount.

31. The method according to 30, wherein the subject does not suffer from heart failure or does not display symptoms of heart failure.

32. The method according to any of 30 to 31, wherein the cardiac troponin is troponin I or T or a variant thereof.

33. The method according to any of 30 to 32, wherein the subject suffers from left ventricular dysfunction.

34. The method according to any of 30 to 33, wherein the one or more other marker(s) of heart failure is selected from GDF-15 or a variant thereof, and/or IGFBP7 or a variant thereof.

35. A method of differentiating between a subject only bearing risk factors of developing heart failure and a subject not only bearing risk factors but already suffering from functional and/or structural abnormalities of the heart preceding heart failure, the method comprising the steps of:
    a) measuring in a sample obtained from the subject the concentration of at least one cardiac troponin or a variant thereof,
    b) optionally measuring in the sample the concentration of one or more other marker(s) of heart failure, and
    c) differentiating between said subjects by comparing the concentration determined in step (a) and optionally the concentration(s) determined in step (b) with a reference amount.

36. A method of predicting the risk of a subject to suffer from heart failure, or respective cardiovascular and renal events preceding heart failure, the method comprising the steps of
    a) measuring in a sample obtained from the subject the concentration of at least one cardiac troponin or a variant thereof,
    b) optionally measuring in the sample the concentration of one or more other marker(s) of heart failure, and
    c) predicting the risk of the subjects to suffer from heart failure by comparing the concentration determined in step (a) and optionally the concentration(s) determined in step (b) with a reference amount.

37. The method according to 36, wherein the subject suffers from a left ventricular dysfunction such as a diastolic dysfunction.

38. A method of deciding on the treatment of functional and/or structural abnormalities of the heart preceding heart failure in a subject, the method comprising the steps of
    a) measuring in a sample obtained from the subject the concentration of at least one cardiac troponin or a variant thereof,
    b) optionally measuring in the sample the concentration of one or more other marker(s) of heart failure,
    c) deciding on treatment of the subject by comparing the thus determined concentration with a reference amount.

39. The method according to 8, wherein the treatment is administration of at least one of the following medicaments: Diuretics, calcium antagonists, adrenergic agonists, positive inotropic agents, statines, hydazaline and isosorbide dinitrate, beta blockers, aldosterone antagonists, ACE inhibitors, angiotensin receptor antagonists.

40. A method of monitoring treatment of functional and/or structural abnormalities of the heart preceding heart failure in a subject, the method comprising the steps of
    a) determining the concentration of at least one cardiac troponin or a variant thereof,
    b) optionally measuring in the sample the concentration of one or more other marker(s) of heart failure, and
    c) assessing whether the subject has undergone a change in its pathophysiological state by comparing the thus determined concentration of the said markers as determined in step a) to its concentration in a control sample.

41. A method of diagnosing heart failure in a subject, the method comprising the steps of
    a) measuring in a sample obtained from the subject the concentration of at least one cardiac troponin or a variant thereof,
    b) optionally measuring in the sample the concentration of one or more other marker(s) of heart failure, and
    c) assessing the heart failure by comparing the concentration determined in step (a) and optionally the concentration(s) determined in step (b) with a reference amount.

42. A method of monitoring a medication in a subject subjected to said medication and suffering from heart failure or stages preceding heart failure including risk factors for heart failure, the method comprising the steps of
    a) measuring in a sample obtained from the subject the concentrations of at least one cardiac troponin or a variant thereof and/or a natriuretic peptide or a variant thereof,
    b) measuring in a sample the concentration of GDF-15 or a variant thereof, and
    c) monitoring the medication by comparing the thus determined concentrations with a reference amount.

43. A method of deciding on the adaptation of a medication in a subject subjected to said medication and suffering from heart failure or stages preceding heart failure including risk factors for heart failure, the method comprising the steps of
    a) measuring in a sample obtained from the subject the concentrations of at least one cardiac troponin or a variant thereof and/or a natriuretic peptide or a variant thereof,
    b) measuring in a sample the concentration of GDF-15 or a variant thereof,
    c) deciding on the adaptation of the medication by comparing the thus determined concentrations with a reference amount.

44. The method according to 42 or 43, wherein the medication is selected from ACE inhibitors, angiotension receptor blockers and aldosterone antagonists.

EXAMPLES

Methods and Materials

Troponin T was determined using Roche's electrochemiluminescence ELISA sandwich test Elecsys™ Troponin T hs (high sensitive) STAT (Short Turn Around Time) assay. The test employs two monoclonal antibodies specifically directed against human cardiac troponin T. The antibodies recognize two epitopes (amino acid position 125-131 and 136-147) located in the central part of the cardiac troponin T protein, which consists of 288 amino acids. The hs-TnT assay allows a measurement of troponin T levels in the range of 3 to 10000 pg/mL.

NT-proBNP was determined using Roche's electrochemiluminescence ELISA sandwich test Elecsys™ proBNP II STAT (Short Turn Around Time) assay. The test employs two monoclonal antibodies which recognize epitopes located in the N-terminal part (1-76) of proBNP (1-108).

To determine the concentration of GDF-15 in serum and plasma samples, an Elecsys™ prototype test was employed, using a polyclonal, GDF-15 affinity chromatography-purified, goat anti-human GDF-15 IgG antibody from R&D Systems (AF957). In each experiment, a standard curve was generated with recombinant human GDF-15 from R&D Systems (957-GD/CF). The results with new batches or recombinant GDF-15 protein were tested in standard plasma samples and any deviation above 10% was corrected by introducing an adjustment factor for this assay. GDF-15 measurements in serum and plasma samples from the same patient yielded virtually identical results after correction for eventual dilution factors. The detection limit of the assay was 200 pg/ml.

For detection of IGFBP7 in human serum or plasma, a sandwich ELISA was used. For capture and detection of the antigen, aliquots of an anti-IGFBP7 polyclonal antibody from R&D Systems (Catalogue number: AF 1334) was conjugated with biotin and digoxigenin, respectively.

Streptavidin-coated 96-well microtiter plates were incubated with 100 pi biotinylated anti-IGFBP7 polyclonal antibody for 60 min at 1 pg/ml in 1×PBS solution. After incubation, plates were washed three times with 1×PBS+0.02% Tween-20, blocked with PBS+1% BSA (bovine serum albumen) and then washed again three times with 1×PBS+0.02% Tween-20. Wells were then incubated for 1.5 h with either a serial dilution of the recombinant IGFBP7 as standard antigen or with diluted serum or plasma samples (1:50) from patients or control individuals, respectively. After binding of IGFBP7, plates were washed three times with 1×PBS+0.02% Tween-20. For specific detection of bound IGFBP7, wells were incubated with 100 μl of digoxigenylated anti-IGFBP7 polyclonal antibody for 60 min at 1 μg/ml in 1×PBS+1% BSA. Thereafter, plates were washed three times to remove unbound antibody. In a next step, wells were incubated with 75 mU/ml anti-digoxigenin-POD conjugates (Roche Diagnostics GmbH, Mannheim, Germany, Catalog No. 1633716) for 60 min in 1×PBS+1% BSA. Plates were subsequently washed six times with the same buffer. For detection of antigen-antibody complexes, wells were incubated with 100 μl ABTS solution (Roche Diagnostics GmbH, Mannheim, Germany, Catalog No. 11685767) and the optical density (OD) was measured after 15 min at 405 and 492 nm with an ELISA reader Example 1

Troponin T, NT-proBNP, GDF 15 and IGFBP7 were determined in the following collectives of individuals. An informed consent of the patients has been obtained.

Group 1: normotensive subjects, n=32.

Group 2: hypertensive subjects bearing risk factors of suffering from heart failure (stage A), n=47.

Group 3: hypertensive subjects with functional and/or structural abnormalities of the heart preceding heart failure, (early stage B); the subjects did not have elevated NT-proBNP levels the subjects showed structural changes to the left ventricle (increased septum wall thickness (>11 mm), increased posterial wall thickness (>12 mm), or first signs of either hypertrophy or concentric hypertrophy) and/or the subjects showed a systolic dysfunction (LVEF≤50%) and/or diastolic dysfunction with preserved ejection fraction LVEF of at least 50%, n=37. The subjects did not suffer from left ventricular hypertrophy.

Group 4: subjects with dilated cardiomyopathy (DCM), n=29.

For group 1-3, the subjects did not show impaired renal function. Moreover, patients with a history of known myocardial infarction and coronary artery disease were excluded from group 1-3.

Geometrical changes to the left ventricle were determined by echocardiography (septum wall thickness ST, posterial wall thickness PWT, LVEF, LVEDD); functional changes (LVEDD) were determined by echocardiography.

The data show that the levels of Troponin T are higher in subjects of group 3 (hypertensive subjects with functional and/or structural abnormalities of the heart preceding heart failure) than in group 1 (normotensive subjects) and in group 2 (only bearing risk factors of suffering from heart failure). Troponin T levels keep on augmenting when individuals proceed to heart failure (DCM, group 4).

The data show that the levels of GDF 15 are higher in subjects of group 3 (hypertensive subjects with functional and/or structural abnormalities of the heart preceding heart failure) than in group 1 (normotensive subjects) and in group 2 (only bearing risk factors of suffering from heart failure). GDF 15 levels keep on augmenting when individuals proceed to heart failure (DCM, group 4).

The data show that the levels of IGFBP7 are higher in subjects of group 3 (hypertensive subjects with functional and/or structural abnormalities of the heart preceding heart failure) than in group 1 (normotensive subjects) and in group 2 (only bearing risk factors of suffering from heart failure). Insulin growth factor binding protein 7 levels keep on augmenting when individuals proceed to heart failure dilated cardiomyopathy (DCM, group 4).

The data show, that the levels of NT-proBNP are only enhanced in subjects of group 4 (subjects with dilated cardiomyopathy), but no difference can be observed between NT-proBNP levels in group 1 (normotensive subjects), group 2 (hypertensive subjects bearing risk factors of suffering from heart failure) and group 3 (hypertensive subjects with functional and/or structural abnormalities of the heart preceding heart failure).

It was surprisingly found that troponin levels can identify subjects at early stage B even before hypertrophy becomes apparent, i.e. the subjects have risk factors of suffering from heart failure and show first structural changes to the left ventricle, but do not suffer from hypertrophy. Similar diagnostic information is provided by GDF-15 and IGFBP7.

Data are shown in the following tables 1, 2, 3 and 4. FIGS. 1, 2, 3 and 4 are graphical displays of the data in tables 1, 2, 3 and 4, respectively.

TABLE 1

Troponin T concentrations in patient groups.

| hs-TnT Conc [pg/mL] | Group 1 | Group 2 | Group 3 | Group 4 |
| --- | --- | --- | --- | --- |
| Quartil 1 | 0.99 | 0.44 | 4.37 | 3.96 |
| min | 0.00 | 0.00 | 1.02 | 0.00 |
| med | 2.77 | 2.38 | 6.64 | 8.79 |
| max | 17.20 | 38.20 | 56.40 | 45.35 |
| Quartil 3 | 5.44 | 7.49 | 8.79 | 21.83 |
| n | 32 | 47 | 37 | 29 |
| MW | 3.69 | 5.14 | 8.26 | 13.27 |

TABLE 2

GDF-15 concentrations in patient group.

| GDF-15 Conc [ng/mL] | Group 1 | Group 2 | Group 3 | Group 4 |
| --- | --- | --- | --- | --- |
| Quartil 1 | 0.554 | 0.569 | 0.584 | 0.625 |
| min | 0.400 | 0.372 | 0.442 | 0.402 |
| med | 0.621 | 0.684 | 0.728 | 0.893 |
| max | 1.559 | 1.484 | 1.445 | 9.337 |
| Quartil 3 | 0.758 | 0.885 | 0.913 | 1.331 |
| n | 32 | 47 | 37 | 29 |
| MW | 0.689 | 0.741 | 0.794 | 1.269 |

TABLE 3

IGFBP7 concentrations in patient group.

| Conc [ng/mL] | Group 1 | Group 2 | Group 3 | Group 4 |
| --- | --- | --- | --- | --- |
| Quartil 1 | 33.31 | 36.70 | 42.45 | 39.05 |
| min | 22.35 | 18.85 | 27.50 | 20.25 |
| med | 38.75 | 43.05 | 49.70 | 47.25 |
| max | 66.25 | 68.50 | 105.20 | 131.95 |
| Quartil 3 | 46.23 | 51.25 | 58.90 | 64.15 |
| n | 32 | 47 | 37 | 29 |
| MW | 40.47 | 43.88 | 51.02 | 53.16 |

TABLE 4

NT-proBNP concentrations in patient group.

| Conc [pg/mL] | Group 1 | Group 2 | Group 3 | Group 4 |
| --- | --- | --- | --- | --- |
| Quartil 1 | 49.5 | 41.4 | 43.4 | 264.2 |
| min | 24.8 | 7.8 | 0.9 | 37.0 |
| med | 75.8 | 106.8 | 74.5 | 383.7 |
| max | 814.8 | 626.2 | 1555.8 | 4438.7 |
| Quartil 3 | 154.1 | 240.7 | 209.7 | 922.1 |
| n | 32 | 47 | 37 | 29 |
| MW | 134.3 | 159.2 | 229.5 | 899.9 |

As it can be seen from table 1, the troponin T levels in patients belonging to group 3 were more than 30% increased as compared to patients belonging to group 1 and 2. Thus, an increase of at least 30% is indicative for the presence of functional and/or structural abnormalities preceding LVH and/or preceding heart failure in patients without LVH.

In contrast and as it can be seen from table 4, the Nt-ProBNP levels in patients belonging to group 3 remain unchanged as compared to patients belonging to group 1 and 2. Thus, patients with no LVH and with functional and/or functional abnormalities preceding LVH and/or preceding heart failure do not have increased levels of Nt-ProBNP of at least 20% as compared with reference amounts in healthy individuals (group 1).

Levels of both, IGFBP7 and GDF15 are at least 10% increased in patients belonging to group 3 as compared to levels in patients belonging to group 1 and group 2. as demonstrated in tables 2 and 3.

As can be seen from table 3, IGFBP7 levels are increased at least 20% in stage 3 patients in respect to reference amounts in healthy subjects belonging to group 1.

Table 5 shows the distribution of septum and posterial wall thickness in subject belonging to groups 1, 2 and 3.

TABLE 5

Distribution of septum and posterial wall thickness.

| | Group 1 Normotensive subjects (n = 32) | Group 2 Hypertensive subjects (n = 47) | Group 3 Hypertensive subjects with structural abnormalities of the heart (n = 37) |
| --- | --- | --- | --- |
| Mean value septum wall thickness (mm) | 9.5 (8-11) | 9.7 (7-11) | 13.3 (12-16) |
| Mean value posterial wall thickness (mm) | 10.2 (9-12) | 9.5 (5-10) | 13.4 (11-18) |

As can be seen from table 5, subjects from group 3 had an increased septum wall thickness above 11 mm (mean value of 13.3 mm, between 12 and 16 mm) as well as an increased posterial wall thickness (mean value 13.4 mm). Patients belonging to group 1 and 2 had no structural changes preceding LVH and/or preceding heart failure with mean values of septum and posterial wall thickness ranging from 9.5-10.2.

Thus patients belonging to group 3 (Early stage B) exhibited structural changes preceding LVH and/or heart failure as an increased septum wall thickness above 11 mm (mean value 13.3 mm, range 12-16 mm). Patients belonging to group 2 (stage A) and group 1 (healthy) had no structural changes, e.g. no increased septum wall thickness above 11 mm.

TABLE 6

Characteristics of patient groups 1, 2 and 3: Distribution of gender, age and various risk factors for developing LVH/HF.

| | Group 1 Normotensive subjects (n = 32) | Group 2 Hypertensive subjects without structural abnormalities (n = 47) | Group 3 Hypertensive subjects with structural abnormalities (n = 37) |
|---|---|---|---|
| Age (yrs) | 59 (36-75) | 61 (36-85) | 64 (48-80) |
| Male Gender | 28% (9/32) | 57% (27/47) | 54% (20/37) |
| History of smoking | 27% (8/30) | 36% (16/45) | 44% (15/34) |
| Diabetes mellitus type2 | 6% (2/31) | 13% (6/45) | 18% (6/33) |
| Diabetes mellitus type 2 and/or fasting glucose >110 mg/dl | 13% (4/31) | 21% (22/47) | 22% (16/35) |
| Lipids | 53% (16/30) | 80% (37/46) | 61% (22/36) |
| Adipositas | 25% (7/28) | 45% (20/44) | 57% (20/35) |

As can be seen from table 6, all patients belonging to the groups 2 and 3, as well as the apparently healthy subjects of group 1 had a comparable mean age of 60 years.

Half of the patients at HF stage A or early stage B (groups 2 and 3) were female and all of them had arterial hypertension. As visible in table 6, 20% of them had Diabetes type 2 and/or fasting glucose levels below 110 mg/dL.

TABLE 7 validity of cut-offs for various risk factors for developing LVH/HF.

| | Group 1 Normotensive subjects | Group 2 Hypertensive subjects w/o struct. Abnorm. | Group 3 Hypertensive subjects with structural abnormalities | % increase in respect to normotensive subjects | % increase in respect to hypertensive subjects w/o struct. abnorm. |
|---|---|---|---|---|---|
| Cohort of example 1 | 2.77 | 2.38 | 6.64 | >30% | >50% |
| Ecluding subjects w history of smoking | 3.12 | 2.38 | 6.73 | >30% | >50% |
| Excluding subjects w diabetes mellitus type2 | 2.66 | 2.06 | 6.41 | >30% | >50% |
| Excluding subjects w diabetes type2 a/o glucose >110 mg/dl | 2.63 | 2.06 | 6.64 | >30% | >50% |
| Excluding subjects w lipids | 2.89 | 2.06 | 6.93 | >30% | >50% |
| Excluding subjects w adipositas | 2.66 | 2.41 | 6.64 | >30% | >50% |

As it can be seen from table 1 beforehand, the troponin T levels in patients belonging to group 3 were more than at least 20% (>3.3 pg/ml), 30% (>3.5 pg/ml) and even more than 50% (>4.2 pg/ml) increased as compared to patients belonging to group 1 and 2. By stepwise exclusion of single risk factors it can be seen from table 7, that Troponin T levels were increased at least 30% (>3.5 pg/ml) in early stage B patients compared to stage A patients with respective risk factors or normotensive apparently healthy subjects.

The validity of a cut-off of TnT levels above 3.3, and in some cases above 3.5 pg/ml or even above 4.2 pg/ml to diagnose early structural and/or functional changes preceding LVH and/or heart failure in subjects with arterial hypertension was shown by step-wise exclusion of different risk factor groups.

Thus, an increase of at least 30%, and in some cases of at least 50% is indicative for the presence of functional and/or structural abnormalities preceding LVH and/or preceding heart failure in patients with arterial hypertension with or without further risk factors, e.g. diabetes type 2.

TABLE 8

Validation of increased Troponin T levels in early stage B patients with different risk factors for developing LVH/HF.

| | Group 1 Normotensive subjects | Group 2 Hypertensive subjects | Group 3 Hypertensive subjects with structural abnormalities | % increase in respect to normotensive subjects | % increase in respect to hypertensive subjects w/o struct. Abnorm. |
|---|---|---|---|---|---|
| Cohort of example 1 | 2.77 | 2.38 | 6.64 | >30% | >30% |
| Females only | 2.63 | 1.80 | 6.73 | >30% | >50% |
| Males only | 3.11 | 4.35 | 6.42 | >30% | >20% |
| Only subjects w history of smoking | 1.99 | 3.21 | 6.64 | >20% | >30% |
| Only subjects w diabetes type 2 a/o glucose >110 mg/dl | 3.38 | 3.61 | 5.75 | >30% | >30% |
| Only subjects w lipids | 1.84 | 3.09 | 6.68 | >30% | >30% |
| Only subjects w adipositas | 1.02 | 1.98 | 6.41 | >30% | >30% |

The validity of increased TnT levels of at least 20% in hypertensive individuals with structural abnormalities in respect to hypertensives w/o structural abnormalities (and normotensive individuals) is shown for different risk factor subgroups (adipositas, history of smoking, . . . ).

As can be seen from table 8 increased TnT levels discriminate female patients with arterial hypertension with and without structural changes better than male patients (increase of at least 50% versus at least 20%).

Thus elevated TnT levels indicate early structural and/or functional changes preceding LVH and/or heart failure, in particular in hypertensive women.

TABLE 9 validity of cut-offs for various risk factors for developing LVH/HF.

| | Group 1 Normotensive subjects | Group 2 Hypertensive subjects w/o struct. Abnorm. | Group 3 Hypertensive subjects with structural abnormalities | % increase in respect to normotensive subjects |
|---|---|---|---|---|
| Cohort of example 1 | 38.7 | 43.0 | 49.70 | >20% |
| Ecluding subjects w history of smoking | 40.8 | 42.4 | 48.6 | >10% |
| Excluding subjects w diabetes mellitus type2 | 38.8 | 42.4 | 47.3 | >20% |
| Excluding subjects w lipids | 37.6 | 43.4 | 48.0 | >20% |
| Excluding subjects w adipositas | 39.1 | 43.1 | 46.9 | >10% |

As it can be seen from table 1 beforehand, the IGFBP7 levels in patients belonging to group 3 were more than at least 10% and even more than 20% (>46.5 pg/ml) increased as compared to patients belonging to group 1 and 2. By stepwise exclusion of single risk factors it can be seen from table 9, that IGFBP7 levels were increased at least 10% in early stage B patients compared to stage A patients with respective risk factors or normotensive apparently healthy subjects.

Thus, an increase of at least 10%, and ins some cases at least 20% is indicative for the presence of functional and/or structural abnormalities preceding LVH and/or preceding heart failure in patients with arterial hypertension with or without further risk factors, e.g. adipositas.

The validity of a cut-off of IGFBP7 levels above 46.5 pg/ml to diagnose early structural and/or functional changes preceding LVH and/or heart failure in subjects with arterial hypertension was shown by step-wise exclusion of different risk factor groups.

TABLE 10 validation of increased IGFBP7 levels in early stage B patients with different risk factors. The validity of increased TnT levels of at least 10% in hypertensive individuals with structural abnormalities in respect to hypertensives w/o structural abnormalities (and normotensive individuals) is shown for different risk factor subgroups (lipids, history of smoking, . . .).

|  | Group 1 Normotensive subjects | Group 2 Hypertensive subjects | Group 3 Hypertensive subjects with structural abnormalities | % increase in respect to normotensive subjects |
|---|---|---|---|---|
| Cohort of example 1 | 38.7 | 43.05 | 49.70 | >20% |
| Only females | 40.8 | 42.2 | 49.2 | >20% |
| Only males | 34.0 | 44.7 | 47.65 | >20% |
| Only subjects w lipids | 40.8 | 42.5 | 47.1 | >10% |
| Only subjects w adipositas | 39.6 | 42.0 | 47.3 | >10% |

Thus elevated IGFBP7 levels indicated early structural and/or functional changes preceding LVH and/or heart failure, in particular in hypertensive women.

Example 2

Troponin T, NT-proBNP and GDF-15 were determined in the below-described collective of individuals. A total of 97 patients with overt heart failure were included into the study, mean age 60.9 years, 52 males, 45 females, LVEF below 50%, who had a normal kidney function as documented by normal creatinine levels. All patients were on beta blocker as well as on ACE inhibitor therapy, 59 patients were on aldosterone antagonists, 38 did not receive aldosterone antagonists. Patients were treated in the study according to guidelines (see above). None of the patients suffered from diabetes mellitus or metabolic syndrome, in addition none of the patients suffered from liver disease or malignancies.

38 patients receiving no aldosterone (all Class C) had the following characteristics:

TABLE 11

Marker concentrations in 38 patients receiving no aldosterone.

| Percentile | NT-pro BNP (pg/mL) | Troponin T (pg/mL) | GDF-15 (pg/mL) | LVEF (%) | NYHA class | ratio NT-pro BNP/GDF 15 | ratio Troponin T/GDF 15 |
|---|---|---|---|---|---|---|---|
| 25 | 157 | 1.7 | 663 | 57 | 1.0 | 0.196 | 0.002 |
| 50 | 464 | 6.6 | 1161 | 45 | 1.5 | 0.401 | 0.005 |
| 75 | 1195 | 18.1 | 2228 | 28.5 | 2.5 | 0.682 | 0.011 |

Patients receiving aldosterone antagonists (all class C) has the following characteristics:

TABLE 12

Marker concentrations in patients receiving aldosterone antagonists.

| Percentile | NT-pro BNP (pg/mL) | Troponin T (pg/mL) | GDF-15 (pg/mL) | LVEF (%) | NYHA class | ratio NT-pro BNP/GDF 15 | ratio Troponin T/GDF 15 |
|---|---|---|---|---|---|---|---|
| 25 | 475 | 7.3 | 915 | 35 | 1.0 | 0.254 | 0.004 |
| 50 | 1194 | 15.3 | 1535 | 28 | 2.0 | 0.800 | 0.009 |
| 75 | 2072 | 24.0 | 2493 | 20 | 3.0 | 1.898 | 0.017 |

Patients who received aldosterone antagonists had more severe heart failure than those who did not receive aldosterone antagonists. When ratios were formed it became however clear that GDF 15 was lower relative to NT-pro BNP and GDF 15 in the aldosterone antagonist group indicating that GDF 15 was a valuable marker for the use and monitoring of aldosterone antagonists.

As described above the recommendation of ACE inhibitors in stages A and B suggest the need for anti inflammatory treatment, however because of polymorphisms this appears not to be effective in all cases, thus low dose aldosterone antagonists are likely to be useful also in stages A and B heart failure. The ratios of NT-pro BNP/GDF 15 and Troponin T/GDF 15 give guidance as to the use of this drug. In all cases, in other words while ACE inhibitors and angiotension receptor blockers (ARBs) have been shown to be effective in large randomized trials there is currently no method available to diagnose the effectiveness of these drugs in the individual patient. This is in contrast to the application of these drugs in patients with kidney disease where the decrease of urinary albumin can be used to verify treatment success. Thus the method described offers for the first time a method for the diagnosis of treatment failure and provides guidance for improved treatment using aldosterone inhibitors or in the future drugs that inhibit synthesis of aldosterone.

Case Studies:

A 62 year old patient with stable established class C heart failure is currently on a combination of beta blockers and ACE inhibitors. GDF-15, NT-proBNP and Troponin T are determined in serum sample obtained from the patient. The NT-pro BNP/GDF 15 ratio is 0.39, and the Troponin T/GDF 15 ratio is 0.003. Because of inappropriate therapy he is started with spironolactone 25 mg/day. Three months later, the NT-pro BNP/GDF 15 ratio is 0.62 and Troponin T/GDF 15 ratio is 0.006. Because of the still inappropriate therapy, spironolactone is increased to 50 mg/day. Again 3 months later therapy is found appropriate with a NT-pro BNP/GDF 15 ratio of 0.9 and a troponin T/GDF 15 ratio of 0.012.

A 48 year old female patient with stable class C heart failure is on standard therapy with beta blockers and ACE inhibitors. GDF-15, NT-proBNP and Troponin T are determined in plasma sample obtained from the patient. The NT pro BNP/GDF 15 ratio is 0.95 and the Troponin T/GDF 15 ratio 0.011. The results indicate that the patient does not require therapy with an aldosterone antagonist. As the therapy has only been started 9 months ago, she is informed of the possibility of ACE inhibitor resistance and is advised to have a follow up visit in 12 months or when symptoms of heart failure develop.

A 68 year old male patient with stable heart failure class C is currently on a combination of beta blocker, ACE inhibitors and low dose aldosterone antagonists. The NT-pro BNP/GDF 15 ratio is 0.95 and the troponin T/GDF 15 ratio is 0.012. The patient is informed that therapy is adequate and to stay on current treatment schedule and to return to a follow up visit in 12 months or if symptoms worsen.

A 56 year old patient with stable type C heart failure is on a therapy with beta blockers, ACE inhibitors and 25 mg/day spironolactone, the NT-pro BNP/GDF 14 ratio is 1,7, the Troponin T/GDF 15 ratio is 0.02. The patient is advised that an attempt can be made to discontinue spironolactone for three months, as the effect of discontinuation is only recognised with significant delay, and then to decide on the necessity of spironolactone. Three months after discontinuation of spironolactone the NT-pro BNP/GDF 15 ratio is 0.9 and the troponin T/GDF 14 ratio is 0.013. The patient is informed that spironolactone can be discontinued.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of diagnosing a heart functional and/or structural abnormality preceding heart failure in a human subject, the method comprising the steps of:
   a) contacting, in vitro, a portion of a serum or plasma sample from the subject with a first antibody having specific binding affinity for an epitope of cardiac troponin to form complex of the antibody and the cardiac troponin T;
   b) calculating a concentration of the cardiac troponin T in the portion of the sample by measuring an amount of the complex formed in said step of contacting;
   c) comparing the concentration of the cardiac troponin T determined in said step of calculating with cardiac troponin T reference value;
   d) diagnosing a heart functional and/or structural abnormality preceding heart failure in the subject if the concentration of the cardiac troponin T in the sample is greater than the cardiac troponin T reference value; and
   e) treating the subject diagnosed with the heart functional and/or structural abnormality with an angiotensin-converting enzyme (ACE) inhibitor, an angiotensin-II-receptor blocker (ARB), an aldosterone antagonist, and/or a beta blocker; wherein the structural abnormality of the heart preceding heart failure comprises an abnormality selected from a left ventricular structural change, an increased septum diameter, and an increased posterial wall diameter, and the functional abnormality is diastolic dysfunction; and further wherein the subject has hypertension but does not have left ventricular hypertrophy.

2. The method of claim 1, wherein the first antibody comprises a detectable label.

3. The method of claim 2, wherein the detectable label is one of a radioactive and a fluorescent label.

4. The method of claim 1, wherein the step of contacting further comprises contacting the portion of the sample of the subject with a second antibody having specific binding affinity for a second epitope of the cardiac troponin T to form a complex of the first antibody, the cardiac troponin T and the second antibody.

5. The method of claim 4, wherein the second antibody comprises a detectable label.

6. The method of claim 5, wherein the detectable label is one of a radioactive and a fluorescent label.

7. The method according to claim 1, wherein prior to performing steps a)-d), the subject is known to suffer from one of hypertension and diabetes.

8. The method of claim 1, wherein the structural abnormality is an increased septum diameter.

9. The method of claim 1, wherein the cardiac troponin T reference value is an amount at least 20% greater than an amount of cardiac troponin T in a population of healthy individuals.

10. The method of claim 4, wherein the first antibody is bound to a solid phase and the second antibody is not bound to a solid phase.

11. The method of claim 1, further comprising the steps of:
   contacting, in vitro, the portion of the sample of the subject with an antibody having specific binding affinity for an epitope of insulin-like growth factor-binding protein 7, to form a complex of the antibody and the insulin-like growth factor-binding protein 7;
   calculating a concentration of the insulin-like growth factor-binding protein 7 in the portion of the sample by measuring complex formed in said step of contacting; and
   comparing the concentration of the insulin-like growth factor-binding protein 7 to an insulin-like growth factor-binding protein 7 reference value, wherein said step of diagnosing further comprises diagnosing the heart functional and/or structural abnormality preceding heart failure in the subject only if the concentration of the cardiac troponin T in the portion of the sample is greater than the cardiac troponin T reference value and the concentration of the insulin-like growth factor-binding protein 7 in the portion of the sample is greater than the insulin-like growth factor-binding protein 7 reference value.

12. The method of claim 1 wherein the subject does not have renal failure.

* * * * *